US011059834B2

(12) United States Patent
Malathong et al.

(10) Patent No.: US 11,059,834 B2
(45) Date of Patent: *Jul. 13, 2021

(54) MACROCYCLIC IMMUNOMODULATORS

(71) Applicant: CHEMOCENTRYX, INC., Mountain View, CA (US)

(72) Inventors: Viengkham Malathong, Mountain View, CA (US); Jeffrey McMahon, San Francisco, CA (US); Darren J. McMurtrie, Sunnyvale, CA (US); Sreenivas Punna, Sunnyvale, CA (US); Howard S. Roth, Sunnyvale, CA (US); Rajinder Singh, Belmont, CA (US); Penglie Zhang, Foster City, CA (US)

(73) Assignee: ChemoCentryx, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/504,536

(22) Filed: Jul. 8, 2019

(65) Prior Publication Data

US 2020/0055869 A1 Feb. 20, 2020

Related U.S. Application Data

(63) Continuation of application No. 16/057,077, filed on Aug. 7, 2018, now Pat. No. 10,392,405.

(60) Provisional application No. 62/542,694, filed on Aug. 8, 2017.

(51) Int. Cl.
| C07D 498/08 | (2006.01) |
| A61P 37/02 | (2006.01) |
| A61P 31/12 | (2006.01) |
| A61P 31/04 | (2006.01) |
| A61P 31/10 | (2006.01) |
| A61P 35/00 | (2006.01) |

(52) U.S. Cl.
CPC ........... C07D 498/08 (2013.01); A61P 31/04 (2018.01); A61P 31/10 (2018.01); A61P 31/12 (2018.01); A61P 35/00 (2018.01); A61P 37/02 (2018.01)

(58) Field of Classification Search
CPC .................................................. C07D 498/08
USPC ....................................................... 514/293
See application file for complete search history.

(56) References Cited

U.S. PATENT DOCUMENTS

| 5,604,294 A | 2/1997 | Luly et al. |
| 10,392,405 B2 | 8/2019 | Malathong et al. |
| 10,568,874 B2 | 2/2020 | Lange et al. |
| 10,639,284 B2 | 5/2020 | Lange et al. |
| 10,654,815 B2 | 5/2020 | Yang et al. |
| 10,815,208 B2 | 10/2020 | Feng et al. |
| 10,919,852 B2 | 2/2021 | Lange et al. |
| 2003/0220349 A1 | 11/2003 | MacLean et al. |
| 2008/0194557 A1 | 8/2008 | Barbosa et al. |
| 2010/0292227 A1 | 11/2010 | Yoakim et al. |
| 2014/0294898 A1 | 10/2014 | Miller et al. |

(Continued)

FOREIGN PATENT DOCUMENTS

| CN | 108395443 A | 8/2018 |
| CN | 108863963 A | 11/2018 |

(Continued)

OTHER PUBLICATIONS

International Search Report and Written Opinion dated Oct. 23, 2018 corresponding to PCT/US2018/045553 filed Aug. 7, 2018(11 pages).
Sunshine, Joel et al., "PD-1/PD-L1 Inhibitors," *Curr Opin Pharmacol.* (Aug. 2015) 23:32-38.
International Search Report and Written Opinion dated Sep. 15, 2017 corresponding to PCT/US2017/039313 filed Jun. 26, 2017 (9 pages).
International Search Report and Written Opinion dated Oct. 10, 2018 corresponding to PCT/US2018/044088 filed Jul. 27, 2018(11 pages).

(Continued)

*Primary Examiner* — Taofiq A Solola
(74) *Attorney, Agent, or Firm* — Mintz Levin Cohn Ferris Glovsky and Popeo PC

(57) ABSTRACT

Compounds are provided that are useful as immunomodulators. The compounds have the following Formula (I) or (II):

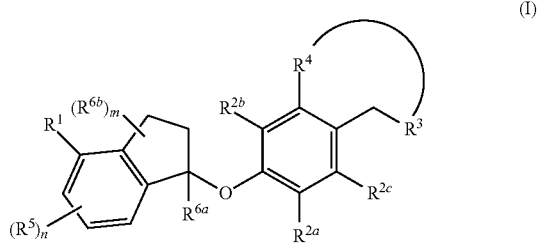

(I)

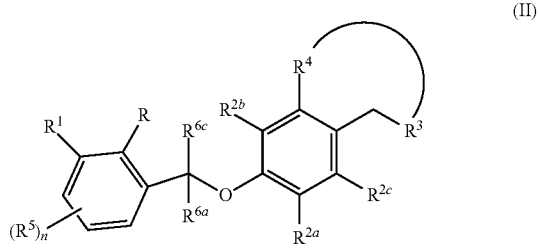

(II)

including stereoisomers and pharmaceutically acceptable salts thereof, wherein R, $R^1$, $R^{2a}$, $R^{2b}$, $R^{2c}$, $R^3$, $R^4$, $R^5$, $R^{6a}$, $R^{6b}$, $R^{6c}$, m and n are as defined herein. Methods associated with preparation and use of such compounds, as well as pharmaceutical compositions comprising such compounds, are also disclosed.

18 Claims, No Drawings

(56) References Cited

U.S. PATENT DOCUMENTS

| | | |
|---|---|---|
| 2015/0346210 A1 | 12/2015 | Nitta et al. |
| 2017/0107216 A1 | 4/2017 | Wu et al. |
| 2017/0145025 A1 | 5/2017 | Li et al. |
| 2017/0174679 A1 | 6/2017 | Lajkiewicz et al. |
| 2019/0308957 A1 | 10/2019 | Wang et al. |
| 2020/0375962 A1 | 12/2020 | Lange et al. |
| 2020/0392083 A1 | 12/2020 | Jiang et al. |
| 2021/0008049 A1 | 1/2021 | Malathong et al. |
| 2021/0032270 A1 | 2/2021 | Yang et al. |

FOREIGN PATENT DOCUMENTS

| | | |
|---|---|---|
| CN | 109336857 A | 2/2019 |
| CN | 109438263 A | 3/2019 |
| CN | 109503546 A | 3/2019 |
| CN | 109665968 A | 4/2019 |
| CN | 109721527 A | 5/2019 |
| CN | 109776377 A | 5/2019 |
| CN | 109776445 A | 5/2019 |
| CN | 110128415 A | 8/2019 |
| CN | 110200959 A | 9/2019 |
| EP | 3 733 659 A1 | 11/2020 |
| WO | 2007/126957 A2 | 11/2007 |
| WO | 2008/008059 A1 | 1/2008 |
| WO | 2014/165422 A1 | 10/2014 |
| WO | 2015/033299 A1 | 3/2015 |
| WO | 2015/033301 A1 | 3/2015 |
| WO | 2015/034820 A1 | 3/2015 |
| WO | 2015/160641 A2 | 10/2015 |
| WO | 2015/160641 A3 | 10/2015 |
| WO | 2016/142886 A2 | 9/2016 |
| WO | 2016/142886 A3 | 9/2016 |
| WO | 2016/142894 A1 | 9/2016 |
| WO | 2017/066227 A1 | 4/2017 |
| WO | 2017/070089 A1 | 4/2017 |
| WO | 2017/106634 A1 | 6/2017 |
| WO | 2017/112730 A1 | 6/2017 |
| WO | 2017/118762 A1 | 7/2017 |
| WO | 2017/176965 A1 | 10/2017 |
| WO | 2017/192961 A1 | 11/2017 |
| WO | 2017/202273 A1 | 11/2017 |
| WO | 2017/202274 A1 | 11/2017 |
| WO | 2017/202275 A1 | 11/2017 |
| WO | 2017/202276 A1 | 11/2017 |
| WO | 2017/205464 A1 | 11/2017 |
| WO | 2017/222976 A1 | 12/2017 |
| WO | 2018/006795 A1 | 1/2018 |
| WO | 2018/009505 A1 | 1/2018 |
| WO | 2018/013789 A1 | 1/2018 |
| WO | 2018/044783 A1 | 3/2018 |
| WO | 2018/044963 A1 | 3/2018 |
| WO | 2018/045142 A1 | 3/2018 |
| WO | 2018/051254 A1 | 3/2018 |
| WO | 2018/051255 A1 | 3/2018 |
| WO | 2018/118848 A1 | 6/2018 |
| WO | 2018/119221 A1 | 6/2018 |
| WO | 2018/119224 A1 | 6/2018 |
| WO | 2018/119236 A1 | 6/2018 |
| WO | 2018/119263 A1 | 6/2018 |
| WO | 2018/119266 A1 | 6/2018 |
| WO | 2018/119268 A1 | 6/2018 |
| WO | 2018/119286 A1 | 6/2018 |
| WO | 2018/121560 A1 | 7/2018 |
| WO | 2018/183171 A1 | 10/2018 |
| WO | 2018/195321 A1 | 10/2018 |
| WO | 2018196768 A1 | 11/2018 |
| WO | 2019/023575 A1 | 1/2019 |
| WO | 2019/034172 A1 | 2/2019 |
| WO | 2019/070643 A1 | 4/2019 |
| WO | 2019/076343 A1 | 4/2019 |
| WO | 2019/087214 A1 | 5/2019 |
| WO | 2019120297 A1 | 6/2019 |
| WO | 2019/128918 A1 | 7/2019 |
| WO | 2019/147662 A1 | 8/2019 |
| WO | 2019/149183 A1 | 8/2019 |
| WO | 2019/160882 A1 | 8/2019 |
| WO | 2019/169123 A1 | 9/2019 |
| WO | 2019/174533 A1 | 9/2019 |
| WO | 2019/175897 A1 | 9/2019 |
| WO | 2019/191707 A1 | 10/2019 |
| WO | 2019/192506 A1 | 10/2019 |
| WO | 2019/204609 A1 | 10/2019 |
| WO | 2019/217821 A1 | 11/2019 |
| WO | 2020/011209 A1 | 1/2020 |
| WO | 2020/011243 A1 | 1/2020 |
| WO | 2020/014643 A1 | 1/2020 |
| WO | 2020/015716 A1 | 1/2020 |
| WO | 2020/015717 A1 | 1/2020 |
| WO | 2020/025030 A1 | 2/2020 |

OTHER PUBLICATIONS

International Search Report dated Apr. 16, 2019 corresponding PCT/US2019/018919 filed Feb. 21, 2019; 19 pages.

International Search Report and Written Opinion dated Dec. 27, 2019 corresponding to PCT/US2019/048466 filed Aug. 28, 2019; 19 pages.

International Search Report dated Oct. 8, 2020 corresponding to PCT/US2020/041316 filed Jul. 9, 2020; 8 pages.

Extended European Search Report dated Jan. 20, 2018 corresponding to EP 17821019.1 filed Jun. 26, 2017 (8 pages).

Extended European Search Report dated Oct. 23, 2020 corresponding to EP 18837877.2 filed Jul. 27, 2018 (8 pages).

MACROCYCLIC IMMUNOMODULATORS

CROSS-REFERENCES TO RELATED APPLICATIONS

This application is a continuation of U.S. patent application Ser. No. 16/057,077 filed Aug. 7, 2018, which is an application claiming priority benefit under 35 U.S.C. § 119(e) to U.S. Provisional Application Ser. No. 62/542,694 filed Aug. 8, 2017, each of which is incorporated herein by reference in its entirety for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE DISCLOSURE

Programmed cell death protein-1 (PD-1) is a member of the CD28 superfamily that delivers negative signals upon interaction with its two ligands, PD-L1 or PD-L2. PD-1 and its ligands are broadly expressed and exert a wide range of immunoregulatory roles in T cells activation and tolerance. PD-1 and its ligands are involved in attenuating infectious immunity and tumor immunity, and facilitating chronic infection and tumor progression.

Modulation of the PD-1 pathway has therapeutic potential in various human diseases (Hyun-Tak Jin et al., Curr Top Microbiol Immunol. (2011); 350:17-37). Blockade of the PD-1 pathway has become an attractive target in cancer therapy. Therapeutic antibodies that block the programmed cell death protein-1 (PD-1) immune checkpoint pathway prevent T-cell down regulation and promote immune responses against cancer. Several PD-1 pathway inhibitors have shown robust activity in various phases of clinical trials (RD Harvey, Clinical Pharmacology and Therapeutics (2014); 96(2), 214-223).

Accordingly, agents that block the interaction of PD-L1 with either PD-1 or CD80 are desired. Some antibodies have been developed and commercialized. However there is still a need for alternative compounds such as small molecules which may have advantageous characteristics in term of oral administration, stability, bioavailability, therapeutic index, and toxicity. A few patent applications disclosing non-peptidic small molecules have been published (WO 2015/160641, WO 2015/034820, WO 2017/066227, WO 2018/00905, WO 2018/044963, and WO 2018/118848 from BMS; WO 2015/033299, WO 2015/033301, WO 2016/142886, WO 2016/142894, WO 2018/051254, and WO 2018/051255 from Aurigene; WO 2017/070089, US 2017/0145025, WO 2017/106634, US2017/0174679, US 2017/0107216, WO 2017/112730, WO 2017/192961, WO 2017/205464, WO 2017/222976, WO 2018/013789, WO 2018/044783, WO 2018/119221, WO 2018/119224, WO 2018/119236, WO 2018/119263, WO 2018/119266, and WO 2018/119286 from Incyte) However, there remains a need for alternative small molecules useful as inhibitors of the PD-1 pathway.

BRIEF SUMMARY OF THE DISCLOSURE

In one aspect, provided herein are compounds having the Formula (I) or (II):

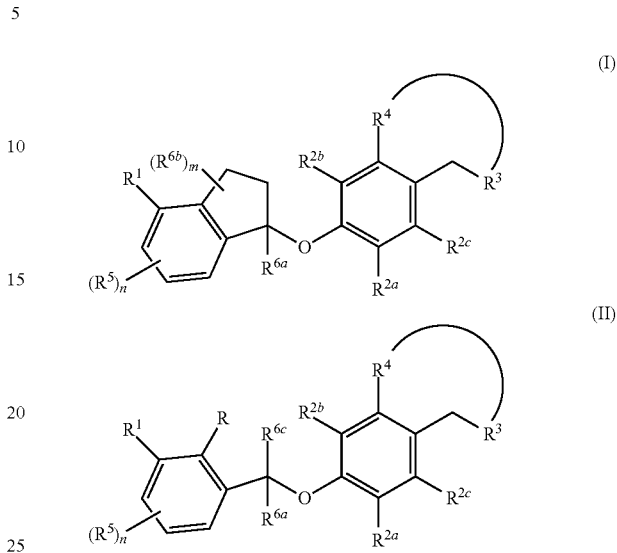

or a pharmaceutically acceptable salt thereof, wherein R, $R^1$, $R^{2a}$, $R^{2b}$, $R^{2c}$, $R^3$, $R^4$, $R^5$, $R^{6a}$, $R^{6b}$, $R^{6c}$, m and n are as defined herein.

In addition to the compounds provided herein, the present disclosure further provides pharmaceutical compositions containing one or more of these compounds, as well as methods associated with preparation and use of such compounds. In some embodiments, the compounds are used in therapeutic methods to treat diseases associated with the PD-1/PD-L1 pathway.

BRIEF DESCRIPTION OF THE DRAWINGS

NOT APPLICABLE

DETAILED DESCRIPTION OF THE DISCLOSURE

Abbreviation and Definitions

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The term "alkyl", by itself or as part of another substituent, means, unless otherwise stated, a straight or branched chain hydrocarbon group, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of alkenyl groups include vinyl, 2-propenyl, crotyl, 2-isopentenyl, 2-(butadienyl), 2,4-pentadienyl and 3-(1,4-pentadienyl). Examples of alkynyl groups include ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The bicyclic or polycyclic rings may be fused, bridged, spiro or a combination thereof. The term "heterocycloalkyl" or "heterocyclyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycyclic ring system. The bicyclic or polycyclic rings may be fused, bridged, spiro or a combination thereof. It is understood that the recitation for $C_{4-12}$ heterocyclyl, refers to a group having from 4 to 12 ring members where at least one of the ring members is a heteroatom. Non limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A heterocycloalkyl group can be attached to the remainder of the molecule through a ring carbon or a heteroatom.

The term "alkylene" by itself or as part of another substituent means a divalent group derived from an alkane, as exemplified by —$CH_2CH_2CH_2CH_2$—. Typically, an alkyl (or alkylene) group will have from 1 to 12 carbon atoms, with those groups having 8 or fewer carbon atoms being preferred in the present disclosure. Similarly, "alkenylene" and "alkynylene" refer to the unsaturated forms of "alkylene" having double or triple bonds, respectively.

The term "heteroalkyl," by itself or in combination with another term, means, unless otherwise stated, a stable straight or branched chain, or cyclic hydrocarbon group, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—OCH$_3$, and —CH=CH—N($CH_3$)—$CH_3$. Up to two heteroatoms may be consecutive, such as, for example, —$CH_2$—NH—OCH$_3$ and —$CH_2$—O—Si($CH_3$)$_3$. Similarly, the terms "heteroalkenyl" and "heteroalkynyl" by itself or in combination with another term, means, unless otherwise stated, an alkenyl group or alkynyl group, respectively, that contains the stated number of carbons and having from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group.

The term "heteroalkylene" by itself or as part of another substituent means a divalent group, saturated or unsaturated or polyunsaturated, derived from heteroalkyl, as exemplified by —$CH_2$—$CH_2$—S—$CH_2CH_2$— and —$CH_2$—S—$CH_2$—$CH_2$—NH—$CH_2$—, —O—$CH_2$—CH=CH—, —$CH_2$—CH=C(H)$CH_2$—O—$CH_2$— and —S—$CH_2$—C≡C—. For heteroalkylene groups, heteroatoms can also occupy either or both of the chain termini (e.g., alkyleneoxy, alkylenedioxy, alkyleneamino, alkylenediamino, and the like).

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —NR$^a$R$^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "hydroxyalkyl" or "alkyl-OH" refers to an alkyl group, as defined above, where at least one of the hydrogen atoms is replaced with a hydroxy group. As for the alkyl group, hydroxyalkyl groups can have any suitable number of carbon atoms, such as $C_{1-6}$. Exemplary hydroxyalkyl groups include, but are not limited to, hydroxymethyl, hydroxyethyl (where the hydroxy is in the 1- or 2-position), hydroxypropyl (where the hydroxy is in the 1-, 2- or 3-position), etc.

The term "$C_{1-3}$ alkyl-guanidinyl" refers to a $C_{1-3}$ alkyl group, as defined above, where at least one of the hydrogen atoms is replaced with a guanidinyl group (—NHC(NH) NH$_2$).

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. It is understood that the recitation for $C_{5-10}$ heteroaryl, refers to a heteroaryl moiety having from 5 to 10 ring members where at least one of the ring members is a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

The term "carbocyclic ring" "carbocyclic" or "carbocyclyl" refers to cyclic moieties with only carbon atoms as ring vertices. Carbocyclic ring moieties are saturated or unsaturated and can be aromatic. Generally, carbocyclic moieties have from 3 to 10 ring members. Carbocylic moieties with multiple ring structure (e.g. bicyclic) can include a cycloalkyl ring fused to a aromatic ring (e.g. 1,2,3,4-tetrahydronaphthalene). Thus, carboclicic rings include cyclopentyl, cyclohexenyl, naphthyl, and 1,2,3,4-tetrahydronaphthyl. The term "heterocyclic ring" refers to both "heterocycloalkyl" and "heteroaryl" moieties. Thus, heterocyclic rings are saturated or unsaturated and can be aromatic. Generally, heterocyclic rings are 4 to 10 ring members and include piperidinyl, tetrazinyl, pyrazolyl and indolyl.

When any of the above terms (e.g., "alkyl," "aryl" and "heteroaryl") are referred to as 'substituted' without further notation on the substituents, the substituted forms of the indicated group will be as provided below.

Substituents for the alkyl groups (including those groups often referred to as alkylene, alkenyl, alkynyl and cycloalkyl) can be a variety of groups selected from: -halogen, —OR', —NR'R", —SR', —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such group. R', R" and R'" each independently refer to hydrogen, unsubstituted C$_{1-8}$ alkyl, unsubstituted heteroalkyl, unsubstituted aryl, aryl substituted with 1-3 halogens, unsubstituted C$_{1-8}$ alkyl, C$_{1-8}$ alkoxy or C$_{1-8}$ thioalkoxy groups, or unsubstituted aryl-C$_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. The term "acyl" as used by itself or as part of another group refers to an alkyl group wherein two substitutents on the carbon that is closest to the point of attachment for the group is replaced with the substitutent =O (e.g., —C(O)CH$_3$, —C(O)CH$_2$CH$_2$OR' and the like).

Similarly, substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro(C$_1$-C$_4$)alkoxy, and perfluoro(C$_1$-C$_4$)alkyl, in a number ranging from zero to the total number of open valences on the aromatic ring system; and where R', R" and R'" are independently selected from hydrogen, C$_{1-8}$ alkyl, C$_{3-6}$ cycloalkyl, C$_{2-8}$ alkenyl, C$_{2-8}$ alkynyl, unsubstituted aryl and heteroaryl, (unsubstituted aryl)-C$_{1-4}$ alkyl, and unsubstituted aryloxy-C$_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

As used herein, the term "heteroatom" is meant to include oxygen (O), nitrogen (N), sulfur (S) and silicon (Si).

As used herein the term "macrocycle" refers to a cyclic chemical structure having 12 to 20 atoms as ring vertices. Suitable ring vertices include carbon, nitrogen, oxygen, and sulfur. Macrocyclic rings may include one or more ring structures such as a phenyl, cycloalkyl, heteroaryl, or heterocycloalkyl group. When assigning a size of the macrocyclic ring, excocyclic atoms are not included in the determination. For example when a pyridine with meta linkages comprise part of the macrocyclic ring, only the three atoms that act as ring vertices in the macroclic ring are included.

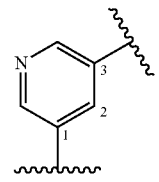 [SMILES: *c1cncc(*)c1]

Similarly, when a phenyl ring with ortho linkages comprises part of the macrocyclic ring, only the two atoms that acts as ring vertices in the macrocyclic ring are included.

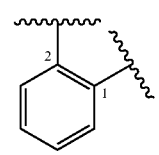 [SMILES: *c1ccccc1*]

The term "natural amino acid" refers to the 20 common naturally occurring amino acids as well as selenocystine or pyrrolosine.

The term "non-natural amino acid" refers to an amino acid that has a modified alpha carbon substituent such that it is not one of the naturally occurring amino acids. In some embodiments non-natural amino acids have an alpha carbon substituent selected from the group consisting of C$_{2-4}$ hydroxyalkyl, C$_{1-3}$ alkyl-guanidinyl, and C$_{1-4}$ alkyl-heteroaryl.

The terms "patient" and "subject" include primates (especially humans), domesticated companion animals (such as dogs, cats, horses, and the like) and livestock (such as cattle, pigs, sheep, and the like).

As used herein, the term "treating" or "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms).

The term "pharmaceutically acceptable salts" is meant to include salts of the active compounds which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

Certain compounds of the present disclosure can exist in unsolvated forms as well as solvated forms, including hydrated forms. In general, the solvated forms are equivalent to unsolvated forms and are intended to be encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer to the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are intended to be encompassed within the scope of the present disclosure. For example, the compounds may be prepared such that any number of hydrogen atoms are replaced with a deuterium ($^2$H) isotope. The compounds of the present disclosure may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. For instance, isotopic variants of the compounds of the disclosure may find additional utility, including but not limited to, as diagnostic and/or imaging reagents, or as cytotoxic/radiotoxic therapeutic agents. Additionally, isotopic variants of the compounds of the disclosure can have altered pharmacokinetic and pharmacodynamic characteristics which can contribute to enhanced safety, tolerability or efficacy during treatment. All isotopic variations of the compounds of the present disclosure, whether radioactive or not, are intended to be encompassed within the scope of the present disclosure.

Compounds

In one aspect, the present disclosure provides compounds having Formula (I) or (II):

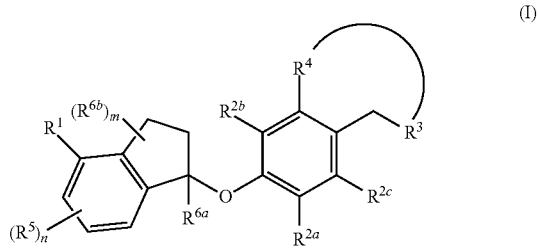

(I)

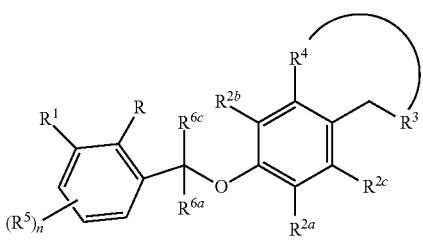

(II)

or a pharmaceutically acceptable salt thereof, wherein:

R is selected from the group consisting of H, halogen, CN, $C_{1-3}$ haloalkyl, $C_{1-3}$ alkyl and $C_{1-3}$ alkoxy;

$R^1$ is selected from the group consisting of halogen, $C_{5-8}$ cycloalkyl, $C_{6-10}$ aryl and thienyl, wherein the $C_{6-10}$ aryl and thienyl are optionally substituted with 1 to 5 $R^{1a}$ substituents;

each $R^{1a}$ is independently selected from the group consisting of halogen, —CN, —$R^c$, —$CO_2R^a$, —$CONR^aR^b$, —C(O)$R^a$, —OC(O)$NR^aR^b$, —$NR^bC(O)R^a$, —$NR^bC(O)_2R^c$, —$NR^a$—C(O)$NR^aR^b$, —$NR^aR^b$, —$OR^a$, —O—$X^1$—$OR^a$, —O—$X^1$—$CO_2R^a$, —O—$X^1$—$CONR^aR^b$, —$X^1$—$OR^a$, —$X^1$—$NR^aR^b$, —$X^1$—$CO_2R^a$, —$X^1$—$CONR^aR^b$, —$SF_5$, and —$S(O)_2NR^aR^b$, wherein each $X^1$ is a $C_{1-4}$ alkylene; each $R^a$ and $R^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, wherein the five or six-membered ring is optionally substituted with oxo; each $R^c$ is independently selected from the group consisting of $C_{1-8}$ alkyl, $C_{2-8}$ alkenyl, $C_{2-8}$ alkynyl and $C_{1-8}$ haloalkyl; and optionally when two $R^{1a}$ substituents are on adjacent atoms, they are combined to form a fused five, six or seven-membered carbocyclic or heterocyclic ring optionally substituted with from 1 to 3 substituents independently selected from halogen, oxo, $C_{1-8}$ haloalkyl and $C_{1-8}$ alkyl; or $R^1$ is

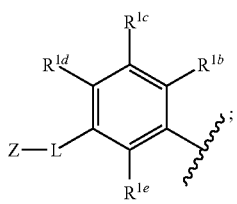

wherein each of $R^{1b}$, $R^{1c}$, $R^{1d}$ and $R^{1e}$ is independently selected from the group consisting of H, halogen, $CF_3$, CN, $C_{1-4}$ alkyl and —O—$C_{1-4}$ alkyl, wherein the $C_{1-4}$ alkyl and —O—$C_{1-4}$ alkyl are optionally further substituted with halogen, hydroxyl, methoxy or ethoxy;

L is a linking group selected from the group consisting of:

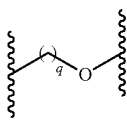

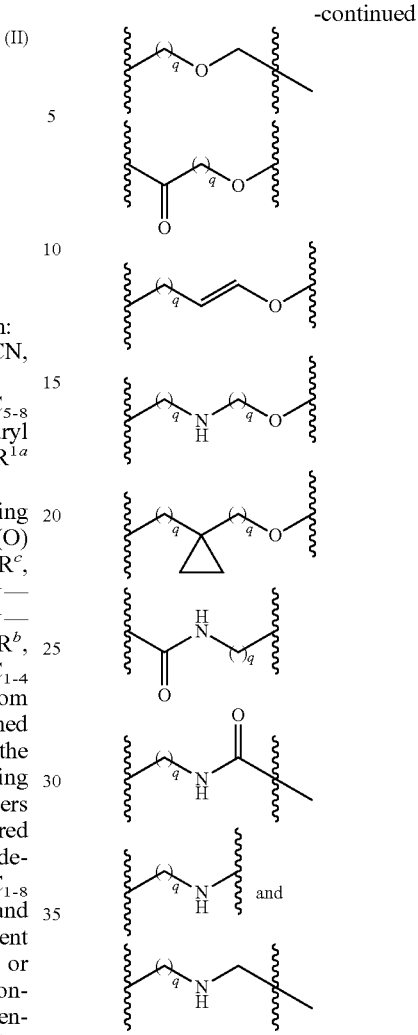

wherein each of the subscripts q is independently 1, 2, 3 or 4, and L is optionally further substituted with one or two members selected from the group consisting of halogen, hydroxy, $C_{1-3}$ alkyl, —O—$C_{1-3}$ alkyl, $C_{1-3}$ hydroxyalkyl, $C_{1-3}$ haloalkyl and —$CO_2H$;

Z is selected from the group consisting of azetidinyl, pyrolidinyl, piperidinyl, morpholinyl, pyridyl, pyrimidinyl, guanidinyl, quinuclidine, and 8-azabicyclo[3.2.1]octane, each of which is optionally substituted with from 1 to 3 groups independently selected from halogen, hydroxy, $C_{1-3}$ alkyl, —$NH_2$, —$NHC_{1-3}$alkyl, —$N(C_{1-3}$alkyl$)_2$, —O—$C_{1-3}$ alkyl, $C_{1-3}$ hydroxyalkyl, $C_{1-3}$ haloalkyl and —$CO_2H$;

or

Z is selected from the group consisting of —$CO_2R^{z1}$ and —$NR^{z1}R^{z2}$; wherein $R^{z1}$ is selected from the group consisting of H, $C_{1-8}$ alkyl, $C_{1-8}$ haloalkyl and $C_{1-8}$ hydroxyalkyl; and $R^{z2}$ is selected from —$C_{1-8}$ alkyl, $C_{1-8}$ haloalkyl, $C_{1-8}$ alkyl-COOH, $C_{1-8}$ alkyl-OH, $C_{1-8}$ alkyl-$CONH_2$, $C_{1-8}$ alkyl-$SO_2NH_2$, $C_{1-8}$ alkyl-$PO_3H_2$, $C_{1-8}$ alkyl-C(O)NHOH, —C(O)—$C_{1-8}$alkyl-OH, —C(O)—$C_{1-8}$alkyl-COOH, $C_{3-10}$ cycloalkyl, —$C_{3-10}$ cycloalkyl-COOH, —$C_{3-10}$ cycloalkyl-OH, $C_{4-8}$ heterocyclyl, —$C_{4-8}$ heterocyclyl-COOH, —$C_{4-8}$ heterocyclyl-OH, —$C_{1-8}$ alkyl-$C_{4-8}$ heterocyclyl, —$C_{1-8}$ alkyl-$C_{3-10}$ cycloalkyl, $C_{5-10}$ heteroaryl and —$C_{1-8}$alkyl-$C_{5-10}$ heteroaryl;

each $R^{2a}$, $R^{2b}$ and $R^{2c}$ is independently selected from the group consisting of H, halogen, —CN, —$R^d$, —$CO_2R^e$, —$CONR^eR^f$, —$OC(O)NR^eR^f$, —$NR^fC(O)R^e$, —$NR^fC(O)_2R^d$, —$NR^e$—$C(O)NR^eR^f$, —$NR^eR^f$, —$OR^e$, —$X^2$—$OR^e$, —$X^2$—$NR^eR^f$, —$X^2$—$CO_2R^e$, —$SF_5$, and —$S(O)_2NR^eR^f$, wherein each $X^2$ is a $C_{1-4}$ alkylene; each $R^e$ and $R^f$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O and S, and optionally substituted with oxo; each $R^d$ is independently selected from the group consisting of $C_{1-8}$ alkyl, $C_{2-8}$ alkenyl, and $C_{1-8}$ haloalkyl;

$R^3$ is selected from the group consisting of —$NR^gR^h$ and $C_{4-12}$ heterocyclyl, wherein the $C_{4-12}$ heterocyclyl is optionally substituted with 1 to 6 $R^{3a}$;

each $R^{3a}$ is independently selected from the group consisting of halogen, —CN, —$R^i$, —$CO_2R^i$, —$CONR^jR^k$, —$CONHC_{1-6}$ alkyl-OH, —$C(O)R^j$, —$OC(O)NR^jR^k$, —$NR^jC(O)R^k$, —$NR^jC(O)_2R^k$, —CONHOH, —$PO_3H_2$, —$NR^j$—$X^3$—$C(O)_2R^k$, —$NR^jC(O)NR^jR^k$, —$NR^jR^k$, —$OR^j$, —$S(O)_2NR^jR^k$, —$O$—$X^3$—$OR^j$, —$O$—$X^3$—$NR^jR^k$, —$O$—$X^3$—$CO_2R^j$, —$O$—$X^3$—$CONR^jR^k$, —$X^3$—$OR^j$, —$X^3$—$NR^jR^k$, —$X^3$—$CO_2R^j$, —$X^3$—$CONR^jR^k$, —$X^3$—$CONHSO_2R^j$ and $SF_5$; wherein $X^3$ is $C_{1-6}$ alkylene and is optionally further substituted with OH, $SO_2NH_2$, $CONH_2$, $C(O)NHOH$, $PO_3H_2$, $COO$—$C_{1-6}$ alkyl or $CO_2H$, wherein each $R^j$ and $R^k$ is independently selected from hydrogen, $C_{1-8}$ alkyl optionally substituted with 1 to 2 substituents selected from OH, $SO_2NH_2$, $CONH_2$, $C(O)NHOH$, $PO_3H_2$, $B(OH)_2$, $COO$—$C_{1-8}$alkyl or $CO_2H$, and $C_{1-8}$ haloalkyl optionally substituted with 1 to 2 substituents selected from OH, $SO_2NH_2$, $CONH_2$, $C(O)NHOH$, $PO_3H_2$, $COO$—$C_{1-8}$alkyl or $CO_2H$, or when attached to the same nitrogen atom $R^j$ and $R^k$ can be combined with the nitrogen atom to form a five or six-membered ring having from 0 to 2 additional heteroatoms as ring members selected from N, O or S, and optionally substituted with oxo; each $R^i$ is independently selected from the group consisting of $C_{1-8}$ alkyl, $C_{2-8}$ alkenyl, and $C_{1-8}$ haloalkyl each of which may be optionally substituted with OH, $SO_2NH_2$, $CONH_2$, $C(O)NHOH$, $PO_3H_2$, $COO$—$C_{1-8}$alkyl or $CO_2H$;

$R^g$ is selected from the group consisting of H, $C_{1-8}$ haloalkyl and $C_{1-8}$ alkyl;

$R^h$ is selected from $C_{1-8}$ alkyl, $C_{1-8}$ haloalkyl, $C_{1-8}$ hydroxyalkyl, $C_{1-8}$alkyl-$CO_2R^j$, $C_{1-8}$alkyl-$CONR^jR^k$, $C_{1-8}$alkyl-$CONHSO_2R^j$, $C_{1-8}$ alkyl-$SO_2NR^jR^k$, $C_{1-8}$ alkyl-$PO_3H_2$, $C_{1-8}$ alkyl-$C(O)NHOH$, $C_{1-8}$ alkyl-$NR^jR^k$, —$C(O)R^j$, $C_{3-10}$ cycloalkyl, —$C_{3-10}$ cycloalkyl-$COOR^j$, —$C_{3-10}$ cycloalkyl-$OR^j$, $C_{4-8}$ heterocyclyl, —$C_{4-8}$ heterocyclyl-$COOR^j$, —$C_{4-8}$ heterocyclyl-$OR^j$, —$C_{1-8}$ alkyl-$C_{4-8}$ heterocyclyl, —$C(=O)OC_{1-8}$ alkyl-$C_{4-8}$ heterocyclyl, —$C_{1-8}$ alkyl-$C_{3-10}$ cycloalkyl, $C_{5-10}$ heteroaryl, —$C_{1-8}$alkyl-$C_{5-10}$heteroaryl, —$C_{1-8}$ alkyl-$C_{6-10}$ aryl, —$C_{1-8}$ alkyl-(C=O)—$C_{6-10}$ aryl, —$CO_2$—$C_{1-8}$ alkyl-$O_2C$—$C_{1-8}$ alkyl, —$C_{1-8}$ alkyl-NH(C=O)—$C_{2-8}$ alkenyl, —$C_{1-8}$ alkyl-NH(C=O)—$C_{1-8}$ alkyl, —$C_{1-8}$ alkyl-NH(C=O)—$C_{2-8}$ alkynyl, —$C_{1-8}$ alkyl-(C=O)—NH—$C_{1-8}$ alkyl-CO-$OR^j$, and —$C_{1-8}$ alkyl-(C=O)—NH—$C_{1-8}$ alkyl-OR optionally substituted with $CO_2H$; or $R^h$ combined with the N to which it is attached is a mono-, di- or tri-peptide comprising 1-3 natural amino acids and 0-2 non-natural amino acids, wherein the non-natural aminoacids have an alpha carbon substituent selected from the group consisting of $C_{2-4}$ hydroxyalkyl, $C_{1-3}$ alkyl-guanidinyl, and $C_{1-4}$ alkyl-heteroaryl, the alpha carbon of each natural or non-natural amino acid is optionally further substituted with a methyl group, and the terminal moiety of the mono-, di-, or tri-peptide is selected from the group consisting of C(O)OH, C(O)O—$C_{1-6}$ alkyl, and $PO_3H_2$, wherein the $C_{1-8}$ alkyl portions of $R^h$ are optionally further substituted with from 1 to 3 substituents independently selected from OH, COOH, $SO_2NH_2$, $CONH_2$, $C(O)NHOH$, COO—$C_{1-4}$ alkyl, $PO_3H_2$ and $C_{5-6}$ heteroaryl optionally substituted with 1 to 2 $C_{1-3}$ alkyl substituents, the $C_{5-10}$ heteroaryl and the $C_{6-10}$ aryl portions of $R^h$ are optionally substituted with 1 to 3 substituents independently selected from OH, $B(OH)_2$, COOH, $SO_2NH_2$, $CONH_2$, $C(O)NHOH$, $PO_3H_2$, COO—$C_{1-8}$alkyl, $C_{1-4}$alkyl, $C_{1-4}$alkyl-OH, $C_{1-4}$alkyl-$SO_2NH_2$, $C_{1-4}$alkyl $CONH_2$, $C_{1-4}$alkyl-$C(O)NHOH$, $C_{1-4}$alkyl-$PO_3H_2$, $C_{1-4}$alkyl-COOH, and phenyl;

the $C_{4-8}$ heterocyclyl and $C_{3-10}$ cycloalkyl portions of $R^h$ are optionally substituted with 1 to 4 $R^{h1}$ substituents;

each $R^{h1}$ substituent is independently selected from $C_{1-4}$ alkyl, $C_{1-4}$ alkyl-OH, $C_{1-4}$ alkyl-COOH, $C_{1-4}$ alkyl-$SO_2NH_2$, $C_{1-4}$ alkyl $CONH_2$, $C_{1-4}$ alkyl-$C(O)NHOH$, $C_{1-4}$ alkyl-$PO_3H$, OH, COO—$C_{1-8}$ alkyl, COOH, $SO_2NH_2$, $CONH_2$, $C(O)NHOH$, $PO_3H_2$, $B(OH)_2$ and oxo;

$R^4$ is selected from the group consisting of O—$C_{1-8}$ alkyl, O—$C_{1-8}$ haloalkyl, $C_{6-10}$ aryl, $C_{5-10}$ heteroaryl, —O—$C_{1-4}$ alkyl-$C_{4-7}$ heterocycloalkyl, —O—$C_{1-4}$ alkyl-$C_{6-10}$aryl and —O—$C_{1-4}$ alkyl-$C_{5-10}$ heteroaryl, each of which is optionally substituted with 1 to 5 $R^{4a}$;

each $R^{4a}$ is independently selected from the group consisting of halogen, —CN, —$R^m$, —$CO_2R^n$, —$CONR^nR^p$, —$C(O)R^n$, —$OC(O)NR^nR^p$, —$NR^nC(O)R^p$, —$NR^nC(O)_2R^m$, —$NR^n$—$C(O)NR^nR^p$, —$NR^nR^p$, —$OR^n$, —$O$—$X^4$—$OR^n$, —$O$—$X^4$—$NR^nR^p$, —$O$—$X^4$—$CO_2R^n$, —$O$—$X^4$—$CONR^nR^p$, —$X^4$—$OR^n$, —$X^4$—$NR^nR^p$, —$X^4$—$CO_2R^n$, —$X^4$—$CONR^nR^p$, —$SF_5$, —$S(O)_2R^nR^p$, —$S(O)_2NR^nR^p$, $C_{3-7}$ cycloalkyl and $C_{4-7}$ heterocycloalkyl, wherein the cycloalkyl and heterocycloalkyl rings are optionally substituted with 1 to 5 $R^t$, wherein each $R^t$ is independently selected from the group consisting of $C_{1-8}$ alkyl, $C_{1-8}$haloalkyl, —$CO_2R^n$, —$CONR^nR^p$, —$C(O)R^n$, —$OC(O)NR^nR^p$, —$NR^nC(O)R^p$, —$NR^nC(O)_2R^m$, —$NR^n$—$C(O)NR^nR^p$, —$NR^nR^p$, —$OR^n$, —$O$—$X^4$—$OR^n$, —$O$—$X^4$—$NR^nR^p$, —$O$—$X^4$—$CO_2R^n$, —$O$—$X^4$—$CONR^nR^p$, —$X^4$—$OR^n$, —$X^4$—$NR^nR^p$, —$X^4$—$CO_2R^n$, —$X^4$—$CONR^nR^p$, —$SF_5$, and —$S(O)_2NR^nR^p$;

wherein each $X^4$ is a $C_{1-6}$ alkylene; each $R^n$ and $R^p$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; each $R^m$ is independently selected from the group consisting of $C_{1-8}$ alkyl, $C_{2-8}$ alkenyl, and $C_{1-8}$ haloalkyl; and optionally when two $R^{4a}$ substituents are on adjacent atoms, they are combined to form a fused five or six-membered carbocyclic or heterocyclic ring optionally substituted with oxo;

and wherein $R^3$ and $R^4$ are joined to form a 12- to 20-membered macrocycle;

n is 0, 1, 2 or 3;

each $R^5$ is independently selected from the group consisting of halogen, —CN, —$R^q$, —$CO_2R^r$, —$CONR^rR^s$, —C(O)$R^r$, —OC(O)$NR^rR^s$, —$NR^rC(O)R^s$, —$NR^rC(O)_2R^q$, —$NR^r$—C(O)$NR^rR^s$, —$NR^rR^s$, —$OR^r$, —O—$X^5$—$OR^r$, —O—$X^5$—$NR^rR^s$, —O—$X^5$—$CO_2R^r$, —O—$X^5$—$CONR^rR^s$, —$X^5$—$OR^r$, —$X^5$—$NR^rR^s$, —$X^5$—$CO_2R^r$, —$X^5$—$CONR^rR^s$, —$SF_5$, —$S(O)_2NR^rR^s$, wherein each $X^5$ is a $C_{1-4}$ alkylene; each $R^r$ and $R^s$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; each $R^q$ is independently selected from the group consisting of $C_{1-8}$ alkyl, and $C_{1-8}$ haloalkyl;

$R^{6a}$ and $R^{6c}$ are each independently selected from the group consisting of H, $C_{1-4}$ alkyl and $C_{1-4}$ haloalkyl;

m is 0, 1, 2, 3 or 4;

each $R^{6b}$ is independently selected from the group consisting of F, $C_{1-4}$ alkyl, O—$R^u$, $C_{1-4}$ haloalkyl, $NR^uR^v$, wherein each $R^u$ and $R^v$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo.

$R^3$ and $R^4$ are joined by forming a bond between atoms of each substituent. In some embodiments, $R^3$ is $NR^gR^h$ where $R^h$ an amino acid and $R^h$ is linked to $R^4$ by the alpha carbon substituent of the amino acid. In some embodiments, $R^3$ is $NR^gR^h$ where $R^h$ is an amino acid and $R^h$ is linked to $R^4$ by the carboxylic acid substituent. In some embodiments, $R^4$ is —O—$C_{1-4}$ alkyl-$C_{5-10}$ heteroaryl and $R^4$ is optionally substituted with $R^{4a}$, where $R^{4a}$ is —$CONR^nR^p$, $R^p$ is $C_{1-8}$ alkyl, and $R^p$ is linked to $R^3$ by the $C_{1-8}$ alkyl moiety.

In some embodiments, compounds are provided having Formula (I). In other embodiments, compounds are provided having Formula (II).

In some embodiments, the present disclosure provides compounds having Formula (Ia) or (IIa):

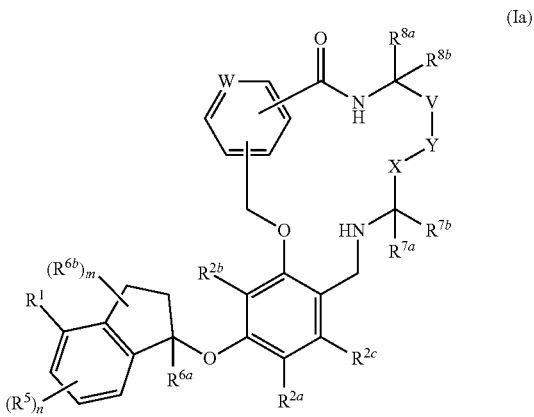

(Ia)

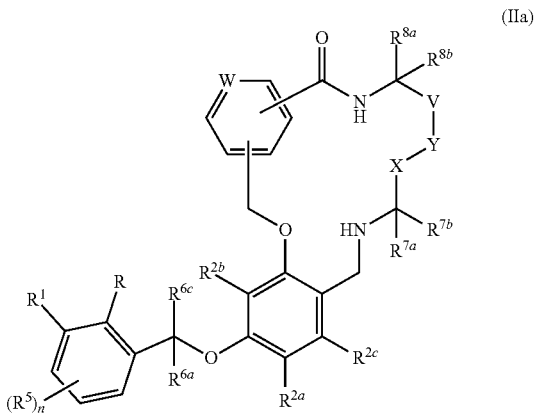

(IIa)

or a pharmaceutically acceptable salt thereof; wherein:

W is N or C($R^9$);

X, Y and V are each independently selected from the group consisting of a bond, O, NH, N(CH$_3$), C(O), methylene and ethylene, wherein the methylene and ethylene are optionally substituted with one or two $R^{7a}$;

$R^1$ is selected from the group consisting of $C_{6-10}$ aryl and thienyl, each of which is optionally substituted with 1 to 5 $R^{1a}$ substituents;

each $R^{7a}$ and $R^{7b}$ is independently selected from the group consisting of H, $C_{1-6}$ alkyl, $CO_2H$, —$CO_2$—($C_{1-6}$alkyl) and $PO_3H_2$, wherein $C_{1-6}$ alkyl is optionally substituted with one or two members selected from halogen, OH, NH$_2$, CN, and $CO_2H$;

each $R^{8a}$ and $R^{8b}$ is independently selected from the group consisting of H and $C_{1-6}$ alkyl, optionally substituted with halogen, OH, NH$_2$, CN, and $CO_2H$; and $R^9$ a member selected from the group consisting of H, halogen, CN, $C_{1-6}$ alkyl, —O—$C_{1-6}$ alkyl, —$SO_2$($C_{1-6}$ alkyl), —$C_{1-6}$ alkyl-$CO_2H$, —$C_{1-6}$ alkyl-$CO_2$—$C_{1-6}$ alkyl, —$C_{1-6}$ alkyl-C(O)NH$_2$, —$C_{1-6}$ alkyl-C(O)NH$C_{1-6}$ alkyl and —$C_{1-6}$ alkyl-C(O)N($C_{1-6}$ alkyl)$_2$, and the remaining groups have the meanings provided with reference to Formula (I) and (II) above.

In some embodiments, compounds are provided having Formula (Ia). In other embodiments, compounds are provided having Formula (IIa).

In some embodiments, the compound, or a pharmaceutically acceptable salt thereof is a compound of Formula (I), (II), (Ia) or (IIa), wherein the macrocycle formed by joining $R^3$ and $R^4$ (or by having X, Y and V as ring members) is a 12-membered, a 13-membered, a 14-membered, a 15-membered, a 16-membered, a 17-membered, a 18-membered, a 19-membered, or a 20-membered macrocycle.

In some embodiments, compounds of Formula (Ib) or Formula (IIb) are provided:

In some embodiments, compounds of Formula (Ic) or Formula (IIc) are provided:

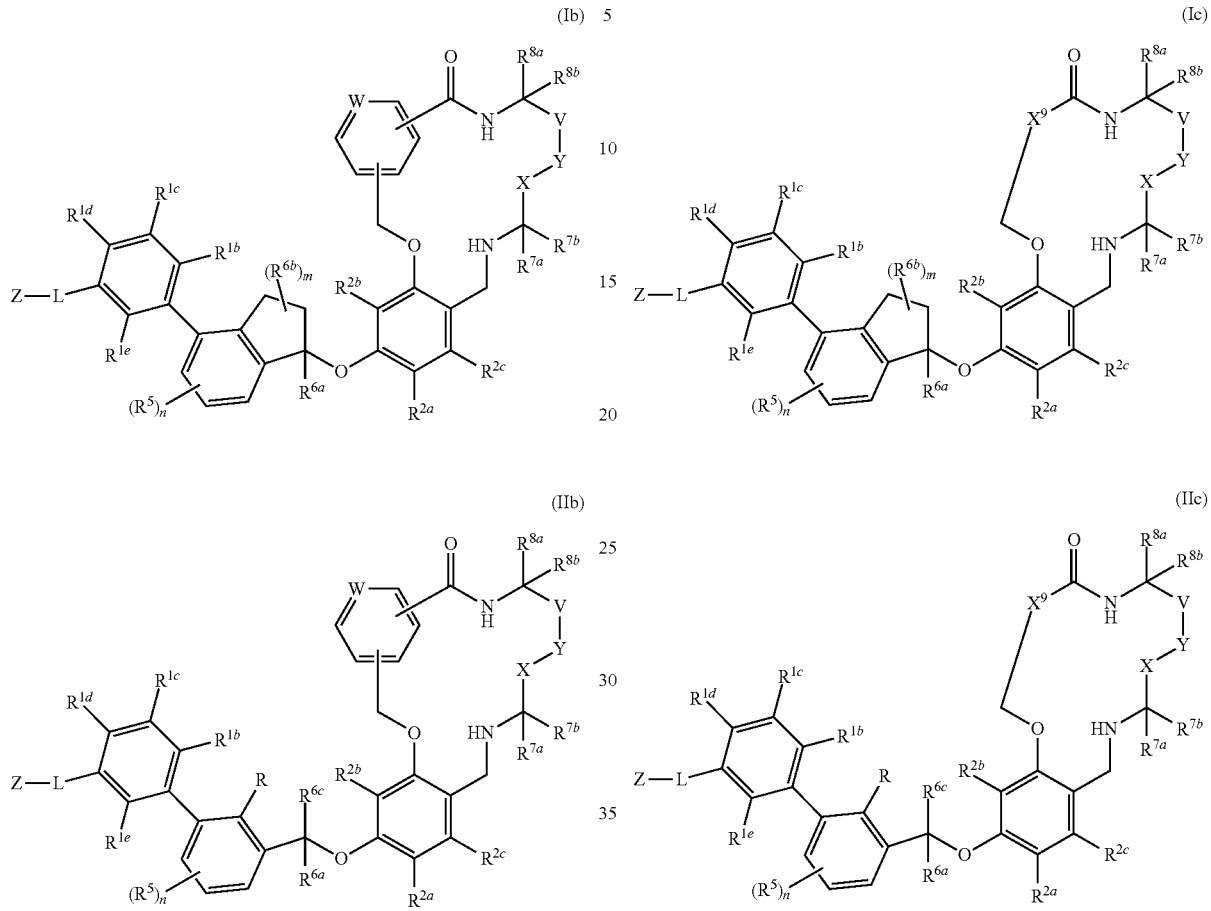

or a pharmaceutically acceptable salt thereof; wherein:

W is N or C(R$^9$);

X, Y and V are each independently selected from the group consisting of a bond, O, NH, N(CH$_3$), C(O), methylene and ethylene, wherein the methylene and ethylene are optionally substituted with one or two R$^{7a}$;

each R$^{7a}$ and R$^{7b}$ is independently selected from the group consisting of H, C$_{1-6}$ alkyl, CO$_2$H, CH$_2$OH, —CO$_2$—(C$_{1-6}$ alkyl) and PO$_3$H$_2$, wherein C$_{1-6}$ alkyl is optionally substituted with one or two members selected from halogen, OH, NH$_2$, CN, and CO$_2$H;

each R$^{8a}$ and R$^{8b}$ is independently selected from the group consisting of H and C$_{1-6}$ alkyl, optionally substituted with halogen, OH, NH$_2$, CN, and CO$_2$H; and R$^9$ a member selected from the group consisting of H, halogen, CN, C$_{1-6}$ alkyl, —O—C$_{1-6}$ alkyl, —SO$_2$(C$_{1-6}$ alkyl), —C$_{1-6}$ alkyl-CO$_2$H, —C$_{1-6}$ alkyl-CO$_2$—C$_{1-6}$ alkyl, —C$_{1-6}$ alkyl-C(O)NH$_2$, —C$_{1-6}$ alkyl-C(O)NHC$_{1-6}$ alkyl and —C$_{1-6}$ alkyl-C(O)N(C$_{1-6}$ alkyl)$_2$, and the remaining groups have the meanings provided with reference to Formula (I) and (II) above.

In some embodiments, compounds are provided having Formula (Ib). In other embodiments, compounds are provided having Formula (IIb).

or a pharmaceutically acceptable salt thereof; wherein:

X$^9$ is C$_{1-8}$ alkylene;

X, Y and V are each independently selected from the group consisting of a bond, O, NH, N(CH$_3$), C(O), methylene and ethylene, wherein the methylene and ethylene are optionally substituted with one or two R$^{7a}$;

each R$^{7a}$ and R$^{7b}$ is independently selected from the group consisting of H, C$_{1-6}$ alkyl, CO$_2$H, CH$_2$OH, —CO$_2$—(C$_{1-6}$ alkyl) and PO$_3$H$_2$, wherein C$_{1-6}$ alkyl is optionally substituted with one or two members selected from halogen, OH, NH$_2$, CN, and CO$_2$H; and each R$^{8a}$ and R$^{8b}$ is independently selected from the group consisting of H and C$_{1-6}$ alkyl, optionally substituted with halogen, OH, NH$_2$, CN, and CO$_2$H and the remaining groups have the meanings provided with reference to Formula (I) and (II) above.

In some embodiments, compounds are provided having Formula (Ic). In other embodiments, compounds are provided having Formula (IIc).

In some embodiments, compounds of Formula (Ia1) and Formula (IIa1) are provided:

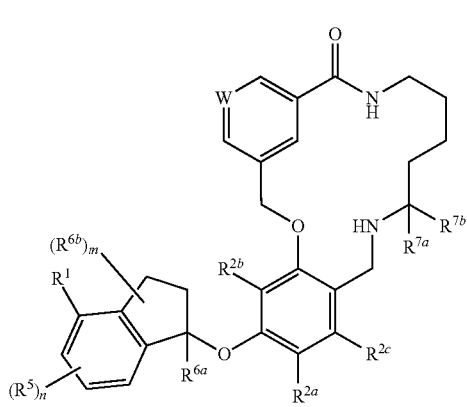
(Ia1)

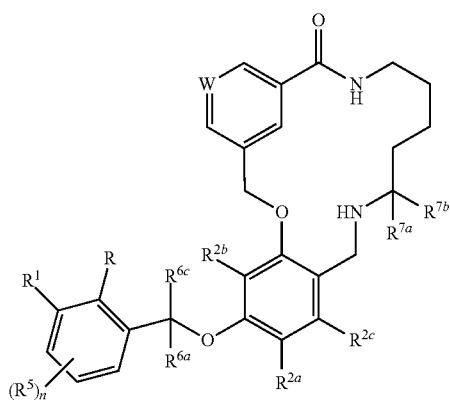
(IIa1)

or a pharmaceutically acceptable salt thereof; wherein:

W is N or C($R^9$);

$R^1$ is selected from the group consisting of $C_{6-10}$ aryl and thienyl, each of which is optionally substituted with 1 to 5 $R^{1a}$ substituents;

each $R^{7a}$ and $R^{7b}$ is independently selected from the group consisting of H, $C_{1-6}$ alkyl, $CO_2H$, $CH_2OH$, —$CO_2$—($C_{1-6}$ alkyl) and $PO_3H_2$, wherein $C_{1-6}$ alkyl is optionally substituted with one or two members selected from halogen, OH, $NH_2$, CN, and $CO_2H$; and $R^9$ a member selected from the group consisting of H, halogen, CN, $C_{1-6}$ alkyl, —O—$C_{1-6}$ alkyl, —$SO_2$($C_{1-6}$ alkyl), —$C_{1-6}$ alkyl-$CO_2H$, —$C_{1-6}$ alkyl-$CO_2$—$C_{1-6}$ alkyl, —$C_{1-6}$ alkyl-C(O)$NH_2$, —$C_{1-6}$ alkyl-C(O)NH$C_{1-6}$ alkyl and —$C_{1-6}$ alkyl-C(O)N($C_{1-6}$ alkyl)$_2$, and the remaining groups have the meanings provided with reference to Formula (I) and (II) above.

In some embodiments, compounds are provided having Formula (Ia1). In other embodiments, compounds are provided having Formula (IIa1).

In some embodiments, compounds of Formula (Ib1) and Formula (IIb1) are provided:

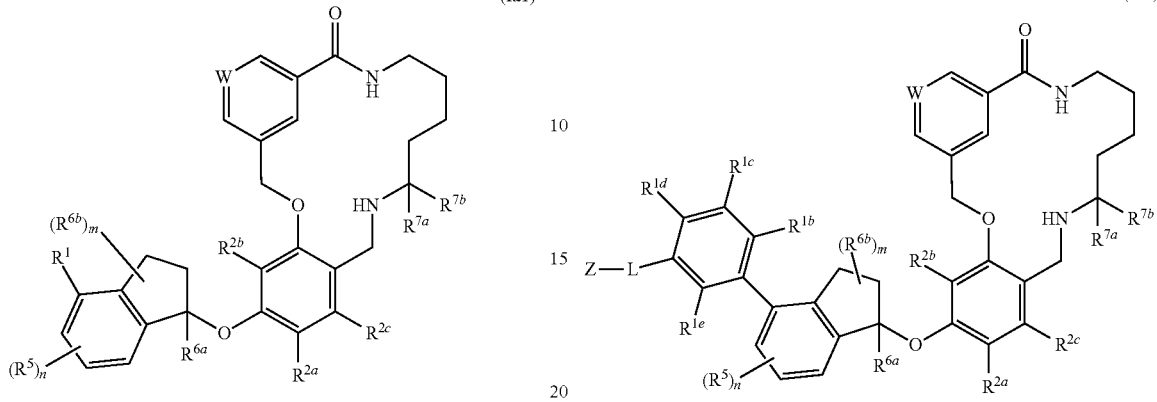
(Ib1)

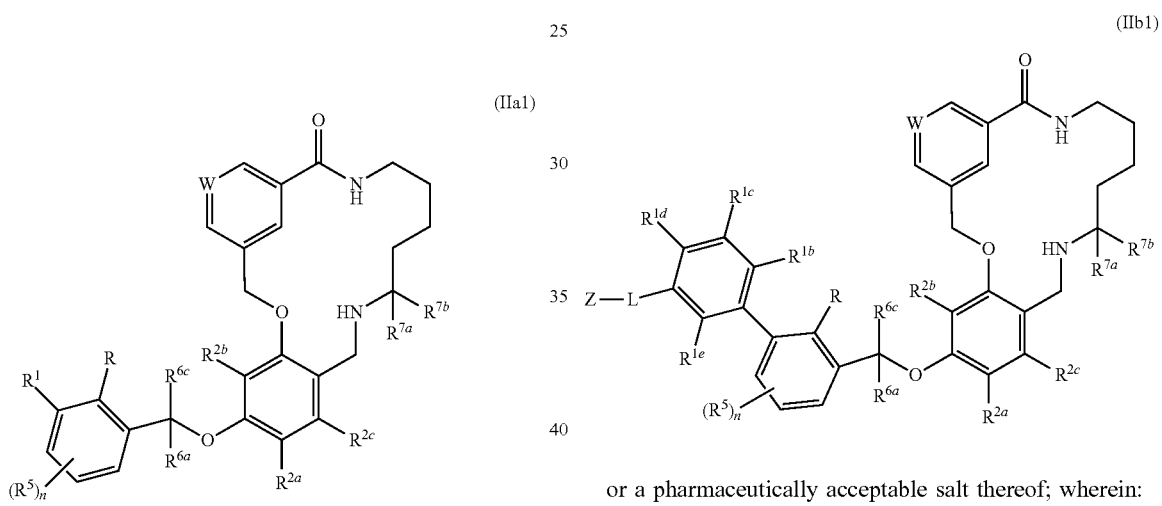
(IIb1)

or a pharmaceutically acceptable salt thereof; wherein:

W is N or C($R^9$);

each $R^{7a}$ and $R^{7b}$ is independently selected from the group consisting of H, $C_{1-6}$ alkyl, $CO_2H$, —$CO_2$—($C_{1-6}$alkyl) and $PO_3H_2$, wherein $C_{1-6}$ alkyl is optionally substituted with one or two members selected from halogen, OH, $NH_2$, CN, and $CO_2H$;

$R^9$ a member selected from the group consisting of H, halogen, CN, $C_{1-6}$ alkyl, —O—$C_{1-6}$ alkyl, —$SO_2$($C_{1-6}$ alkyl), —$C_{1-6}$ alkyl-$CO_2H$, —$C_{1-6}$ alkyl-$CO_2$—$C_{1-6}$ alkyl, —$C_{1-6}$ alkyl-C(O)$NH_2$, —$C_{1-6}$ alkyl-C(O)NH$C_{1-6}$ alkyl and —$C_{1-6}$ alkyl-C(O)N($C_{1-6}$ alkyl)$_2$, and the remaining groups have the meanings provided with reference to Formula (I) and (II) above.

In some embodiments, compounds are provided having Formula (Ib1). In other embodiments, compounds are provided having Formula (IIb1).

In some embodiments, compounds of Formula (Ic1) and Formula (IIc1) are provided:

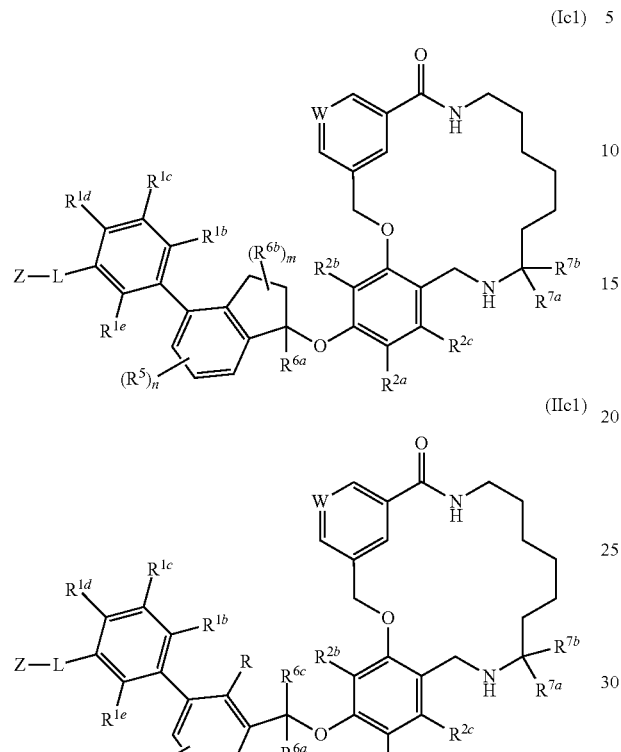

or a pharmaceutically acceptable salt thereof; wherein:
W is N or C(R$^9$);
each R$^{7a}$ and R$^{7b}$ is independently selected from the group consisting of H, C$_{1-6}$ alkyl, CO$_2$H, CH$_2$OH, —CO$_2$—(C$_{1-6}$ alkyl) and PO$_3$H$_2$, wherein C$_{1-6}$ alkyl is optionally substituted with one or two members selected from halogen, OH, NH$_2$, CN, and CO$_2$H;
R$^9$ a member selected from the group consisting of H, halogen, CN, C$_{1-6}$ alkyl, —O—C$_{1-6}$ alkyl, —SO$_2$(C$_{1-6}$ alkyl), —C$_{1-6}$ alkyl-CO$_2$H, —C$_{1-6}$ alkyl-CO$_2$—C$_{1-6}$ alkyl, —C$_{1-6}$ alkyl-C(O)NH$_2$, —C$_{1-6}$ alkyl-C(O)NHC$_{1-6}$ alkyl and —C$_{1-6}$ alkyl-C(O)N(C$_{1-6}$ alkyl)$_2$
and the remaining groups have the meanings provided with reference to Formula (I) and (II) above.

In some embodiments, compounds are provided having Formula (Ic1). In other embodiments, compounds are provided having Formula (IIc1).

In some embodiments for each of Formula (I), (II), (Ia), (IIa), (Ia1) and (IIa1), R$^1$ is selected from the group consisting of phenyl and thienyl, wherein the phenyl and thienyl are optionally substituted with 1 to 5 R$^{1a}$ substituents, and in some embodiments with 1 to 3 R$^{1a}$. In some embodiments, R$^1$ is phenyl optionally substituted with 1 or 2 R$^{1a}$ substituents, wherein each R$^{1a}$ is independently selected from halogen, C$_{1-8}$ alkyl, O—C$_{1-8}$ alkyl, O—C$_{1-8}$ haloalkyl, —NR$^a$R$^b$, and CN, and optionally when two R$^{1a}$ substituents are on adjacent atoms, they are combined to form a fused six-membered heterocyclic ring optionally substituted with from 1 to 3 substituents independently selected from oxo, C$_{1-8}$ haloalkyl and C$_{1-8}$ alkyl. In some embodiments, R$^1$ is phenyl optionally substituted with F. In some embodiments, R$^1$ is selected from the group consisting of:

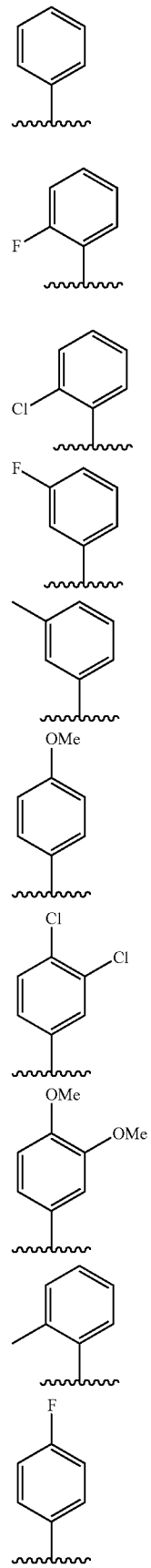

-continued
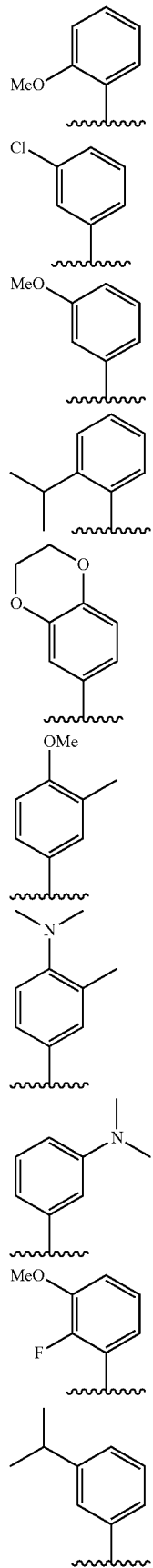
-continued
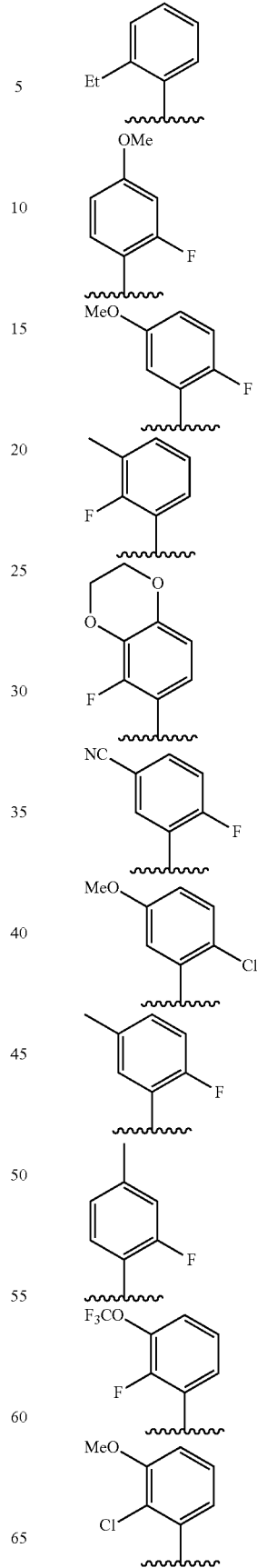

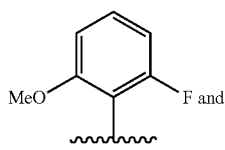
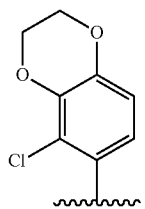
In some embodiments of Formula (I), (II), (Ib), (IIb), (Ib1) (IIb1), (Ic), (IIc), (Ic1), and (IIc1) the group Z-L- is selected from
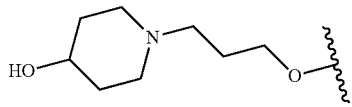
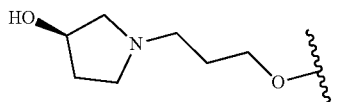
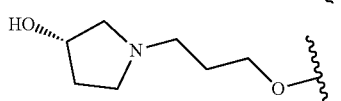
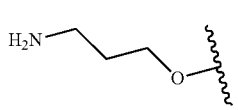
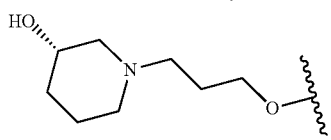
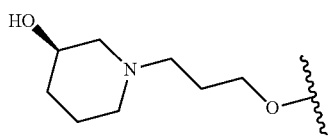
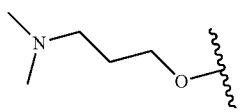
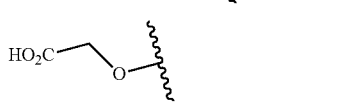
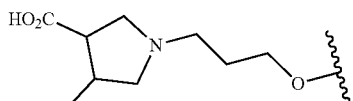
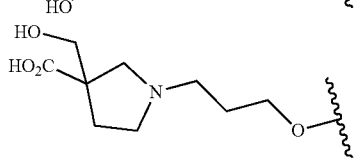
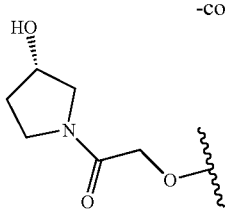
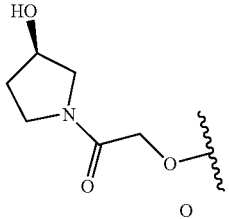
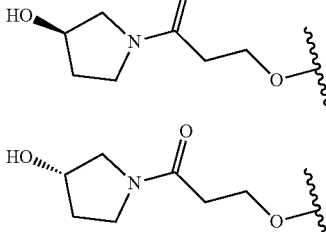
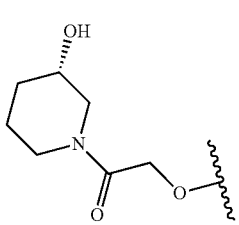
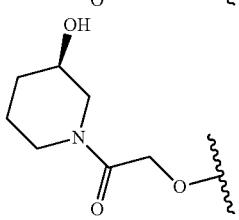
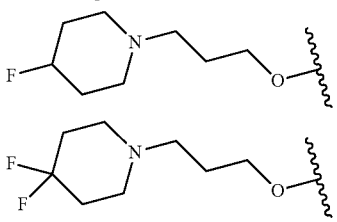
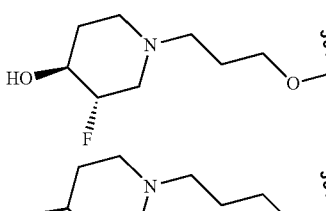
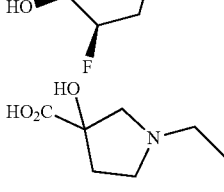

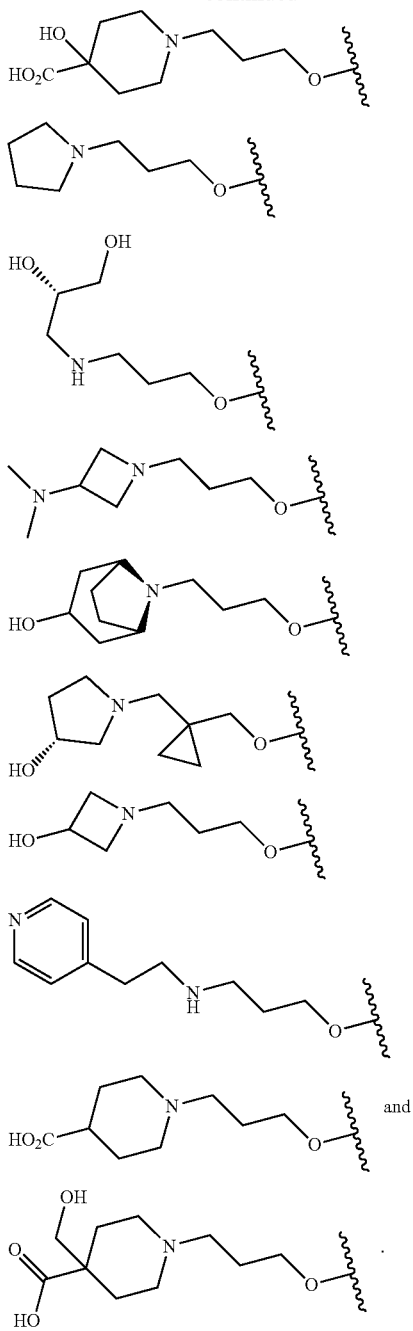

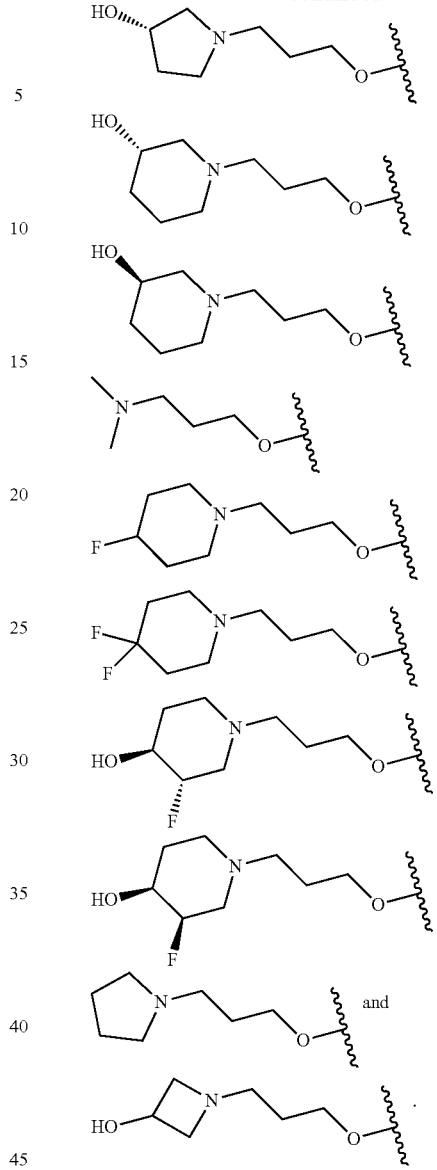

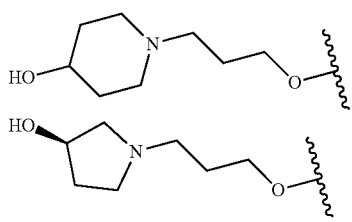

In some embodiments of Formula (I), (II), (Ib), (IIb), (Ib1), (IIb1), (Ic), (IIc), (Ic1), and (IIc1) the group Z-L- is selected from

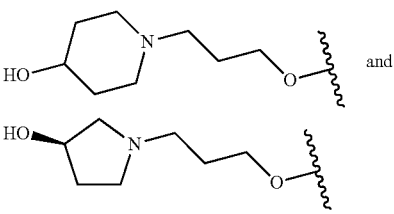

In some embodiments of Formula (I), (II), (Ib), (IIb), (Ib1), (IIb1), (Ic), (IIc), (Ic1), and (IIc1) the group Z-L- is selected from In some embodiments for each of Formula (I), (II), (Ia), (IIa), (Ia1), (IIa1), (Ib), (IIb), (Ib1), (IIb1), (Ic), (IIc), (Ic1), and (IIc1) each $R^{2a}$, $R^{2b}$ and $R^{2c}$ is independently selected from the group consisting of H, halogen, —CN, —$R^d$, —$NR^eR^f$, —$OR^e$, —$X^2$—$OR^e$, —$X^2$—$NR^eR^f$, wherein $X^2$ is $C_{1-4}$ alkylene; each $R^e$ and $R^f$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and optionally substituted with oxo; each $R^d$ is independently selected from the group consisting of $C_{1-8}$ alkyl, $C_{2-8}$ alkenyl, and $C_{1-8}$ haloalkyl. In some embodiments, $R^{2b}$ and $R^{2c}$ are both H and $R^{2a}$ is selected from the group consisting of halogen, $C_{1-4}$ alkyl, $C_{2-4}$ alkenyl, $C_{1-3}$ haloalkyl, —CN, —OMe and OEt. In some embodiments, $R^{2b}$ and $R^{2c}$ are both H and $R^{2a}$ is halogen. In some embodiments, $R^{2b}$ and $R^{2c}$ are both H and $R^{2a}$ is Cl.

In some embodiments the compound, or a pharmaceutically acceptable salt thereof is a compound of Formula (I), (II), (Ia), (IIa), (Ia1), (IIa1), (Ib), (IIb), (Ib1), (IIb1), or (Ic), (IIc), (Ic1), and (IIc1) wherein n is 0, 1 or 2 and each $R^5$ is independently selected from the group consisting of halogen, —CN, —$R^m$, —$NR^nR^p$, and —$OR^n$, wherein each $R^n$ and $R^p$ is independently selected from hydrogen, $C_{1-8}$ alkyl and $C_{1-8}$ haloalkyl and each $R^m$ is independently selected from the group consisting of $C_{1-8}$ alkyl and $C_{1-8}$ haloalkyl. In some embodiments, n is 0.

In some embodiments the compound, or a pharmaceutically acceptable salt thereof is a compound of Formula (I), (II), (Ia), (IIa), (Ia1), (IIa1), (Ib), (IIb), (Ib1), (IIb1), (Ic), (IIc), (Ic1), or (IIc1) wherein $R^{6a}$ is H. In some embodiments, m is 0. In some embodiments, m is 1 and $R^{6b}$ is selected from the group consisting of F, $C_{1-4}$ alkyl, O—$R^q$, $C_{1-4}$ haloalkyl and $NR^qR^r$, wherein each $R^q$ and $R^r$ is independently selected from hydrogen, $C_{1-8}$ alkyl, and $C_{1-8}$ haloalkyl. In some embodiments, m is 1 and $R^{6b}$ is F.

In some embodiments, $R^9$ in compounds having Formula (Ia), (IIa), (Ib), (IIb), (Ia1), (IIa1), (Ib1), (IIb1), (Ic1) and (IIc1) is CN. In some embodiments, W in compounds having Formula (Ia1), (IIa1), (Ib1), (IIb1), (Ic1) or (IIc1) is N.

In some embodiments, each $R^{7a}$ and $R^{7b}$ in compounds having Formula (Ia), (IIa), (Ib), (IIb), (Ic), (IIc), (Ia1), (IIa1), (Ib1), (IIb1), (Ic1) and (IIc1) is independently selected from the group consisting of H, $CO_2H$, and $CH_2OH$.

In some embodiments the compound, or a pharmaceutically acceptable salt thereof is a compound of Formula (I), (Ia), or (Ia1), wherein the portion shown as

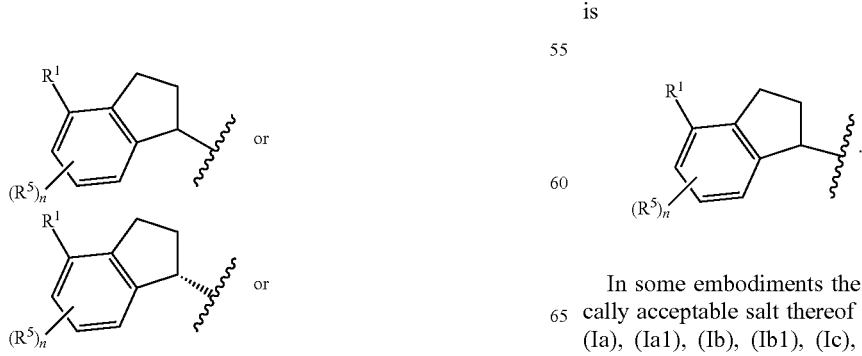

is

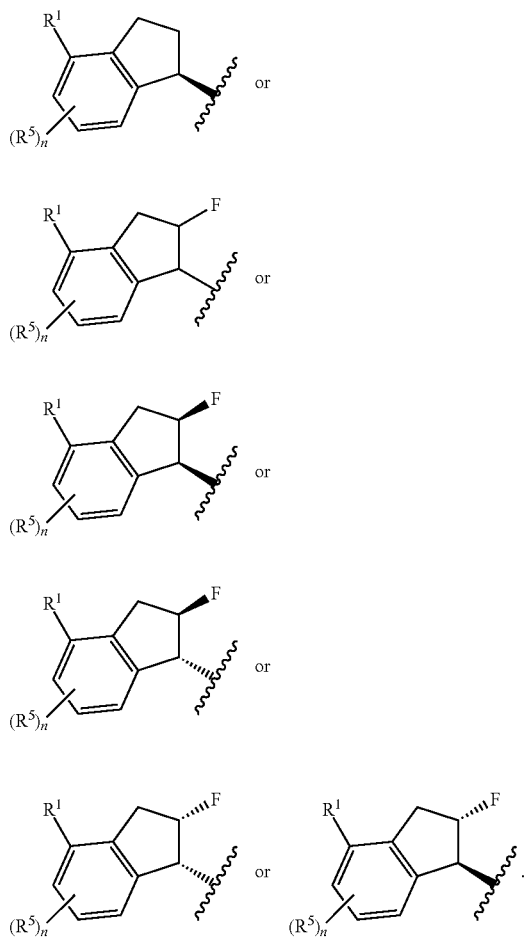

In some embodiments the compound, or a pharmaceutically acceptable salt thereof is a compound of Formula (I), (Ia), or (Ia1), wherein the portion shown as

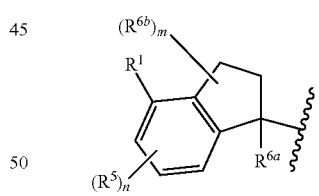

is

In some embodiments the compound, or a pharmaceutically acceptable salt thereof is a compound of Formula (I), (Ia), (Ia1), (Ib), (Ib1), (Ic), or (Ic1), wherein the portion shown as is

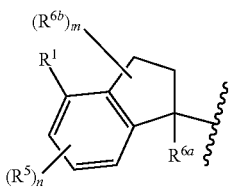

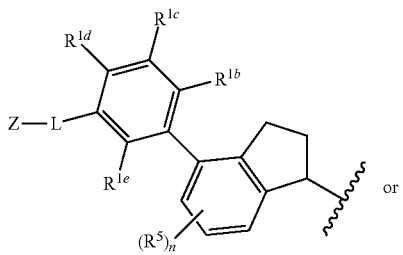

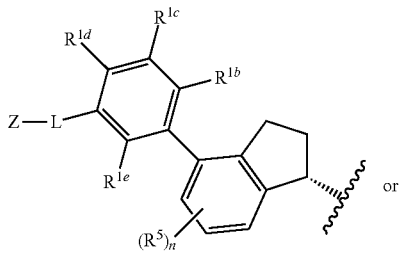

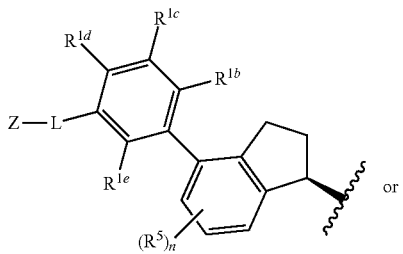

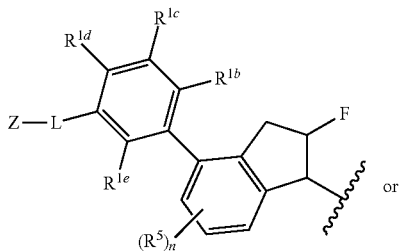

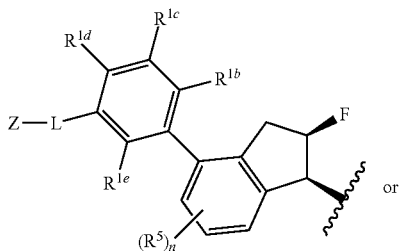

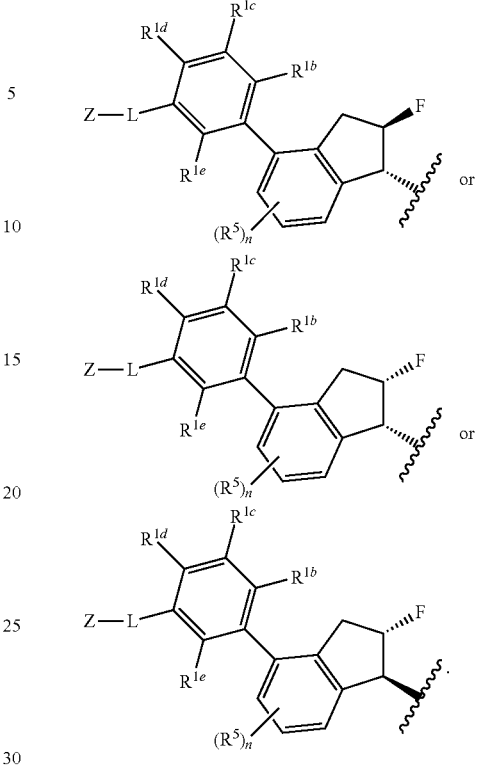

Returning to each of Formula (I), (II), (Ia), (IIa), (Ia1), (IIa1), (Ib), (IIb), (Ib1) (IIb1), (Ic), (IIc), (Ic1), and (IIc1) in some embodiments, $R^4$ is optionally substituted with 1 to 2 $R^{4a}$, wherein each $R^{4a}$ is independently selected from the group consisting of halogen, —CN, —$R^i$, —$CO_2R^j$, —$CONR^jR^k$, —$C(O)R^j$, —$OC(O)NR^jR^k$, —$NR^jC(O)R^k$, —$NR^jC(O)_2R^i$, —$NR^j$—$C(O)NR^jR^k$, —$NR^jR^k$, —$OR^j$, and —$S(O)_2NR^jR^k$. In some embodiments, $R^4$ is selected from the group consisting of O—$C_{1-4}$ alkyl, O—$C_{1-6}$ alkyl-CN, phenyl, pyridinyl, —O—$C_{1-2}$ alkyl-pyridinyl, —O—$C_{1-2}$ alkyl-pyrimidinyl, —O—$C_{1-2}$ alkyl-pyridazinyl, and —O—$C_{1-2}$ alkyl-phenyl, each of which is optionally substituted with 1 to 2 $R^{4a}$, wherein each $R^{4a}$ is independently selected from the group consisting of halogen, —CN, —$CO_2R^j$, —$NR^jR^k$, and —$OR^j$.

In some embodiments, the compound, or a pharmaceutically acceptable salt thereof, is selected from the compounds of Table 1 having an activity of ++ or +++. In some embodiments, the compound, or a pharmaceutically acceptable salt thereof, is selected from the compounds of Table 1 having an activity of +++. In some embodiments, the compound, or a pharmaceutically acceptable salt thereof, is selected from the compounds of Table 1 having an activity of ++. In some embodiments, the compound, or a pharmaceutically acceptable salt thereof, is selected from the compounds of Table 1 having an activity of +.

In addition to the compounds provided above, pharmaceutically acceptable salts of those compounds are also provided. In some embodiments, the pharmaceutically acceptable salts are selected from ammonium, calcium, magnesium, potassium, sodium, zinc, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, procaine, purines, theobromine, triethylamine, trimethylamine, tripropylamine, tromethamine, hydrochloric, carbonic, monohydrogencarbonic, phosphoric, monohydrogenphosphoric, dihydrogenphosphoric, acetic, propionic, isobutyric, malonic, benzoic, succinic, suberic, fumaric, mandelic, phthalic, benzenesulfonic, p-tolylsulfonic, citric, tartaric, methanesulfonic, arginate, glucuronic acid and galactunoric acids. In some embodiments, the pharmaceutically acceptable salts are selected from ammonium, calcium, magnesium, potassium, sodium, hydrochloric, carbonic, monohydrogencarbonic, phosphoric, monohydrogenphosphoric, dihydrogenphosphoric, acetic, propionic, isobutyric, malonic, benzoic, succinic, suberic, fumaric, mandelic, phthalic, benzenesulfonic, p-tolylsulfonic, citric, tartaric, methanesulfonic, arginate, glucuronic acid and galactunoric acids. In some embodiments, the pharmaceutically acceptable salts are sodium or hydrochloric.

In addition to salt forms, the present disclosure provides compounds which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

An ester may be used as a prodrug for the corresponding carboxylic acid. A $C_{1-10}$ alkyl ester or a $C_{1-10}$ haloalkyl ester may be used as a prodrug for the corresponding carboxylic acid. The following esters may be used: ter-butyl ester, methyl ester, ethyl ester, isopropyl ester. More specifically, ester prodrugs may be used as $R^3$ groups such as threonine or serine prodrug esters which are linked to the rest of the molecule through their nitrogen. More specifically, the following prodrugs may be used for $R^3$:

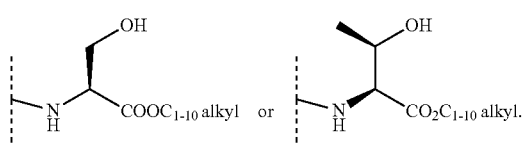

More specifically, the following prodrugs may be used for $R^3$:

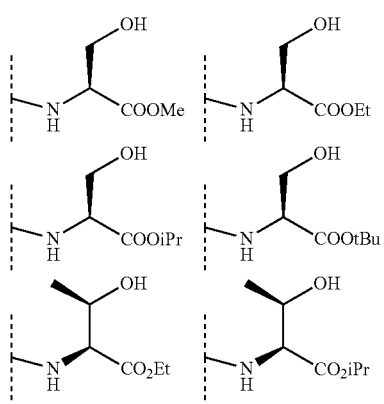

-continued

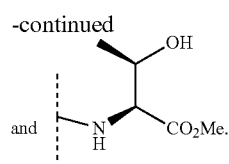

Pharmaceutical Compositions

In addition to the compounds provided herein, compositions of those compounds will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In another embodiment, a pharmaceutical composition comprising a compound of the present disclosure including a compound of Formula (I), (Ia), (II), or (IIa) or a pharmaceutically acceptable salt thereof, and a pharmaceutically acceptable excipient, is provided.

In some embodiments, the pharmaceutical composition further comprises one or more additional therapeutic agents. In some embodiments, the one or more additional therapeutic agent is selected from the group consisting of an antimicrobial agent, an antiviral agent, a cytotoxic agent, a gene expression modulatory agent, a chemotherapeutic agent, an anti-cancer agent, an anti-angiogenic agent, an immunotherapeutic agent, an anti-hormonal agent, an anti-fibrotic agent, radiotherapy, a radiotherapeutic agent, an anti-neoplastic agent, and an anti-proliferation agent. In some embodiments, the one or more additional therapeutic agent is selected from the group consisting of one or more of CCX354, CCX9588, CCX140, CCX872, CCX598, CCX6239, CCX9664, CCX2553, CCX 2991, CCX282, CCX025, CCX507, CCX430, CCX765, CCX224, CCX662, CCX650, CCX832, CCX168, and CCX168-M1.

The pharmaceutical compositions for the administration of the compounds of this disclosure may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self-emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, polyethylene glycol (PEG) of various average sizes (e.g., PEG400, PEG4000) and certain surfactants such as cremophor or solutol, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono- or di-glycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the disclosure may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present disclosure may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present disclosure are employed. As used herein, topical application is also meant to include the use of mouth washes and gargles.

The compounds of this disclosure may also be coupled to a carrier that is a suitable polymer as a targetable drug carrier. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the disclosure may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like. In one embodiment of the disclosure, the compound of the disclosure is coupled to a polymer or semipermeable polymer matrix that is formed as a stent or stent-graft device.

Methods of Treating Diseases and Disorders

The compounds of the disclosure may be used as immunomodulators. The compounds of the disclosure may be used as agonists, antagonists, partial agonists, inverse agonists, inhibitors of PD-1 and/or PD-L1 in a variety of contexts, both in vitro and in vivo. In some embodiments, the compounds of the disclosure may be used as inhibitors of the PD-1/PD-L1 protein protein interaction. In some embodiments, the compounds of the disclosure may be used as inhibitors of PD-L1. In some embodiments, the compounds of the disclosure may be used as inhibitors of the CD80/PD-L1 protein protein interaction. In some embodiments, the compounds of the disclosure may be used to inhibit the interaction between PD-1 and PD-L1 and/or PD-1 and CD80 and/or PD-1 and PD-L2 in vitro or in vivo. In some embodiments, the compounds of the disclosure may be used to inhibit VISTA and/or TIM-3. In some embodiments, the compounds of the disclosure may be inhibitors of the PD-1/PD-L1 protein protein interaction and inhibitors of VISTA and/or TIM-3. In some embodiments, in addition to being inhibitors of the PD-1/PD-L1 protein protein interaction, the compounds of the disclosure may be inhibitors of CTLA-4 and/or BTLA and/or LAG-3 and/or KLRG-1 and/or 2B4 and/or CD160 and/or HVEM and/or CD48 and/or E-cadherin and/or MHC-II and/or galectin-9 and/or CD86 and/or PD-L2 and/or VISTA and/or TIM-3 and/or CD80.

The compounds of the disclosure may be contacted with the receptor they interact with, in aqueous solution and under conditions otherwise suitable for binding of the ligand to the receptor. The receptor may be present in suspension (e.g., in an isolated membrane or cell preparation), in a cultured or isolated cell, or in a tissue or organ.

Preferably, the amount of the compounds of the disclosure contacted with the receptor should be sufficient to inhibit the PD-1/PD-L1 binding in vitro as measured, for example, using an ELISA. The receptor may be present in solution or suspension, in a cultured or isolated cell preparation or within a patient.

In some embodiments, the compounds of the present disclosure are useful for restoring and augmenting T cell activation. In some embodiments, the compounds of the present disclosure are useful for enhancing an immune response in a patient. In some embodiments, the compounds of the present disclosure are useful for treating, preventing, or slowing the progression of diseases or disorders in a variety of therapeutic areas, such as cancer and infectious diseases.

In some embodiments, the compounds of the present disclosure can be used for treating patients suffering from conditions that are responsive to PD-1/PD-L1 protein protein interaction modulation.

In some embodiments, a method of modulating an immune response mediated by the PD-1 signaling pathway in a subject, comprising administering to the subject a therapeutically effective amount of a compound of the present disclosure including a compound of Formula (I), (Ia), (II), or (IIa) or a pharmaceutically acceptable salt thereof or a composition comprising a compound of the present disclosure including a compound of Formula (I), (Ia), (II), or (IIa), or a pharmaceutically acceptable salt thereof, is provided.

In some embodiments, a method of enhancing, stimulating, modulating and/or increasing the immune response in a subject in need thereof, comprising administering to the subject a therapeutically effective amount of a compound of the present disclosure including a compound of Formula (I), (Ia), (II), or (IIa), or a pharmaceutically acceptable salt thereof or a composition of a compound of the present disclosure including a compound of Formula (I), (Ia), (II), or (IIa), or a pharmaceutically acceptable salt thereof, is provided.

In some embodiments, a method of inhibiting growth, proliferation, or metastasis of cancer cells in a subject in need thereof, comprising administering to the subject a therapeutically effective amount of a compound of the present disclosure including a compound of Formula (I), (Ia), (II), or (IIa), or a pharmaceutically acceptable salt thereof or a composition of a compound of the present disclosure including a compound of Formula (I), (Ia), (II), or (IIa), or a pharmaceutically acceptable salt thereof, is provided.

In some embodiments, a method of treating a subject in need thereof, comprising administering to the subject a therapeutically effective amount of a compound of the present disclosure including a compound of Formula (I), (Ia), (II), or (IIa), or a pharmaceutically acceptable salt thereof or a composition of a compound of the present disclosure including a compound of Formula (I), (Ia), (II), or (IIa), or a pharmaceutically acceptable salt thereof, is provided.

In some embodiments, the subject suffers from a disease or disorder selected from the group consisting of an infectious disease, a bacterial infectious disease, a viral infectious disease a fungal infectious disease, a solid tumor, a hematological malignancy, an immune disorder, an inflammatory disease, and cancer. In some embodiments, the disease or disorder is selected from the group consisting of melanoma, glioblastoma, esophagus tumor, nasopharyngeal carcinoma, uveal melanoma, lymphoma, lymphocytic lymphoma, primary CNS lymphoma, T-cell lymphoma, diffuse large B-cell lymphoma, primary mediastinal large B-cell lymphoma, prostate cancer, castration-resistant prostate cancer, chronic myelocytic leukemia, Kaposi's sarcoma fibrosarcoma, liposarcoma, chondrosarcoma, osteogenic sarcoma, angiosarcoma, lymphangiosarcoma, synovioma, meningioma, leiomyosarcoma, rhabdomyosarcoma, sarcoma of soft tissue, sarcoma, sepsis, biliary tumor, basal cell carcinoma, thymus neoplasm, cancer of the thyroid gland, cancer of the parathyroid gland, uterine cancer, cancer of the adrenal gland, liver infection, Merkel cell carcinoma, nerve tumor, follicle center lymphoma, colon cancer, Hodgkin's disease, non-Hodgkin's lymphoma, leukemia, chronic or acute leukemias including acute myeloid leukemia, chronic myeloid leukemia, acute lymphoblastic leukemia, chronic lymphocytic leukemia, multiple myeloma, ovary tumor, myelodysplastic syndrome, cutaneous or intraocular malignant melanoma, renal cell carcinoma, small-cell lung cancer, lung cancer, mesothelioma, breast cancer, squamous non-small cell lung cancer (SCLC), non-squamous NSCLC, colorectal cancer, ovarian cancer, gastric cancer, hepatocellular carcinoma, pancreatic carcinoma, pancreatic cancer, Pancreatic ductal adenocarcinoma, squamous cell carcinoma of the head and neck, cancer of the head or neck, gastrointestinal tract, stomach cancer, HIV, Hepatitis A, Hepatitis B, Hepatitis C, hepatitis D, herpes viruses, papillomaviruses, influenza, bone cancer, skin cancer, rectal cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the urethra, cancer of the penis, cancer of the bladder, cancer of the kidney, cancer of the ureter, carcinoma of the renal pelvis, neoplasm of the central nervous system (CNS), tumor angiogenesis, spinal axis tumor, brain stem glioma, pituitary adenoma, epidermoid cancer, abestosis, carcinoma, adenocarcinoma, papillary carcinoma, cystadenocarcinoma, bronchogenic carcinoma, renal cell carcinoma, transitional cell carcinoma, choriocarcinoma, seminoma, embryonal carcinoma, wilm's tumor, pleomorphic adenoma, liver cell papilloma, renal tubular adenoma, cystadenoma, papilloma, adenoma, leiomyoma, rhabdomyoma, hemangioma, lymphangioma, osteoma, chondroma, lipoma and fibroma.

In some embodiments, a therapeutically effective amount of one or more additional therapeutic agents is further administered to the subject. In some embodiments, the one or more additional therapeutic agents is selected from the group consisting of an antimicrobial agent, an antiviral agent, a cytotoxic agent, a gene expression modulatory agent, a chemotherapeutic agent, an anti-cancer agent, an anti-angiogenic agent, an immunotherapeutic agent, an anti-hormonal agent, an anti-fibrotic agent, radiotherapy, a radio-therapeutic agent, an anti-neoplastic agent, and an anti-proliferation agent. In some embodiments, the one or more additional therapeutic agent is selected from the group consisting of one or more of CCX354, CCX9588, CCX140, CCX872, CCX598, CCX6239, CCX9664, CCX2553, CCX 2991, CCX282, CCX025, CCX507, CCX430, CCX765, CCX224, CCX662, CCX650, CCX832, CCX168, and CCX168-M1.

In some embodiments, the compounds of the present disclosure may be used to inhibit an infectious disease. The infectious disease includes but is not limited to HIV, Influenza, Herpes, *Giardia*, Malaria, *Leishmania*, the pathogenic infection by the virus Hepatitis (A, B, and C), herpes virus (e.g., VZV, HSV-I, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus, pathogenic infection by the bacteria *chlamydia*, rickettsial bacteria, mycobacteria, staphylococci, streptococci, pneumonococci, meningococci and conococci, *Klebsiella, Proteus, Serratia, Pseudomonas, E. coli, Legionella*, diphtheria, *Salmonella*, bacilli, cholera, tetanus, botulism, anthrax, plague, leptospirosis, and Lyme's disease bacteria, pathogenic infection by the fungi *Candida (albicans, krusei, glabrata, tropicalis*, etc.), *Cryptococcus neoformans, Aspergillus (fumigatus, niger*, etc.), Genus *Mucorales (mucor, absidia, rhizophus), Sporothrix schenkii, Blastomyces dermatitidis, Paracoccidioides brasiliensis, Coccidioides immitis* and *Histoplasma capsulatum*, and pathogenic infection by the parasites *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi, Nippostrongylus brasiliensis.*

In some embodiments, the compounds of the present disclosure may be used to inhibit HIV infection, delay AIDS progression, deplete HIV viral reservoir or decrease the severity of symptoms or HIV infection and AIDS.

The compounds of the present disclosure may be used for the treatment of cancers and precancerous conditions in a subject.

Treatment methods provided herein include, in general, administration to a patient an effective amount of one or more compounds provided herein. Suitable patients include those patients suffering from or susceptible to (i.e., prophylactic treatment) a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient an effective amount of a compound one or more compounds provided herein. In a preferred embodiment, the compound(s) of the disclosure are preferably administered to a patient (e.g., a human) intravenously, orally or topically. The effective amount may be an amount sufficient to modulate the PD-1/PD-L1 interaction and/or an amount sufficient to reduce or alleviate the symptoms presented by the patient. Preferably, the amount administered is sufficient to yield a plasma concentration of the compound (or its active metabolite, if the compound is a pro-drug) high enough to sufficient to modulate the PD-1/PD-L1 interaction. Treatment regimens may vary depending on the compound used and the particular condition to be treated; for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

Combinations

A concomitant medicine comprising the compounds of the present disclosure and other drug may be administered as a combination preparation in which both components are contained in a single formulation, or administered as separate formulations. The administration by separate formulations includes simultaneous administration and administration with some time intervals. In the case of the administration with some time intervals, the compound of the present disclosure can be administered first, followed by another drug or another drug can be administered first, followed by the compound of the present disclosure. The administration method of the respective drugs may be the same or different.

The dosage of the other drug can be properly selected, based on a dosage that has been clinically used. The compounding ratio of the compound of the present disclosure and the other drug can be properly selected according to age and weight of a subject to be administered, administration method, administration time, disorder to be treated, symptom and combination thereof. For example, the other drug may be used in an amount of 0.01 to 100 parts by mass, based on 1 part by mass of the compound of the present disclosure. The other drug may be a combination of two or more kind of arbitrary drugs in a proper proportion.

The compounds described herein may be used or combined with one or more therapeutic agent such as an antimicrobial agent, an antiviral agent, a cytotoxic agent, a gene expression modulatory agent, a chemotherapeutic agent, an anti-cancer agent, an anti-angiogenic agent, an immunotherapeutic agent, an anti-hormonal agent, an anti-fibrotic agent, radiotherapy, a radiotherapeutic agent, an anti-neoplastic agent, and an anti-proliferation agent. These therapeutic agents may be in the forms of compounds, antibodies, polypeptides, or polynucleotides.

The compounds described herein may be used or combined with one or more of a therapeutic antibody, a bispecific antibody and "antibody-like" therapeutic protein (such as DARTs®, Duobodies®, Bites®, XmAbs®, TandAbs®, Fab derivatives), an antibody-drug conjugate (ADC), a virus, an oncolytic virus, gene modifiers or editors such as CRISPR (including CRISPR Cas9), zinc finger nucleases or synthetic nucleases (TALENs), a CAR (chimeric antigen receptor) T-cell immunotherapeutic agent, or any combination thereof.

Examples of chemotherapeutics include an alkylation agent, nitrosourea agent, antimetabolite, anticancer antibiotics, vegetable-origin alkaloid, topoisomerase inhibitor, hormone drug, hormone antagonist, aromatase inhibitor, P-glycoprotein inhibitor, platinum complex derivative, other immunotherapeutic drugs and other anticancer drugs.

The compounds described herein may be used or combined with a cancer treatment adjunct, such as a leucopenia (neutropenia) treatment drug, thrombocytopenia treatment drug, antiemetic and cancer pain intervention drug, concomitantly or in a mixture form.

The compounds described herein may be used or combined with a kinase inhibitor.

In one embodiment, the compounds of the present disclosure can be used with other immunomodulators and/or a potentiating agent concomitantly or in a mixture form. Examples of the immunomodulator include various cytokines, vaccines and adjuvants. Examples of these cytokines, vaccines and adjuvants that stimulates immune responses include but not limited to GM-CSF, M-CSF, G-CSF, interferon-a, beta, or gamma, IL-1, IL-2, IL-3, IL-12, Poly (I:C) and CPG. The potentiating agents include cyclophosphamide and analogs of cyclophosphamide, anti-TGF and imatinib (Gleevac), a mitosis inhibitor, such as paclitaxel, Sunitinib (Sutent) or other antiangiogenic agents, an aromatase inhibitor, such as letrozole, an A2a adenosine receptor (A2AR) antagonist, an angiogenesis inhibitor, anthracyclines, oxaliplatin, doxorubicin, TLR4 antagonists, and IL-18 antagonists.

In some embodiments, the compounds described herein may be used or combined with one or more modulator of CCR1, CCR2, CCR3, CCR4, CCR5, CCR6, CCR7, CCR8, CCR9, CCR10, CCR11, CXCR1, CXCR2, CXCR3, CXCR4, CXCR5, CXCR6, CXCR7, CX$_3$CR1, ChemR23, C5aR, C5a, and C5. In some embodiments, the modulator is an antagonist.

In some embodiments, the compounds described herein may be used or combined with one or more of CCX354, CCX9588, CCX140, CCX872, CCX598, CCX6239, CCX9664, CCX2553, CCX 2991, CCX282, CCX025, CCX507, CCX430, CCX765, CCX224, CCX662, CCX650, CCX832, CCX168, and CCX168-M1.

Dosage

Dosage levels of the order of from about 0.1 mg to about 140 mg per kilogram of body weight per day are useful in the treatment or preventions of conditions involving the PD-1/PD-L1 interaction (about 0.5 mg to about 7 g per human patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. For compounds administered orally, transdermally, intravaneously, or subcutaneously, it is preferred that sufficient amount of the compound be administered to achieve a serum concentration of 5 ng (nanograms)/mL-10 µg (micrograms)/mL serum, more preferably sufficient compound to achieve a serum concentration of 20 ng-1 µg/ml serum should be administered, most preferably sufficient compound to achieve a serum concentration of 50 ng/ml-200 ng/ml serum should be administered. For direct injection into the synovium (for the treatment of arthritis) sufficient compounds should be administered to achieve a local concentration of approximately 1 micromolar.

Frequency of dosage may also vary depending on the compound used and the particular disease treated. However, for treatment of most disorders, a dosage regimen of 4 times daily, three times daily, or less is preferred, with a dosage regimen of once daily or 2 times daily being particularly preferred. It will be understood, however, that the specific dose level for any particular patient will depend upon a variety of factors including the activity of the specific compound employed, the age, body weight, general health, sex, diet, time of administration, route of administration, and rate of excretion, drug combination (i.e., other drugs being administered to the patient), the severity of the particular disease undergoing therapy, and other factors, including the judgment of the prescribing medical practitioner.

In another aspect of the disclosure, the compounds of the disclosure can be used in a variety of non-pharmaceutical in vitro and in vivo application. The compounds of the disclosure may also be used as positive controls in assays for PD-1/PD-L1 interaction activity, i.e., as standards for determining the ability of a candidate agent to bind to PD-1 and/or PD-L1, or as radiotracers for positron emission tomography (PET) imaging or for single photon emission computerized tomography (SPECT).

Also within the scope of the present disclosure are kits comprising a compound of the present disclosure or pharmaceutically acceptable salts thereof and instructions for use. The kit can further contain at least one additional reagent. Kits typically include a label indicating the intended use of the contents of the kit. The term label includes any writing, or recorded material supplied on or with the kit, or which otherwise accompanies the kit.

General Synthetic Procedures

The embodiments are also directed to processes and intermediates useful for preparing the subject compounds or pharmaceutically acceptable salts thereof.

Exemplary chemical entities useful in methods of the embodiments will now be described by reference to illustrative synthetic schemes for their general preparation herein and in the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

Representative syntheses of compounds of the present disclosure are described in the scheme below, and the particular examples that follow. Schemes 1 and 2 are provided as further embodiment of the disclosure and illustrate general methods which were used to prepare compounds of the present disclosure including compounds of Formula (I), (Ia), (II), or (IIa), and which can be used to prepare additional compounds having the Formula (I), (Ia), (II), or (IIa). The methodology is compatible with a wide variety of functionalities.

Scheme 1

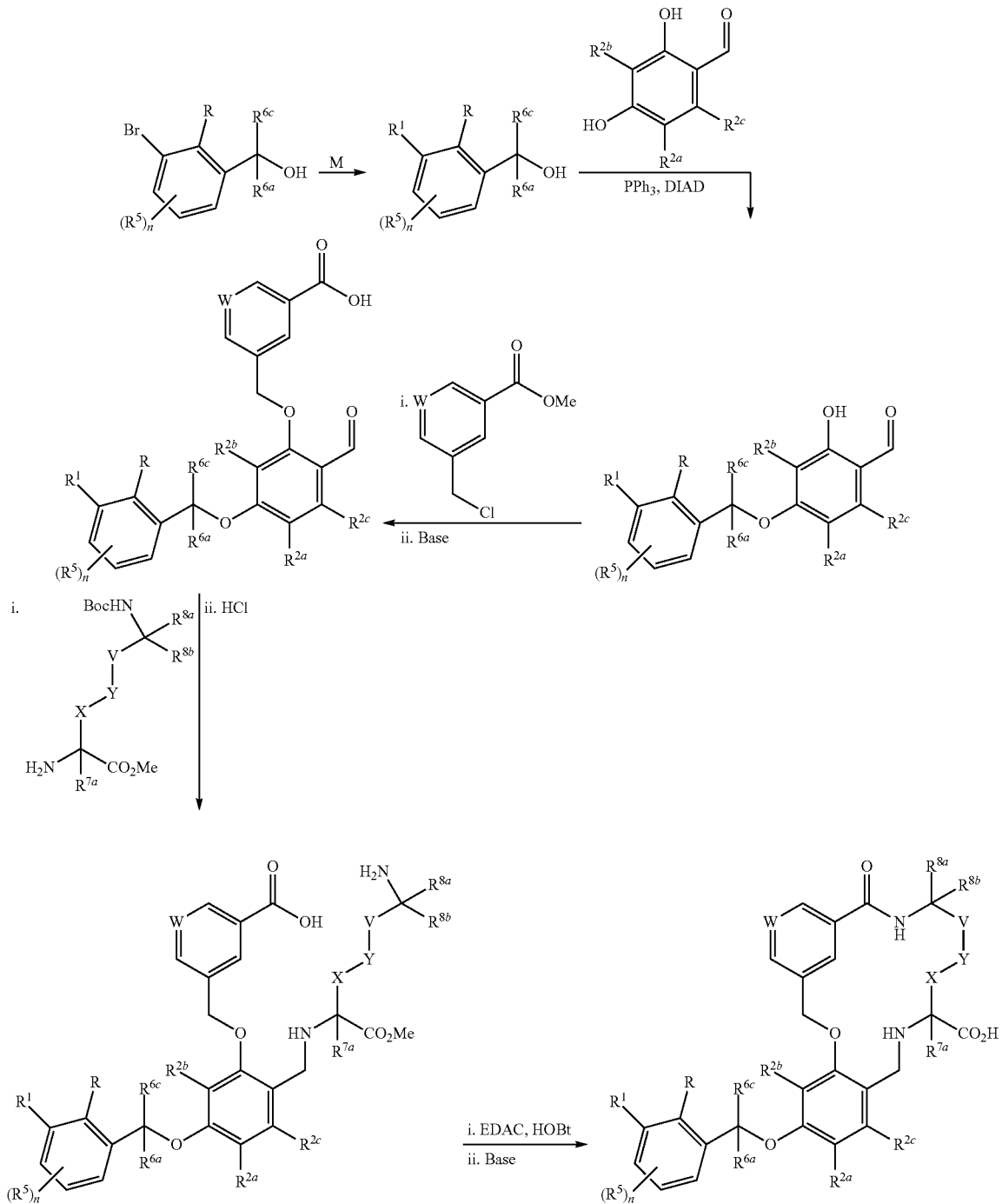

The 3-bromobenzyl alcohol can be subjected to Suzuki coupling conditions to introduce the appropriate $R^1$ group. In the subsequent step, the ether bond can be formed using reagents such as triphenyl phosphine and diisopropyl or diethyl azodicarboxylate. Alkylation of the phenol intermediate can be achieved using the appropriate alkyl halide or mesylate reagent. Carboxylic acid methyl ester hydrolysis can be achieved using a base such lithium hydroxide. The reductive amination can be accomplished using the appropriate amine and a reducing agent such as sodium triacetoxyborohydride in the presence of mild acid such as acetic acid. Boc deprotection can be achieved using HCl. The macrolactam formation can be achieved using EDAC and HOBt under dilute reaction conditions. And the carboxylic acid methyl ester hydrolysis can be achieved using a base such as lithium hydroxide. The transformations shown in Scheme 1 may be performed in any order that is compatible with the functionality of the particular pendant groups.

Scheme 2

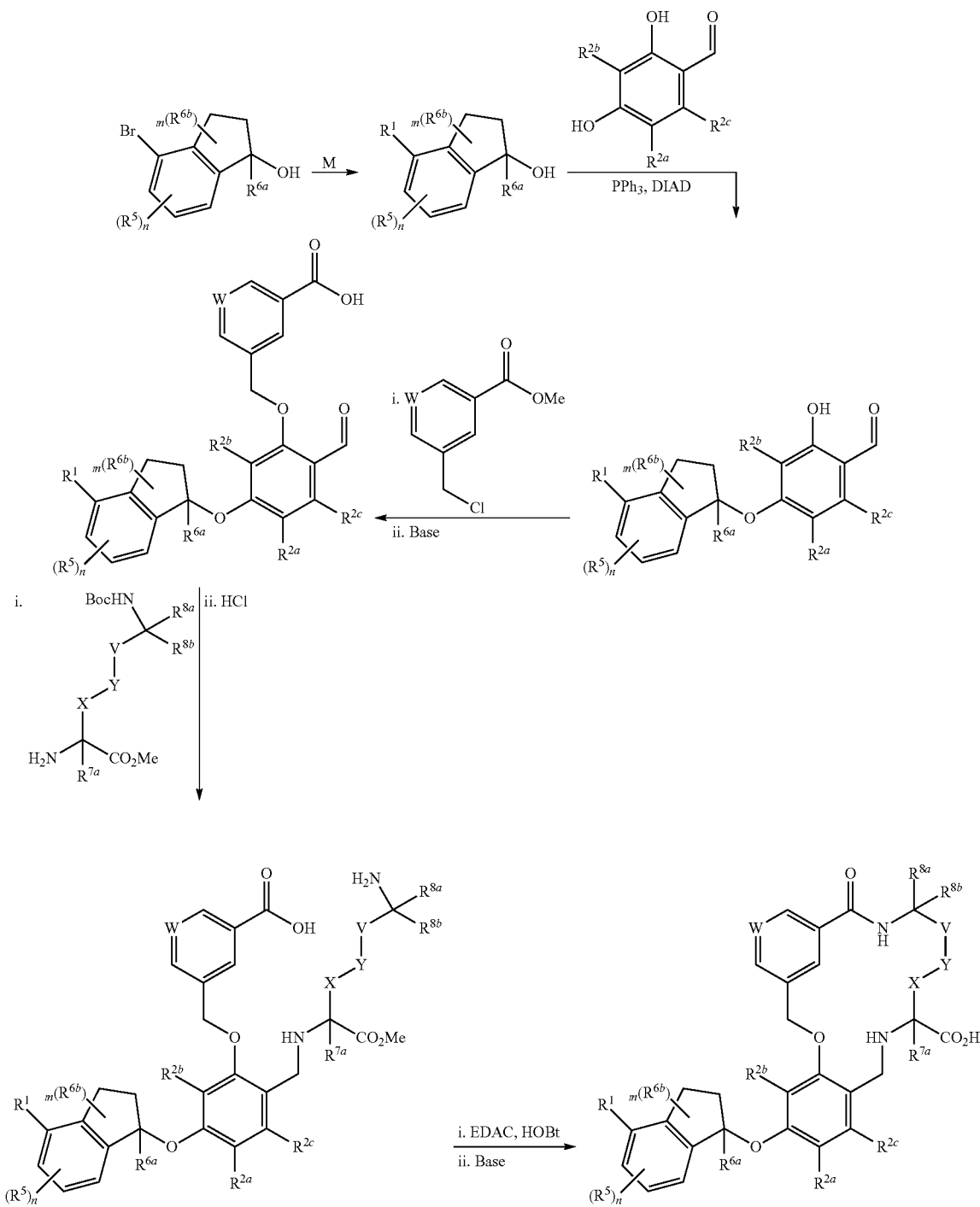

The 4-bromoindanol derivative can be subjected to Suzuki coupling conditions to introduce the appropriate R[1] group. In the subsequent step, the ether bond can be formed using reagents such as triphenyl phosphine and diisopropyl or diethyl azodicarboxylate. Alkylation of the phenol intermediate can be achieved using the appropriate alkyl halide or mesylate reagent. Carboxylic acid methyl ester hydrolysis can be achieved using a base such lithium hydroxide. The reductive amination can be accomplished using the appropriate amine and a reducing agent such as sodium triacetoxyborohydride in the presence of mild acid such as acetic acid. Boc deprotection can be achieved using HCl. The macrolactam formation can be achieved using EDAC and HOBt under dilute reaction conditions. And the carboxylic acid methyl ester hydrolysis can be achieved using a base such as lithium hydroxide. The transformations shown in Scheme 2 may be performed in any order that is compatible with the functionality of the particular pendant groups and using optically pure (R)-4-bromoindanol or (S)-4-bromoindanol.

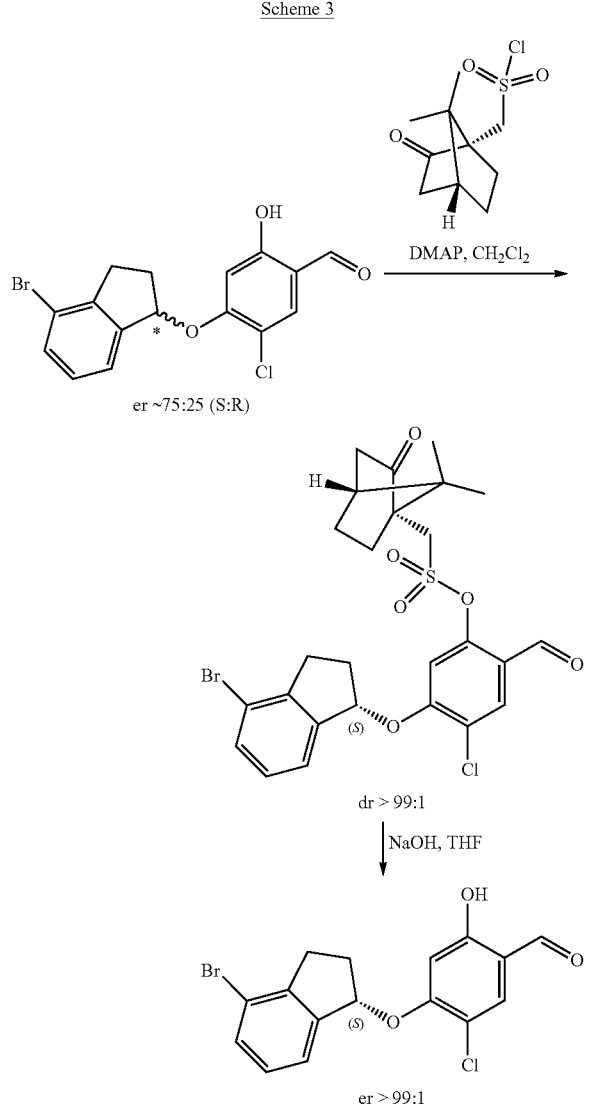

Scheme 3

As an example, enrichment of optical purity of chiral intermediates can be achieved as described in Scheme 3.

EXAMPLES

The following Examples illustrate various methods of making compounds of this disclosure including compounds of Formula (I), (Ia), (II), or (IIa). The following examples are offered to illustrate, but not to limit the claimed disclosure.

Reagents and solvents used below can be obtained from commercial sources such as Aldrich Chemical Co. (Milwaukee, Wis., USA). $^1$H-NMR spectra were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge. In the examples, a single m/z value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HPi1100 HPLC for sample delivery. Normally the analyte was dissolved in methanol or $CH_3CN$ at 0.1 mg/mL and 1 microliter was infused with the delivery solvent into the mass spectrometer, which scanned from 100 to 1000 Daltons. All compounds could be analyzed in the positive or negative ESI mode, using acetonitrile/water with 1% formic acid as the delivery solvent.

The following abbreviations are used in the Examples and throughout the description of the disclosure: TLC means Thin layer chromatography, DMF means dimethylformamide, EDAC means N-(3-dimethylaminopropyl)-N'-ethylcarbodiimide hydrochloride, DIPEA means N,N-diisopropylethylamine, HOBT means 1-hydroxybenzotriazole hydrate, DCM means dichloromethane, THF means tetrahydrofuran, PBS means phosphate buffered saline, BSA means bovine serum albumin, HRP means horseradish peroxidase, and TMB means 3, 3', 5, 5' tetramethyl benzidine.

Compounds within the scope of this disclosure can be synthesized as described below, using a variety of reactions known to the skilled artisan. One skilled in the art will also recognize that alternative methods may be employed to synthesize the target compounds of this disclosure, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed unless a specific enantiomer is specified.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1: Synthesis of the lithium salt of (S)-$4^4$-chloro-$5^4$-((2-methyl-[1,1'-biphenyl]-3-yl)methoxy)-13-oxo-3-oxa-6,12-diaza-1(3,5)-pyridina-4(1,2)-benzenacyclotridecaphane-7-carboxylic acid

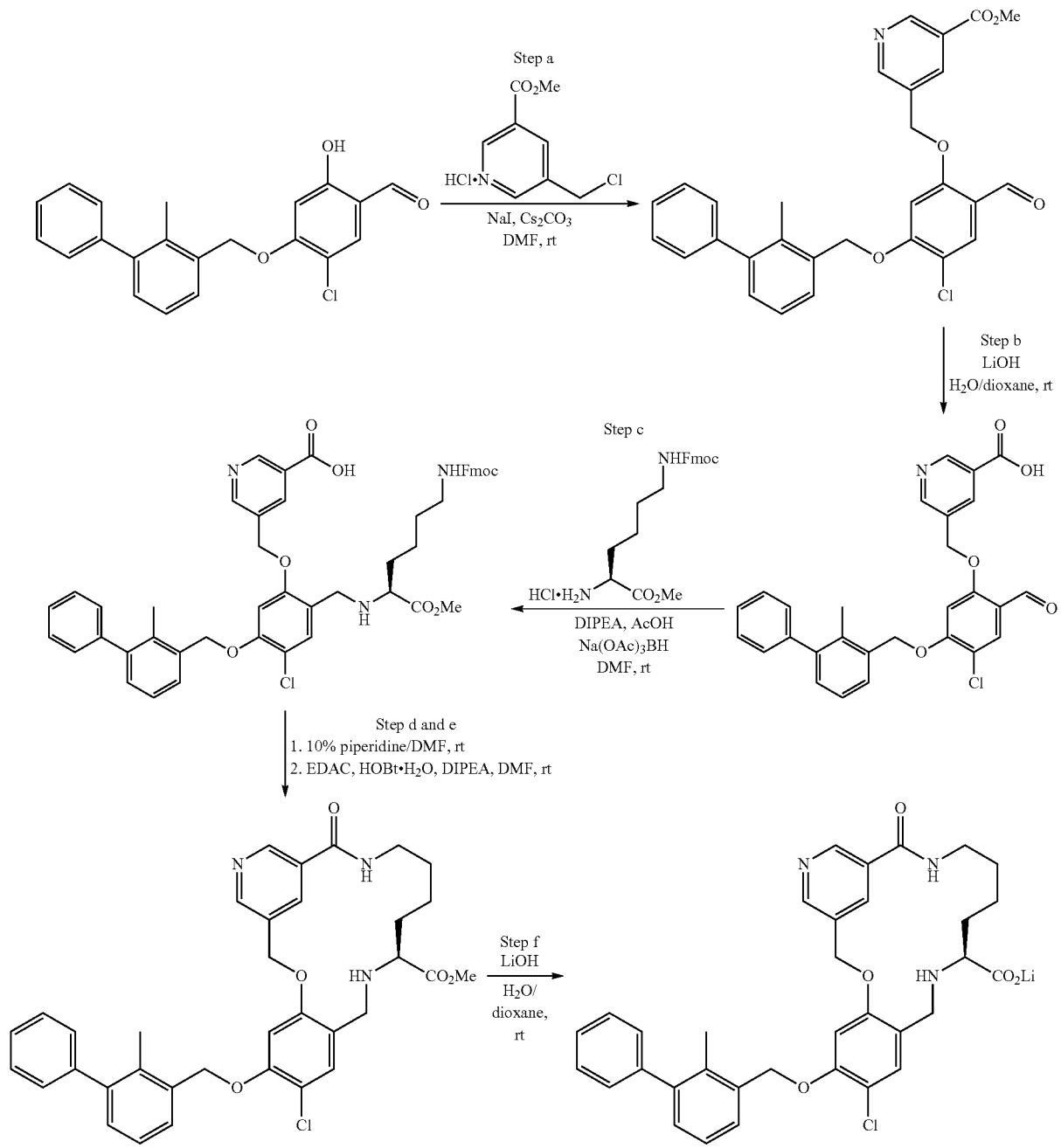

Step a: To a 100 mL round bottom flask was added 5-chloro-2 hydroxy-4-((2-methyl-[1,1'-biphenyl]-3-yl)methoxybenzaldehyde (1.0 g, 2.8 mmol), methyl-5-(chloromethy)nicotinate hydrochloride salt (0.82 g, 3.7 mmol), cesium carbonate (4.6 g, 14.5 mmol), sodium iodide (42 mg, 0.28 mmol), and DMF (20 mL). The mixture was stirred at room temperature for 2 days. Water (50 mL) was added and the aqueous mixture was extracted with EtOAc (3×50 mL). The organics were combined, dried over MgSO$_4$, filtered, and concentrated in vacuo to afford methyl 5-((4-chloro-2-formyl-5-((2-methyl-[1,1'-biphenyl]-3-yl)methoxy)phenoxy)methyl)nicotinate.

Step b: To a biphasic solution of methyl 5-((4-chloro-2-formyl-5-((2-methyl-[1,1'-biphenyl]-3-yl)methoxy)phenoxy)methyl)nicotinate (470 mg, 0.93 mmol) in dioxane (5.0 mL) and water (0.5 mL) was added lithium hydroxide monohydrate (40 mg, 0.93 mmol). The mixture was stirred for 2 hours at room temperature and then concentrated in vacuo to afford 5-((4-chloro-2-formyl-5-((2-methyl-[1,1'-biphenyl]-3-yl)methoxy)phenoxy)methyl)nicotinic acid.

Step c: To a solution of 5-((4-chloro-2-formyl-5-((2-methyl-[1,1'-biphenyl]-3-yl)methoxy)phenoxy)methyl) nicotinic acid (230 mg, 0.47 mmol) and N-Fmoc-L-lysine methyl ester hydrochloride (0.97 g, 2.33 mmol) in DMF (6 mL) was added acetic acid (133 µL, 2.33 mmol) and N,N-diisopropylethylamine (283 µL, 1.63 mmol). The mixture was allowed to stir at room temperature for 15 min before sodium triacetoxyborohydride (300 mg, 1.40 mmol) was added in portions over 5 min. After stirring for 1 h, an additional amount of sodium triacetoxyborohydride (230 mg, 1.08 mmol) was added in one portion. The reaction mixture was stirred at room temperature for an additional 4 h before the mixture was concentrated in vacuo and purified by flash chromatography (10% MeOH/DCM) to afford (S)-5-((2-(((6-((((9H-fluoren-9-yl)methoxy)carbonyl)amino)-1-methoxy-1-oxohexan-2-yl)amino)methyl)-4-chloro-5-((2-methyl-[1,1'-biphenyl]-3-yl)methoxy)phenoxy)methyl)nicotinic acid.

Step d: To a solution of (S)-5-((2-(((6-((((9H-fluoren-9-yl)methoxy)carbonyl)amino)-1-methoxy-1-oxohexan-2-yl)amino)methyl)-4-chloro-5-((2-methyl-[1,1'-biphenyl]-3-yl)methoxy)phenoxy)methyl)nicotinic acid (46 mg, 0.054 mmol) in DMF (0.45 mL) was added piperidine (50 µL). After stirring for 15 min at room temperature, the mixture was concentrated in vacuo to afford (S)-5-((2-(((6-amino-1-methoxy-1-oxohexan-2-yl)amino)methyl)-4-chloro-5-((2-methyl-[1,1'-biphenyl]-3-yl)methoxy)phenoxy)methyl)nicotinic acid.

Step e: To a solution of(S)-5-((2-(((6-amino-1-methoxy-1-oxohexan-2-yl)amino)methyl)-4-chloro-5-((2-methyl-[1,1'-biphenyl]-3-yl)methoxy)phenoxy)methyl)nicotinic acid (34 mg, 0.054 mmol) in DMF (5.4 mL) was added N-(3-dimethylaminopropyl)-N'-ethylcarbodiimide hydrochloride (41 mg, 0.22 mmol), 1-hydroxybenzotriazole hydrate (17 mg, 0.11 mmol), and N,N-diisopropylethylamine (94 µL, 0.54 mmol). The mixture was left to stir for 36 h and then concentrated in vacuo. The crude solid was re-suspended in acetonitrile, filtered, and washed with acetonitrile to afford methyl (S)-$4^4$-chloro-$4^5$-((2-methyl-[1,1'-biphenyl]-3-yl)methoxy)-13-oxo-3-oxa-6,12-diaza-1(3,5)-pyridina-4(1,2)-benzenacyclotridecaphane-7-carboxylate.

Step f: To a biphasic solution of methyl (S)-$4^4$-chloro-$4^5$-((2-methyl-[1,1'-biphenyl]-3-yl)methoxy)-13-oxo-3-oxa-6,12-diaza-1(3,5)-pyridina-4(1,2)-benzenacyclotridecaphane-7-carboxylate (13 mg, 0.021 mmol) in dioxane (1 mL) and water (0.5 mL) was added lithium hydroxide monohydrate (4 mg, 0.064 mmol). After stirring at room temperature for 5 h, the reaction mixture was frozen and lyophilized to afford the lithium salt of (S)-$4^4$-chloro-$5^4$-((2-methyl-[1,1'-biphenyl]-3-yl)methoxy)-13-oxo-3-oxa-6,12-diaza-1(3,5)-pyridina-4(1,2)-benzenacyclotridecaphane-7-carboxylic acid. MS: (ES) m/z calculated for $C_{34}H_{34}ClN_3O_5$ [M+H]$^+$ 600.2, found 600.1. $^1$H NMR (400 MHz, DMSO-d$_6$) δ 9.63 (br s, 1H), 8.81 (s, 1H), 8.79 (d, J=2.0 Hz, 1H), 8.74 (s, 1H), 7.50-7.46 (m, 2H), 7.45 (d, J=7.6 Hz, 1H), 7.4 1-7.35 (m, 1H), 7.35-7.30 (m, 2H), 7.26 (d, J=5.8 Hz, 2H), 7.20 (d, J=7.5 Hz, 1H), 7.08 (s, 1H), 5.43 (q, J=13.7 Hz, 2H), 5.22 (s, 2H), 3.63-3.56 (m, 1H), 3.51-3.44 (m, 1H), 2.71-2.61 (m, 1H), 2.23 (s, 3H), 2.00-1.89 (m, 1H), 1.60-1.49 (m, 3H), 1.49-1.35 (m, 4H).

Example 2: Synthesis of the trifluoroacetic acid salt of (S)-$4^4$-chloro-$4^5$-((3'-(3-(4-hydroxypiperidin-1-yl)propoxy)-2,2'-dimethyl-[1,1'-biphenyl]-3-yl)methoxy)-13-oxo-3-oxa-6,12-diaza-1(3,5)-pyridina-4(1,2)-benzenacyclotridecaphane-7-carboxylic acid

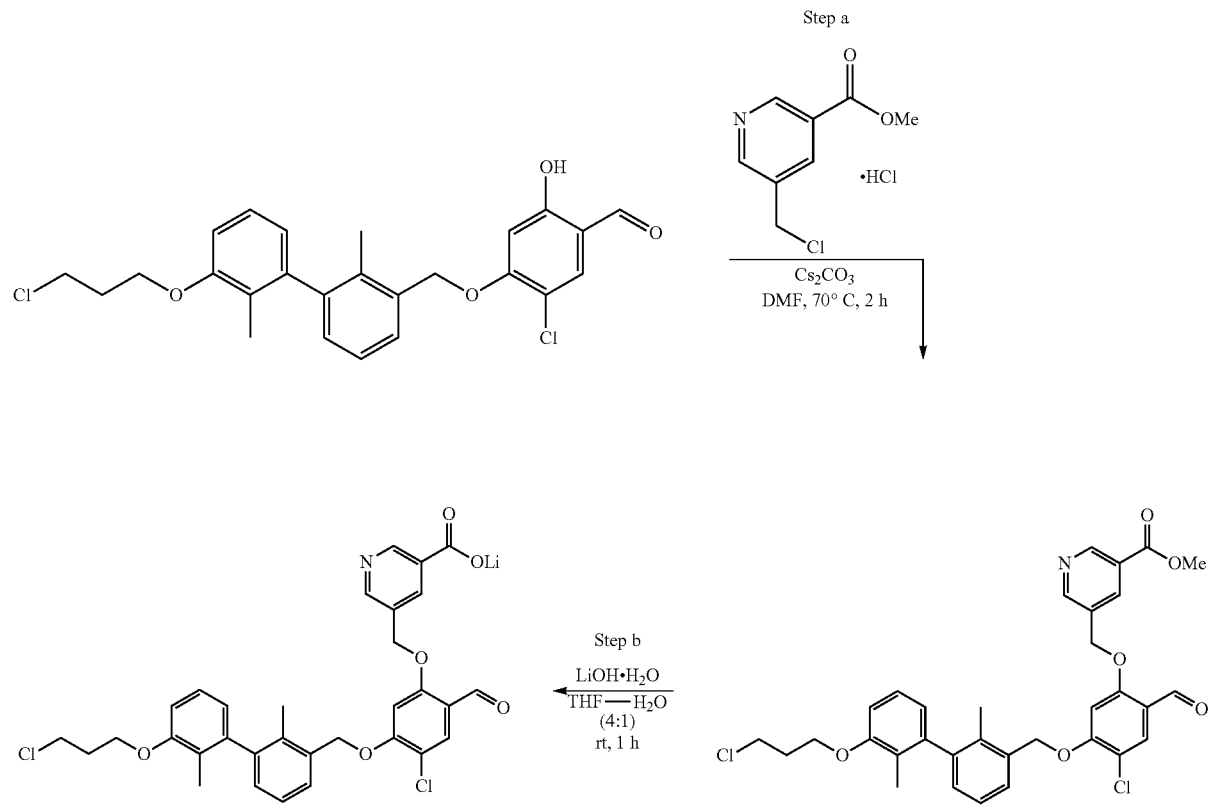

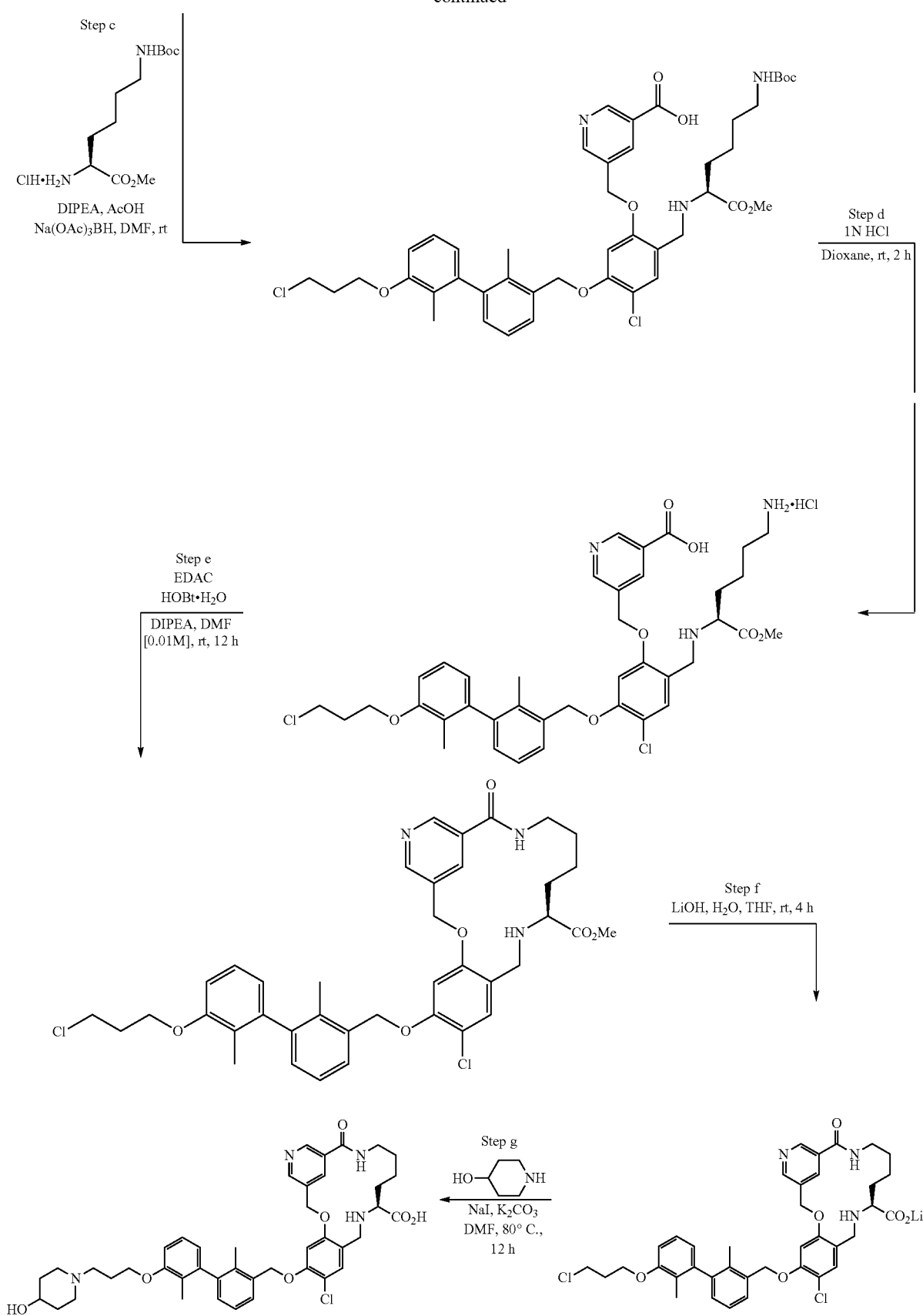

Step a: A mixture of 5-chloro-4-((3'-(3-chloropropoxy)-2,2'-dimethyl-[1,1'-biphenyl]-3-yl)methoxy)-2-hydroxybenzaldehyde (100 mg, 0.218 mmol), methyl-5-(chloromethy)nicotinate hydrochloride salt (48 g, 0.218 mmol), and cesium carbonate (214 g, 0.655 mmol) in DMF (1 mL) was stirred at 70° C. for 2 h. Water (10 mL) was added and the aqueous mixture was extracted with EtOAc (3×20 mL). The organics were combined, dried over $MgSO_4$, filtered, and concentrated in vacuo to afford methyl 5-((4-chloro-5-((3'-(3-chloropropoxy)-2,2'-dimethyl-[1,1'-biphenyl]-3-yl)methoxy)-2-formylphenoxy)methyl)nicotinate.

Step b: To a biphasic solution of methyl 5-((4-chloro-5-((3'-(3-chloropropoxy)-2,2'-dimethyl-[1,1'-biphenyl]-3-yl)methoxy)-2-formylphenoxy)methyl)nicotinate (110 mg, 0.181 mmol) in THF (2 mL) and water (0.228 mL) was added 1M aqueous lithium hydroxide monohydrate (0.272 mL, 0.272 mmol). The mixture was stirred for an hour at room temperature and then concentrated in vacuo to afford methyl 5-((4-chloro-5-((3'-(3-chloropropoxy)-2,2'-dimethyl-[1,1'-biphenyl]-3-yl)methoxy)-2-formylphenoxy)methyl)nicotinate lithium salt.

Step c: To a solution of 5-((4-chloro-5-((3'-(3-chloropropoxy)-2,2'-dimethyl-[1,1'-biphenyl]-3-yl)methoxy)-2-formylphenoxy)methyl)nicotinate lithium salt (110 mg, 0.185 mmol) and methyl $N^6$-(tert-butoxycarbonyl)-L-lysinate hydrochloride (55 mg, 0.185 mmol) in DMF (2 mL) was added acetic acid (60 μL, 0.925 mmol), N,N-diisopropylethylamine (50 μL, 0.277 mmol) and sodium triacetoxyborohydride (78 mg, 0.37 mmol). After stirring for 5 h at room temperature, additional sodium triacetoxyborohydride (100 mg, 0.47 mmol) and acetic acid (50 μL, 0.83 mmol) were added and the reaction was stirred overnight at room temperature. The reaction mixture was diluted with 2:1 $CHCl_3$/isopropanol (30 mL), washed with aqueous 1N HCl (10 mL) and saturated aqueous $NaHCO_3$ (10 mL), dried ($Na_2SO_4$), and concentrated in vacuo to afford (S)-5-((2-(((6-(((tert-butoxycarbonyl)amino)-1-methoxy-1-oxohexan-2-yl)amino)methyl)-4-chloro-5-((3'-(3-chloropropoxy)-2,2'-dimethyl-[1,1'-biphenyl]-3-yl)methoxy)phenoxy)methyl)nicotinic acid.

Step d: To a solution of (S)-5-((2-((((6-(((tert-butoxycarbonyl)amino)-1-methoxy-1-oxohexan-2-yl)amino)methyl)-4-chloro-5-((3'-(3-chloropropoxy)-2,2'-dimethyl-[1,1'-biphenyl]-3-yl)methoxy)phenoxy)methyl)nicotinic acid (162 mg, 0.193 mmol) in dioxane (3 mL) was added 1N HCl in dioxane (1 mL). After stirring for 2 h at room temperature, the mixture was concentrated in vacuo to afford (S)-5-((2-(((6-amino-1-methoxy-1-oxohexan-2-yl)amino)methyl)-4-chloro-5-((3'-(3-chloropropoxy)-2,2'-dimethyl-[1,1'-biphenyl]-3-yl)methoxy)phenoxy)methyl)nicotinic acid hydrochloride.

Step e: To a solution of (S)-5-((2-(((6-amino-1-methoxy-1-oxohexan-2-yl)amino)methyl)-4-chloro-5-((3'-(3-chloropropoxy)-2,2'-dimethyl-[1,1'-biphenyl]-3-yl)methoxy)phenoxy)methyl)nicotinic acid hydrochloride (160 mg, 0.189 mmol) in DMF (20 mL) was added N-(3-dimethylaminopropyl)-N'-ethylcarbodiimide hydrochloride (300 mg, 1.562 mmol), 1-hydroxybenzotriazole hydrate (100 mg, 0.65 mmol), and N,N-diisopropylethylamine (329 μL, 1.89 mmol). The mixture was left to stir overnight at room temperature and then concentrated in vacuo. EtOAc (20 mL) was added to the residue and washed with saturated aqueous $NH_4Cl$ (20 mL). The organic layer was separated and washed with water (10 mL) and brine (10 mL), dried ($Na_2SO_4$), and concentrated in vacuo. The crude product was purified by automated flash chromatography ($SiO_2$, 10% MeOH in $CH_2Cl_2$) to afford methyl (S)-$4^4$-chloro-45-((3'-(3-chloropropoxy)-2,2'-dimethyl-[1,1'-biphenyl]-3-yl)methoxy)-13-oxo-3-oxa-6,12-diaza-1(3,5)-pyridina-4(1,2)-benzenacyclotridecaphane-7-carboxylate.

Step f: To a biphasic solution of methyl (S)-$4^4$-chloro-45-((3'-(3-chloropropoxy)-2,2'-dimethyl-[1,1'-biphenyl]-3-yl)methoxy)-13-oxo-3-oxa-6,12-diaza-1(3,5)-pyridina-4(1,2)-benzenacyclotridecaphane-7-carboxylate (150 mg, 0.209 mmol) in THF (4 mL) and water (0.5 mL) was added 1M aqueous lithium hydroxide (500 μL, 0.5 mmol). After stirring at room temperature for 4 h, the reaction mixture was concentrated in vacuo to afford lithium (S)-$4^4$-chloro-$4^5$-((3'-(3-chloropropoxy)-2,2'-dimethyl-[1,1'-biphenyl]-3-yl)methoxy)-13-oxo-3-oxa-6,12-diaza-1(3,5)-pyridina-4(1,2)-benzenacyclotridecaphane-7-carboxylate.

Step g: To a solution of (S)-$4^4$-chloro-$4^5$-((3'-(3-chloropropoxy)-2,2'-dimethyl-[1,1'-biphenyl]-3-yl)methoxy)-13-oxo-3-oxa-6,12-diaza-1(3,5)-pyridina-4(1,2)-benzenacyclotridecaphane-7-carboxylic acid lithium salt (130 mg, 0.18 mmol) in DMF (3 mL) was added piperidin-4-ol (183 mg, 1.8 mmol), $K_2CO_3$ (124 mg, 0.9 mmol) and NaI (54 mg, 0.36 mmol). The resulting suspension was stirred at 80° C. overnight. The reaction mixture was filtered and concentrated in vacuo, and the crude was purified by reverse phase preparative HPLC ($CH_3CN$—$H_2O$ with 0.1% TFA) to obtain the trifluoroacetic acid salt of (S)-$4^4$-chloro-$4^5$-((3'-(3-(4-hydroxypiperidin-1-yl)propoxy)-2,2'-dimethyl-[1,1'-biphenyl]-3-yl)methoxy)-13-oxo-3-oxa-6,12-diaza-1(3,5)-pyridina-4(1,2)-benzenacyclotridecaphane-7-carboxylic acid. MS: (ES) m/z calculated for $C_{43}H_{52}ClN_4O_7$ $[M+H]^+$ 771.3, found 771.2. $^1H$ NMR (400 MHz, Methanol-$d_4$) δ 8.85 (d, J=2.1 Hz, 1H), 8.76-8.71 (m, 1H), 8.48 (s, 1H), 7.61 (s, 1H), 7.52 (d, J=7.7 Hz, 1H), 7.24 (dt, J=20.8, 7.9 Hz, 2H), 7.16-7.04 (m, 2H), 6.95 (d, J=8.2 Hz, 1H), 6.73 (d, J=7.6 Hz, 1H), 5.39 (d, J=13.2 Hz, 4H), 4.62-4.54 (m, 1H), 4.24 (d, J=12.3 Hz, 1H), 4.20-4.02 (m, 4H), 3.71-3.54 (m, 2H), 3.50-3.26 (m, 5H), 3.28-3.15 (m, 2H), 3.11-3.01 (m, 1H), 2.33-2.24 (m, 3H), 2.11 (s, 5H), 1.98-1.89 (m, 5H), 1.83-1.67 (m, 6H), 1.31 (t, J=7.3 Hz, 2H).

Example 3: Synthesis of (S)-1⁴-chloro-4⁵-cyano-1⁵-((3'-(3-((R)-3-hydroxypyrrolidin-1-yl)propoxy)-2,2'-dimethyl-[1,1'-biphenyl]-3-yl)methoxy)-5-oxo-2-oxa-6,12-diaza-1(1,2),4(1,3)-dibenze (S)-1⁴-chloro-4⁵-cyano-15-((3'-(3-((R)-3-hydroxypyrrolidin-1-yl)propoxy)-2,2'-dimethyl-[1,1'-biphenyl]-3-yl)methoxy)-5-oxo-2-oxa-6,12-diaza-1(1,2),4(1,3)-dibenzenacyclotridecaphane-11-carboxylic acid
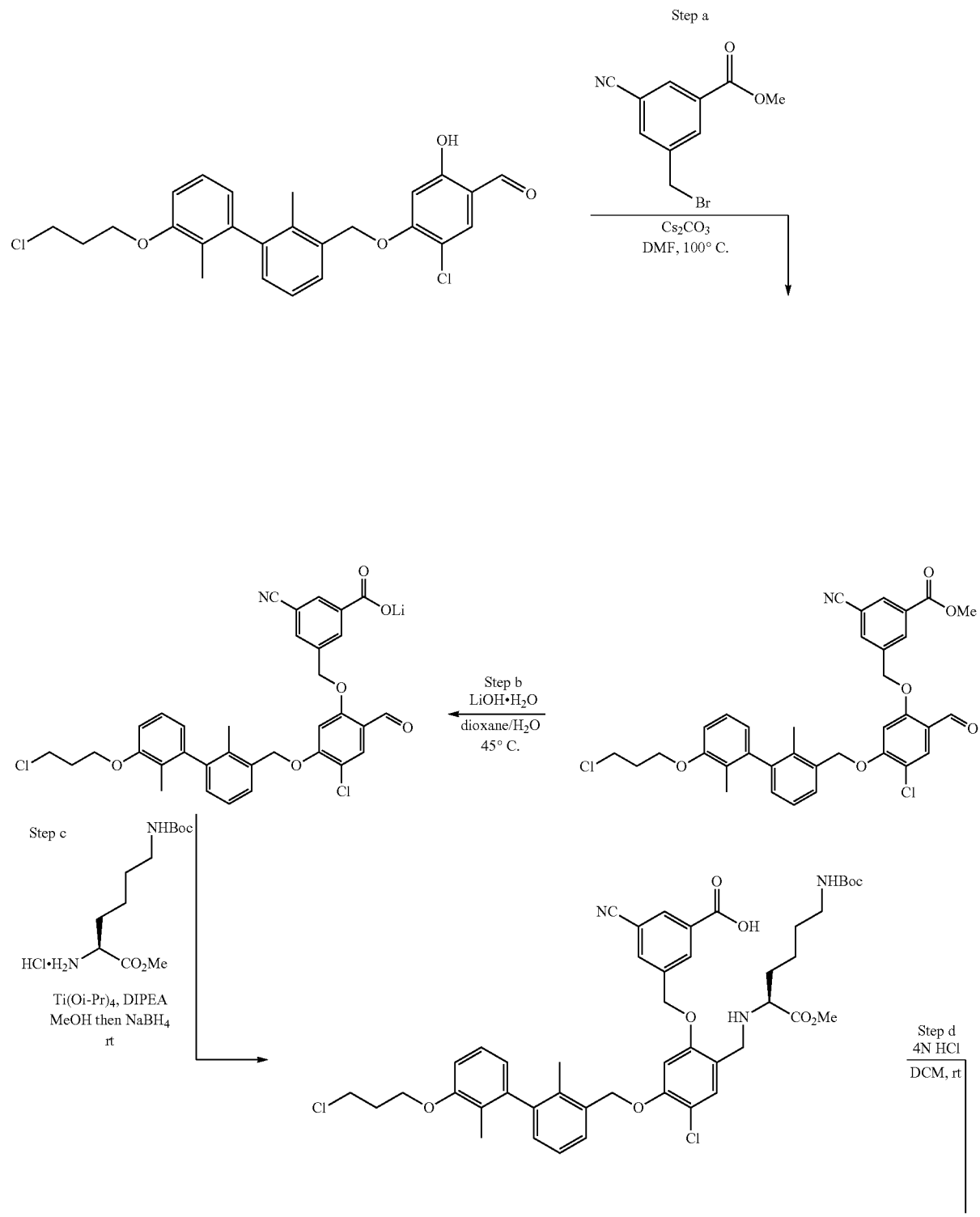

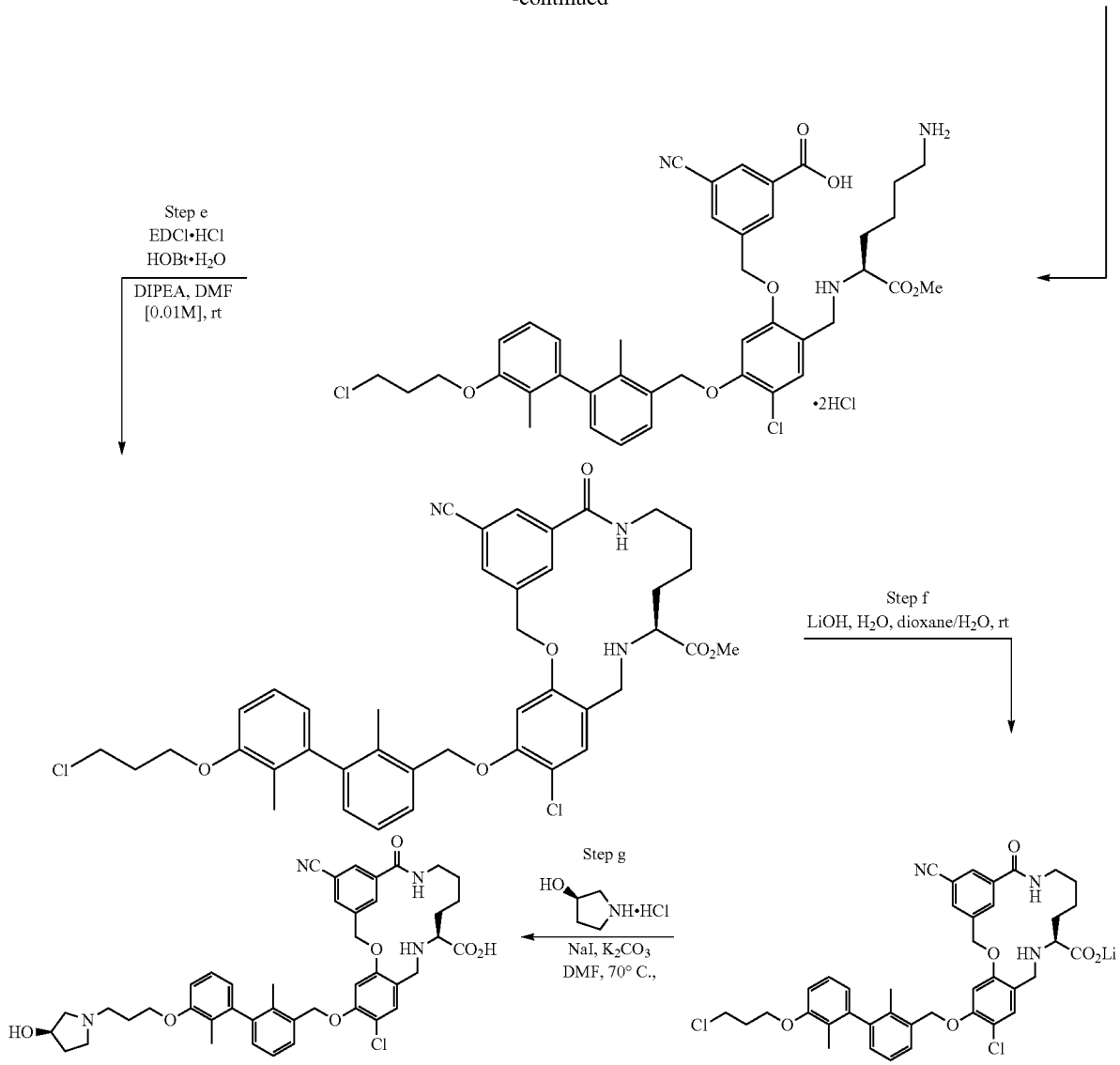

Step a: A mixture of 5-chloro-4-((3'-(3-chloropropoxy)-2,2'-dimethyl-[1,1'-biphenyl]-3-yl)methoxy)-2-hydroxybenzaldehyde (1.0 g, 2.18 mmol), methyl 3-(bromomethyl)-5-cyanobenzoate (0.63 g, 2.50 mmol), and cesium carbonate (1.77 g, 2.50 mmol) in DMF (7 mL) was stirred at 100° C. for 1.5 h. Water (20 mL) was added and the aqueous mixture was extracted with EtOAc (3×30 mL). The combined organic layers were dried over MgSO₄, filtered, and concentrated in vacuo. The crude material was purified by flash chromatography (SiO₂, 20% EtOAc in hexane to 100% EtOAc) to afford methyl 3-((4-chloro-5-((3'-(3-chloropropoxy)-2,2'-dimethyl-[1,1'-biphenyl]-3-yl)methoxy)-2-formylphenoxy)methyl)-5-cyanobenzoate.

Step b: To a biphasic solution of methyl 3-((4-chloro-5-((3'-(3-chloropropoxy)-2,2'-dimethyl-[1,1'-biphenyl]-3-yl)methoxy)-2-formylphenoxy)methyl)-5-cyanobenzoate (250 mg, 0.40 mmol) in dioxane (6 mL) and water (1 mL) was added lithium hydroxide monohydrate (25 mg, 0.60 mmol). The mixture was heated to 45° C. and allowed to stir for 2.5 h before it was frozen and lyophilized to afford lithium 3-((4-chloro-5-((3'-(3-chloropropoxy)-2,2'-dimethyl-[1,1'-biphenyl]-3-yl)methoxy)-2-formylphenoxy)methyl)-5-cyanobenzoate. The material was used in the subsequent step without purification.

Step c: To a solution of lithium 3-((4-chloro-5-((3'-(3-chloropropoxy)-2,2'-dimethyl-[1,1'-biphenyl]-3-yl)methoxy)-2-formylphenoxy)methyl)-5-cyanobenzoate (220 mg, 0.36 mmol) and N-Boc-L-lysine methyl ester hydrochloride (116 mg, 0.39 mmol) in MeOH (4 mL) was added N,N-diisopropylethylamine (100 μL, 0.53 mmol) and Ti(OiPr)₄ (160 μL, 0.53 mmol). The mixture was allowed to stir at room temperature for 16 h before sodium borohydride (54 mg, 1.42 mmol) was added in portions over 5 min. The reaction mixture was stirred for 15 min and then concentrated in vacuo. The crude material was purified by flash chromatography (SiO₂, 100% DCM to 20% MeOH in DCM) to afford (S)-3-((2-(((6-((tert-butoxycarbonyl)amino)-1-methoxy-1-oxohexan-2-yl)amino)methyl)-4-chloro-5-((3'-(3-chloropropoxy)-2,2'-dimethyl-[1,1'-biphenyl]-3-yl)methoxy)phenoxy)methyl)-5-cyanobenzoic acid.

Step d: To a solution of (S)-3-((2-(((6-((tert-butoxycarbonyl)amino)-1-methoxy-1-oxohexan-2-yl)amino)methyl)-4-chloro-5-((3'-(3-chloropropoxy)-2,2'-dimethyl-[1,1'-biphenyl]-3-yl)methoxy)phenoxy)methyl)-5-cyanobenzoic acid (146 mg, 0.17 mmol) in DCM (3 mL) was added 4 N HCl in dioxane (0.17 mL, 0.68 mmol). The mixture was allowed to stir at rt for 4 h before it was concentrated in vacuo to afford (S)-3-((2-(((6-amino-1-methoxy-1-oxohexan-2-yl)amino)methyl)-4-chloro-5-((3'-(3-chloropropoxy)-2,2'-dimethyl-[1,1'-biphenyl]-3-yl)methoxy)phenoxy)methyl)-5-cyanobenzoic acid hydrochloride salt. The material was used in the subsequent step without purification.

Step e: To a solution of ((S)-3-((2-(((6-amino-1-methoxy-1-oxohexan-2-yl)amino)methyl)-4-chloro-5-((3'-(3-chloropropoxy)-2,2'-dimethyl-[1,1'-biphenyl]-3-yl)methoxy)phenoxy)methyl)-5-cyanobenzoic acid hydrochloride salt (142 mg, 0.17 mmol) in DMF (17 mL) was added N-(3-dimethylaminopropyl)-N'-ethylcarbodiimide hydrochloride (130 mg, 0.68 mmol), 1-hydroxybenzotriazole hydrate (52 mg, 0.34 mmol), and N,N-diisopropylethylamine (300 µL, 1.7 mmol). The mixture was left to stir for 18 h and then concentrated in vacuo. The crude material was purified by flash chromatography (SiO$_2$, 5% MeOH in DCM) to afford methyl (S)-1$^4$-chloro-1$^5$-((3'-(3-chloropropoxy)-2,2'-dimethyl-[1,1'-biphenyl]-3-yl)methoxy)-4$^5$-cyano-5-oxo-2-oxa-6,12-diaza-1(1,2),4(1,3)-dibenzenacyclotridecaphane-11-carboxylate.

Step f: To a biphasic solution of methyl (S)-1$^4$-chloro-1$^5$-((3'-(3-chloropropoxy)-2,2'-dimethyl-[1,1'-biphenyl]-3-yl)methoxy)-4$^5$-cyano-5-oxo-2-oxa-6,12-diaza-1(1,2),4(1,3)-dibenzenacyclotridecaphane-11-carboxylate (116 mg, 0.156 mmol) in dioxane (2 mL) and water (1 mL) was added lithium hydroxide monohydrate (7 mg, 0.17 mmol). After stirring at room temperature for 3 h, the reaction mixture was frozen and lyophilized to afford lithium (S)-1$^4$-chloro-1$^5$-((3'-(3-chloropropoxy)-2,2'-dimethyl-[1,1'-biphenyl]-3-yl)methoxy)-4$^5$-cyano-5-oxo-2-oxa-6,12-diaza-1(1,2),4(1,3)-dibenzenacyclotridecaphane-11-carboxylate. The material was used in the subsequent step without purification.

Step g: To a solution of lithium (S)-1$^4$-chloro-1$^5$-((3'-(3-chloropropoxy)-2,2'-dimethyl-[1,1'-biphenyl]-3-yl)methoxy)-4$^5$-cyano-5-oxo-2-oxa-6,12-diaza-1(1,2),4(1,3)-dibenzenacyclotridecaphane-11-carboxylate (35 mg, 0.048 mmol) in DMF (1 mL) was added (R)-pyrrolidin-3-ol hydrochloride salt (10 mg, 0.081 mmol), K$_2$CO$_3$ (38 mg, 0.27 mmol) and NaI (3 mg, 0.02 mmol). The resulting suspension was stirred at 70° C. for 18 h. The reaction mixture was filtered, and the filtrate was concentrated in vacuo. The crude material was purified by reverse phase preparative HPLC (CH$_3$CN—H$_2$O with 0.1% TFA) to obtain (S)-1$^4$-chloro-4$^5$-cyano-15-((3'-(3-((R)-3-hydroxypyrrolidin-1-yl)propoxy)-2,2'-dimethyl-[1,1'-biphenyl]-3-yl)methoxy)-5-oxo-2-oxa-6,12-diaza-1(1,2),4(1,3)-dibenzenacyclotridecaphane-11-carboxylic acid as a trifluoroacetate salt. MS: (ES) m/z calculated for C$_{44}$H$_{49}$ClN$_4$O$_7$ [M+H]$^+$ 781.3, found 781.5. $^1$H NMR (400 MHz, Methanol-d$_4$) δ 8.28 (s, 1H), 7.94 (s, 1H), 7.83 (s, 1H), 7.55 (s, 1H), 7.43 (d, J=7.6 Hz, 1H), 7.18 (t, J=7.7 Hz, 1H), 7.14 (t, J=8.1 Hz, 1H), 7.02 (s, 1H), 7.00 (d, J=7.7 Hz, 1H), 6.88 (d, J=8.3 Hz, 1H), 6.65 (d, J=7.6 Hz, 1H), 5.29 (s, 4H), 4.55-4.40 (m, 2H), 4.18 (d, J=13.1 Hz, 1H), 4.15-4.05 (m, 2H), 3.90 (t, J=6.6 Hz, 1H), 3.84-3.62 (m, 1H), 3.59-3.43 (m, 2H), 3.43-3.27 (m, 2H), 3.14-2.99 (m, 2H), 2.90 (d, J=12.4 Hz, 1H), 2.37-2.10 (m, 4H), 2.10-2.01 (m, 4H), 2.00-1.89 (m, 2H), 1.85 (d, J=2.1 Hz, 3H), 1.67-1.54 (m, 4H).

Example 4: Synthesis of (S)-2$^4$-chloro-2$^5$-((2-methyl-[1,1'-biphenyl]-3-yl)methoxy)-11-oxo-4,10-diaza-1(3,5)-pyridina-2(1,2)-benzenacycloundecaphane-5-carboxylic acid

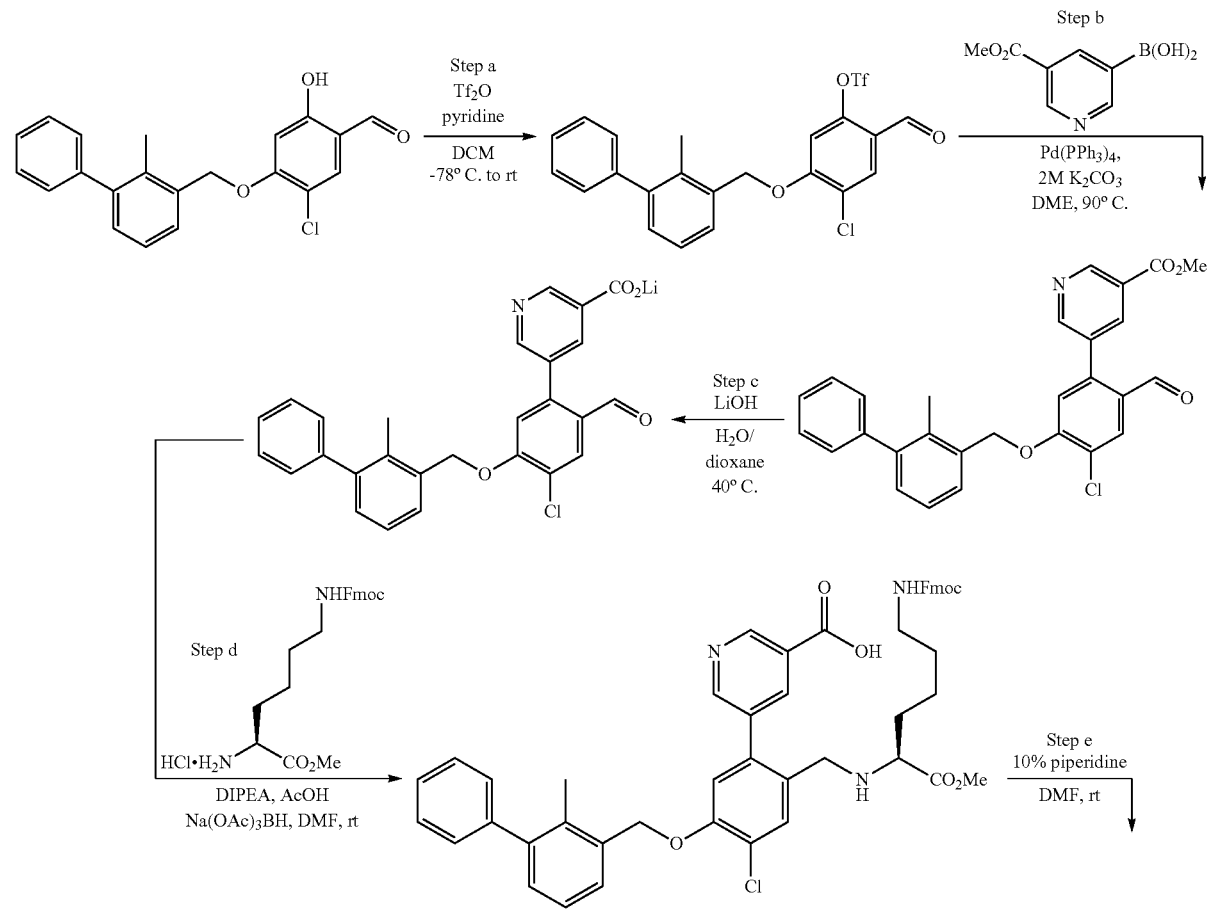

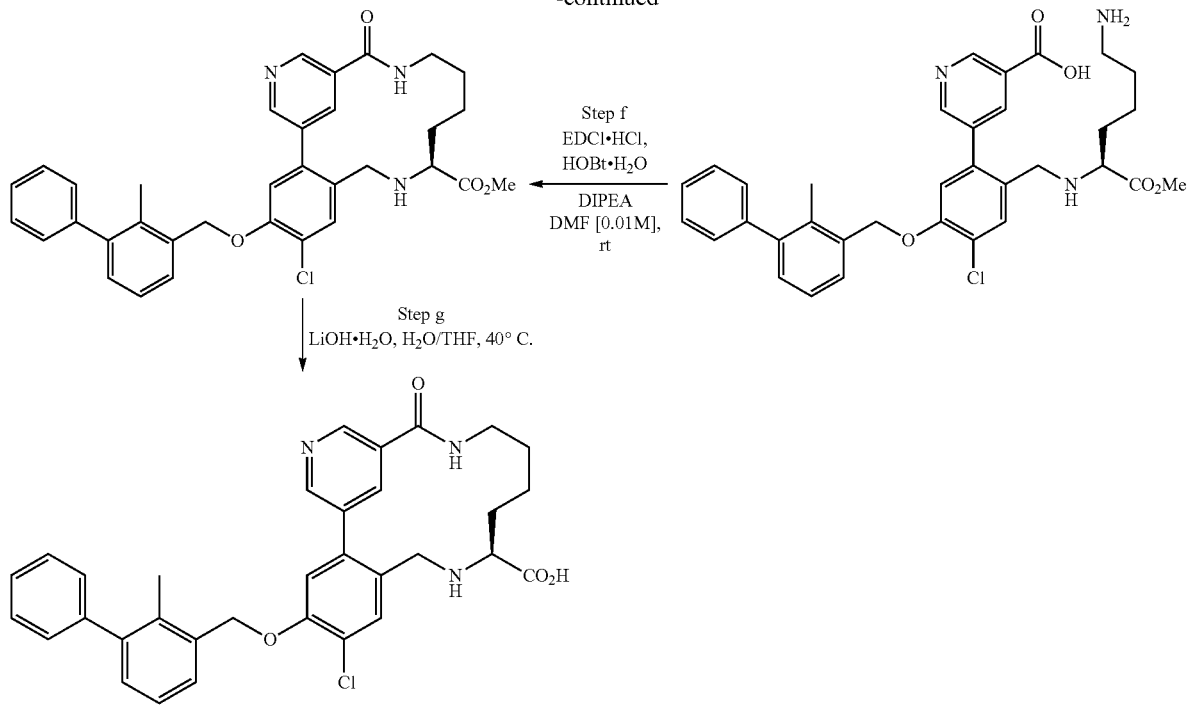

Step a: To a cooled (−78° C.) solution of 5-chloro-2-hydroxy-4-((2-methyl-[1,1'-biphenyl]-3-yl)methoxy)benzaldehyde (0.42 g, 1.2 mmol) in DCM (20 mL) under nitrogen was slowly added pyridine (0.5 mL) and trifluoromethansulfonic anhydride (0.4 mL, 2.4 mmol). The solution was allowed to gradually warm to room temperature and stir for 3 h. The reaction was carefully quenched by the slow addition of saturated aqeuous NaHCO₃ until gas evolution subsided. Water (30 mL) was added and the aqueous mixture was extracted with DCM (2×25 mL). The combined organic layers were dried over MgSO₄, filtered, and concentrated in vacuo. The crude product was purified by flash chromatography (SiO₂, 100% hexane to 30% EtOAc in hexane) to afford 4-chloro-2-formyl-5-((2-methyl-[1,1'-biphenyl]-3-yl)methoxy)phenyl trifluoromethanesulfonate.

Step b: A solution of 4-chloro-2-formyl-5-((2-methyl-[1,1'-biphenyl]-3-yl)methoxy)phenyl trifluoromethanesulfonate (180 mg, 0.37 mmol), (5-(methoxycarbonyl)pyridin-3-yl)boronic acid (81 mg, 0.44 mmol), and aqueous 2 M K₂CO₃ (0.4 mL, 0.20 mmol) in 1,2-dimethoxyethane (1.5 mL) was degassed with nitrogen for 10 min before Pd(PPh₃)₄ (85 mg, 0.074 mmol) was added. After degassing for an additional 5 min, the solution was heated to 80° C. and allowed to stir for 1 h. After cooling to rt, water (5 mL) was added to the reaction mixture and the mixture was extracted with EtOAc (5 mL×2). The combined organic layers were dried over MgSO₄, filtered, and concentrated in vacuo. Purification of the crude material by flash chromatography (SiO₂, 100% hexane to 40% EtOAc in hexane) gave methyl 5-(4-chloro-2-formyl-5-((2-methyl-[1,1'-biphenyl]-3-yl)methoxy)phenyl)nicotinate.

Step c: To a biphasic solution of methyl 5-(4-chloro-2-formyl-5-((2-methyl-[1,1'-biphenyl]-3-yl)methoxy)phenyl)nicotinate (121 mg, 0.26 mmol) in dioxane (4 mL) and water (1 mL) was added lithium hydroxide monohydrate (16 mg, 0.39 mmol). The mixture was heated to 40° C. and allowed to stir for 30 min, at which time the reaction was complete. The crude reaction mixture was frozen and lyophilized to afford crude lithium 5-(4-chloro-2-formyl-5-((2-methyl-[1,1'-biphenyl]-3-yl)methoxy)phenyl)nicotinate, which was used in the subsequent step without purification.

Step d: To a solution of lithium 5-(4-chloro-2-formyl-5-((2-methyl-[1,1'-biphenyl]-3-yl)methoxy)phenyl)nicotinate (117 mg, 0.26 mmol) and N-Fmoc-L-lysine methyl ester hydrochloride salt (430 mg, 1.02 mmol) in DMF (6 mL) was added acetic acid (50 µL, 0.88 mmol) and N,N-diisopropylethylamine (177 µL, 1.02 mmol). The mixture was allowed to stir at room temperature for 30 min before sodium triacetoxyborohydride (163 mg, 0.77 mmol) was added in portions over 5 min. The reaction mixture was stirred at room temperature for 18 h, before the mixture was concentrated in vacuo. The crude material was re-diluted in MeOH, passed through a 0.45 µM syringe filter, and purified by reverse phase preparative HPLC (CH₃CN—H₂O with 0.1% TFA) to obtain (S)-5-(2-(((6-((((9H-fluoren-9-yl)methoxy)carbonyl)amino)-1-methoxy-1-oxohexan-2-yl)amino)methyl)-4-chloro-5-((2-methyl-[1,1'-biphenyl]-3-yl)methoxy)phenyl)nicotinic acid as a trifluoroacetate salt.

Step e: (S)-5-((2-(((6-(((((9H-fluoren-9-yl)methoxy)carbonyl)amino)-1-methoxy-1-oxohexan-2-yl)amino)methyl)-4-chloro-5-((2-methyl-[1,1'-biphenyl]-3-yl)methoxy)phenoxy)methyl)nicotinic acid (46 mg, 0.054 mmol) was dissolved in 10% piperidine in DMF (1.8 mL), and the solution was stirred at room temperature for 15 min. The mixture was then concentrated in vacuo to afford (S)-5-(2-(((6-amino-1-methoxy-1-oxohexan-2-yl)amino)methyl)-4-chloro-5-((2-methyl-[1,1'-biphenyl]-3-yl)methoxy)phenyl)nicotinic acid, which was used without further purification.

Step f: To a solution of (S)-5-(2-(((6-amino-1-methoxy-1-oxohexan-2-yl)amino)methyl)-4-chloro-5-((2-methyl-[1,1'-biphenyl]-3-yl)methoxy)phenyl)nicotinic acid in DMF (6.2 mL) was added N-(3-dimethylaminopropyl)-N'-ethylcarbodiimide hydrochloride (50 mg, 0.25 mmol), 1-hydroxybenzotriazole hydrate (20 mg, 0.125 mmol), and N,N-diisopropylethylamine (110 µL, 0.62 mmol). The mixture was left to stir for 18 h at rt and then concentrated in vacuo. The crude material was purified by flash chromatography (SiO$_2$, 10% MeOH in DCM) to afford methyl (S)-2$^4$-chloro-2$^5$-((2-methyl-[1,1'-biphenyl]-3-yl)methoxy)-11-oxo-4,10-diaza-1(3,5)-pyridina-2(1,2)-benzenacycloundecaphane-5-carboxylate.

Step g: To a biphasic solution of methyl (S)-2$^4$-chloro-2$^5$-((2-methyl-[1,1'-biphenyl]-3-yl)methoxy)-11-oxo-4,10-diaza-1(3,5)-pyridina-2(1,2)-benzenacycloundecaphane-5-carboxylate (20 mg, 0.034 mmol) in dioxane (1 mL) and water (0.5 mL) was added lithium hydroxide monohydrate (19 mg, 0.45 mmol), and the mixture was heated to 40° C. After 1 h, the crude reaction mixture was passed through a 0.45 µM syringe filter and purified by reverse phase preparative HPLC (CH$_3$CN—H$_2$O with 0.1% TFA) to obtain (S)-2$^4$-chloro-2$^5$-((2-methyl-[1,1'-biphenyl]-3-yl)methoxy)-11-oxo-4,10-diaza-1(3,5)-pyridina-2(1,2)-benzenacycloundecaphane-5-carboxylic acid. MS: (ES) m/z calculated for C$_{33}$H$_{32}$ClN$_3$O$_4$ [M+H]$^+$ 570.2, found 570.1. $^1$H NMR (400 MHz, DMSO-d$_6$) δ 9.02 (s, 1H), 8.87 (s, 1H), 8.76 (s, 1H), 8.62 (br s, 1H), 7.59-7.40 (m, 2H), 7.40-7.24 (m, 2H), 7.19 (s, 2H), 7.06 (s, 2H), 6.93 (s, 2H), 5.48-5.25 (m, 2H), 3.76-3.48 (m, 2H), 3.12-2.92 (m, 2H), 2.85-2.69 (m, 1H), 2.22 (s, 3H), 1.98-1.79 (m, 1H), 1.73-1.31 (m, 5H).

Example 5: Synthesis of (S)-4$^4$-chloro-7-(hydroxymethyl)-4$^5$-((3'-(3-(4-hydroxypiperidin-1-yl)propoxy)-2,2'-dimethyl-[1,1'-biphenyl]-3-yl)methoxy)-3-oxa-6,12-diaza-1(3,5)-pyridina-4(1,2)-benzenacyclotridecaphan-13-one

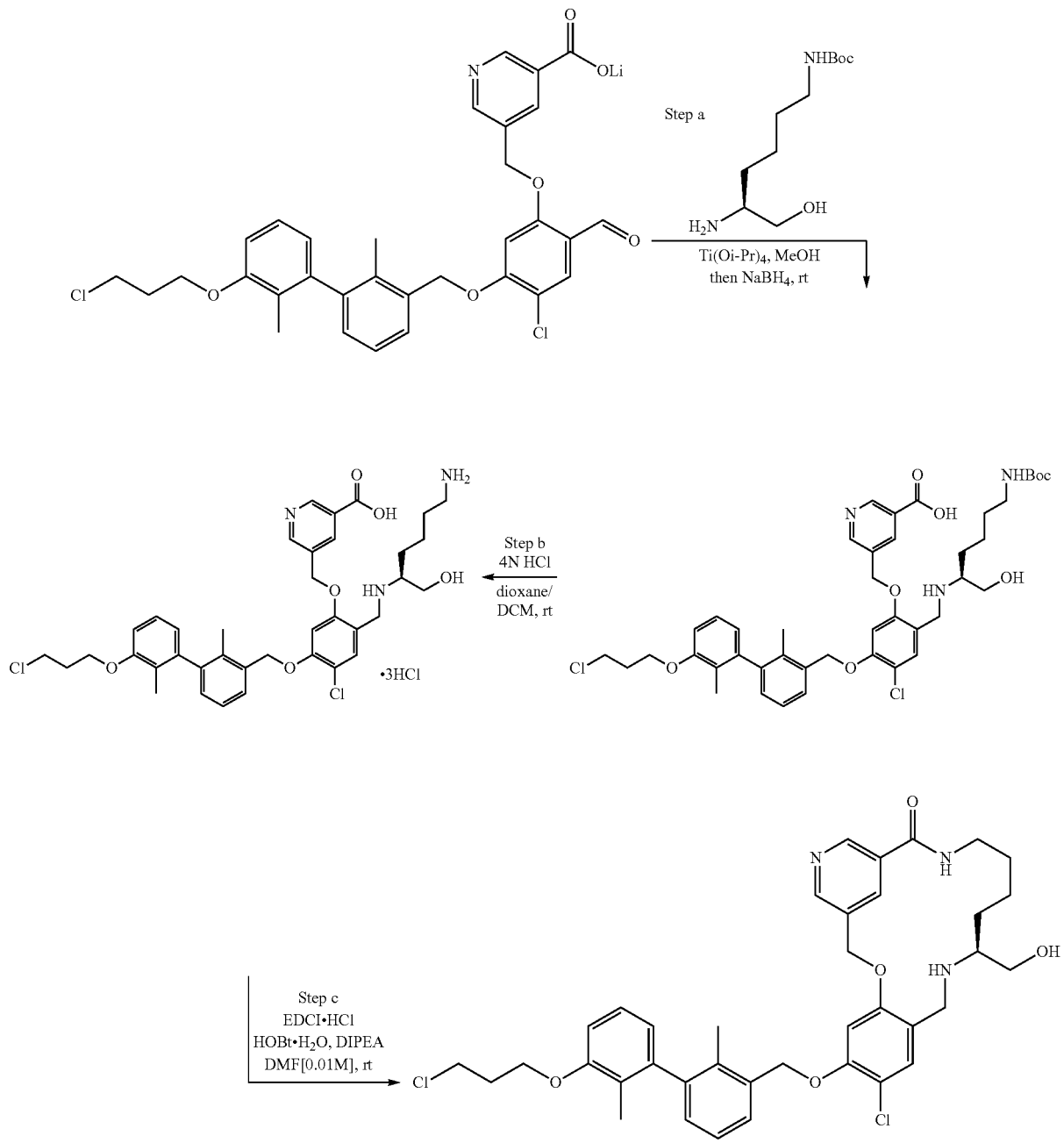

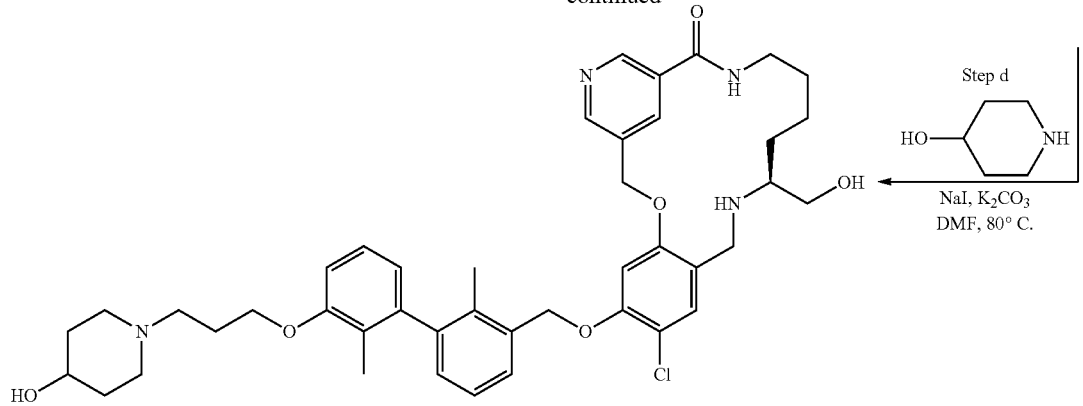

-continued

Step a: To a solution of lithium 5-((4-chloro-5-((3'-(3-chloropropoxy)-2,2'-dimethyl-[1,1'-biphenyl]-3-yl)methoxy)-2-formylphenoxy)methyl)nicotinate (250 mg, 0.42 mmol) and tert-butyl (S)-(5-amino-6-hydroxyhexyl)carbamate (116 mg, 0.39 mmol) in MeOH (4 mL) was added Ti(Oi-Pr)$_4$ (185 μL, 0.63 mmol). The mixture was allowed to stir at rt for 7 h before sodium borohydride (117 mg, 3.08 mmol) was added in portions over 5 min. The reaction mixture was stirred for 30 min and then concentrated in vacuo. The crude material was purified by flash chromatography (SiO$_2$, 100% DCM to 20% MeOH in DCM) to afford ((S)-5-((2-(((6-((tert-butoxycarbonyl)amino)-1-hydroxyhexan-2-yl)amino)methyl)-4-chloro-5-((3'-(3-chloropropoxy)-2,2'-dimethyl-[1,1'-biphenyl]-3-yl)methoxy)phenoxy)methyl)nicotinic acid.

Step b: To a solution of ((S)-5-((2-(((6-((tert-butoxycarbonyl)amino)-1-hydroxyhexan-2-yl)amino)methyl)-4-chloro-5-((3'-(3-chloropropoxy)-2,2'-dimethyl-[1,1'-biphenyl]-3-yl)methoxy)phenoxy)methyl)nicotinic acid (286 mg, 0.35 mmol) in DCM (6 mL) was added 4 N HCl in dioxane (0.35 mL, 1.41 mmol). The mixture was allowed to stir at rt for 4 h before it was concentrated in vacuo to afford (S)-5-((2-(((6-amino-1-hydroxyhexan-2-yl)amino)methyl)-4-chloro-5-((3'-(3-chloropropoxy)-2,2'-dimethyl-[1,1'-biphenyl]-3-yl)methoxy)phenoxy)methyl)nicotinic acid hydrochloride salt. The material was used in the subsequent step without purification.

Step c: To a solution of (S)-5-((2-(((6-amino-1-hydroxyhexan-2-yl)amino)methyl)-4-chloro-5-((3'-(3-chloropropoxy)-2,2'-dimethyl-[1,1'-biphenyl]-3-yl)methoxy)phenoxy)methyl)nicotinic acid hydrochloride salt (167 mg, 0.20 mmol) in DMF (20 mL) was added N-(3-dimethylaminopropyl)-N'-ethylcarbodiimide hydrochloride (153 mg, 0.81 mmol), 1-hydroxybenzotriazole hydrate (61 mg, 0.40 mmol), and N,N-diisopropylethylamine (420 μL, 2.40 mmol). The mixture was left to stir for 3 d at rt and then concentrated in vacuo. The crude material was re-diluted in MeOH, passed through a 0.45 μM syringe filter and purified by reverse phase preparative HPLC (CH$_3$CN—H$_2$O with 0.1% TFA) to obtain (S)-4$^4$-chloro-4$^5$-((3'-(3-chloropropoxy)-2,2'-dimethyl-[1,1'-biphenyl]-3-yl)methoxy)-7-(hydroxymethyl)-3-oxa-6,12-diaza-1(3,5)-pyridina-4(1,2)-benzenacyclotridecaphan-13-one as a trifluoroacetate salt.

Step d: To a solution of (S)-4$^4$-chloro-4$^5$-((3'-(3-chloropropoxy)-2,2'-dimethyl-[1,1'-biphenyl]-3-yl)methoxy)-7-(hydroxymethyl)-3-oxa-6,12-diaza-1(3,5)-pyridina-4(1,2)-benzenacyclotridecaphan-13-one trifluoroacetate salt (39 mg, 0.044 mmol) in DMF (1 mL) was added 4-hydroxypiperidine (7 mg, 0.066 mmol), K$_2$CO$_3$ (24 mg, 0.18 mmol), and NaI (2 mg, 0.013 mmol). The resulting suspension was stirred at 80° C. for 12 h. The reaction mixture was filtered and concentrated in vacuo. The crude material was purified by reverse phase preparative HPLC (CH$_3$CN—H$_2$O with 0.1% TFA) to obtain (S)-4$^4$-chloro-7-(hydroxymethyl)-4$^5$-((3'-(3-(4-hydroxypiperidin-1-yl)propoxy)-2,2'-dimethyl-[1,1'-biphenyl]-3-yl)methoxy)-3-oxa-6,12-diaza-1(3,5)-pyridina-4(1,2)-benzenacyclotridecaphan-13-one as a trifluoroacetate salt. MS: (ES) m/z calculated for C$_{43}$H$_{53}$ClN$_4$O$_6$ [M+H]$^+$ 757.4, found 757.7. $^1$H NMR (400 MHz, Methanol-d$_4$) δ 8.81 (d, J=2.1 Hz, 1H), 8.70 (d, J=2.0 Hz, 1H), 8.48 (dt, J=2.2, 1.1 Hz, 1H), 7.49 (dd, J=7.7, 1.7 Hz, 1H), 7.40 (s, 1H), 7.23 (t, J=7.6 Hz, 1H), 7.21-7.13 (m, 1H), 7.06 (dd, J=7.6, 1.4 Hz, 1H), 7.01 (d, J=3.5 Hz, 1H), 6.92 (d, J=8.3 Hz, 1H), 6.68 (d, J=37.7 Hz, 1H), 5.32 (s, 2H), 5.30 (s, 2H), 4.19 (d, J=11.8 Hz, 1H), 4.08 (tq, J=6.3, 3.5 Hz, 2H), 3.71 (dd, J=11.2, 4.1 Hz, 1H), 3.69-3.61 (m, 2H), 3.62-3.43 (m, 2H), 2.96-2.84 (m, 2H), 2.84-2.73 (m, 1H), 2.69-2.59 (m, 2H), 2.33-2.17 (m, 2H), 2.10 (d, J=1.4 Hz, 3H), 2.09-1.98 (m, 3H), 1.93-1.81 (m, 4H), 1.80-1.66 (m, 5H), 1.66-1.48 (m, 5H).

Example 6: Synthesis of (S)-16-chloro-17-((2-methyl-[1,1'-biphenyl]-3-yl)methoxy)-6-oxo-3,4,5,6,7,8,9,10,11,12,13,14-dodecahydro-2H-benzo[b][1]oxa[5,11]diazacyclohexadecine-12-carboxylic acid

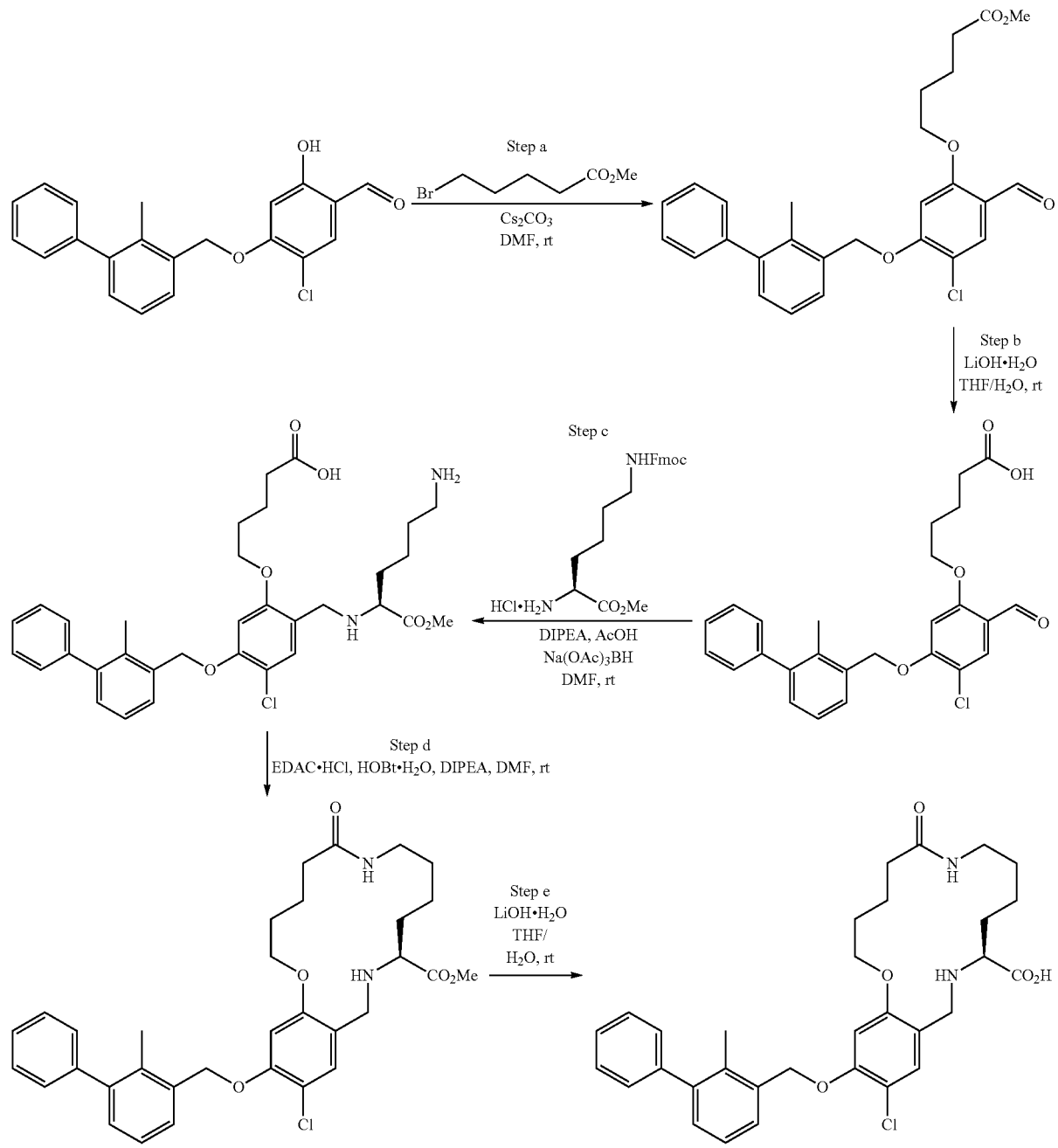

Step a: Methyl 5-bromovalerate (0.18 mL, 1.2 mmol) was added dropwise with stirring to a mixture of 5-chloro-2 hydroxy-4-((2-methyl-[1,1'-biphenyl]-3-yl)methoxybenzaldehyde (353 mg, 1.0 mmol) and cesium carbonate (652 mg, 2.0 mmol) in DMF (2 mL). The mixture was stirred at room temperature overnight. The reaction mixture was diluted with water (20 mL) and extracted with EtOAc (3×20 mL). The combined organic layers were washed with brine (20 mL), dried over MgSO$_4$, filtered, and concentrated. Purification by flash chromatography on silica (0-50% EtOAc/ hexanes) gave methyl 5-(4-chloro-2-formyl-5-((2-methyl-[1,1'-biphenyl]-3-yl)methoxy)phenoxy)pentanoate.

Step b: To a stirred solution of methyl 5-(4-chloro-2-formyl-5-((2-methyl-[1,1'-biphenyl]-3-yl)methoxy)phenoxy)pentanoate (280 mg, 0.60 mmol) in THF (8 mL) was added a solution of lithium hydroxide monohydrate (76 mg, 1.8 mmol) in water (2 mL). The reaction mixture was stirred at room temperature overnight. The reaction mixture was diluted with 1 M HCl (10 mL) and extracted with EtOAc (3×10 mL). The combined organic layers were washed with brine (10 mL), dried over MgSO₄, filtered, and concentrated to give 5-(4-chloro-2-formyl-5-((2-methyl-[1,1'-biphenyl]-3-yl)methoxy)phenoxy)pentanoic acid, which was used without further purification.

Step c: To a solution of 5-(4-chloro-2-formyl-5-((2-methyl-[1,1'-biphenyl]-3-yl)methoxy)phenoxy)pentanoic acid (254 mg, 0.56 mmol) and N'-Fmoc-L-lysine methyl ester hydrochloride (1.7 g, 2.8 mmol) in DMF (5 mL) was added N,N-diisopropylethylamine (0.5 mL). The mixture was stirred at room temperature, and sodium triacetoxyborohydride (361 mg, 1.7 mmol) was added slowly in portions. The reaction mixture was stirred at room temperature overnight. Purification by preparative HPLC (H₂O/MeCN, with 0.1% TFA) gave (S)-5-(2-(((6-amino-1-methoxy-1-oxohexan-2-yl)amino)methyl)-4-chloro-5-((2-methyl-[1,1'-biphenyl]-3-yl)methoxy)phenoxy)pentanoic acid as the bis-TFA salt.

Step d: To a stirred solution of (S)-5-(2-(((6-amino-1-methoxy-1-oxohexan-2-yl)amino)methyl)-4-chloro-5-((2-methyl-[1,1'-biphenyl]-3-yl)methoxy)phenoxy)pentanoic acid (62 mg, 0.075 mmol) in DMF (7.5 mL) were added N,N-diisopropylethylamine (0.13 mL, 0.75 mmol), 1-hydroxybenzotriazole hydrate (23 mg, 0.15 mmol), and N-(3-dimethylaminopropyl)-N'-ethylcarbodiimide hydrochloride (58 mg, 0.30 mmol). The reaction mixture was stirred at room temperature overnight, then concentrated. Purification by preparative HPLC (H₂O/MeCN, with 0.1% TFA) gave methyl (S)-16-chloro-17-((2-methyl-[1,1'-biphenyl]-3-yl)methoxy)-6-oxo-3,4,5,6,7,8,9,10,11,12,13,14-dodecahydro-2H-benzo[b][1]oxa[5,11]diazacyclohexadecine-12-carboxylate as the TFA salt.

Step e: To a stirred solution of methyl (S)-16-chloro-17-((2-methyl-[1,1'-biphenyl]-3-yl)methoxy)-6-oxo-3,4,5,6,7,8,9,10,11,12,13,14-dodecahydro-2H-benzo[b][1]oxa[5,11]diazacyclohexadecine-12-carboxylate (10 mg, 0.015 mmol) in THF (0.8 mL) was added a solution of lithium hydroxide monohydrate (3 mg, 0.060 mmol) in water (0.2 mL). The reaction mixture was stirred at room temperature overnight. Purification by preparative HPLC (H₂O/MeCN, with 0.1% TFA) gave (S)-16-chloro-17-((2-methyl-[1,1'-biphenyl]-3-yl)methoxy)-6-oxo-3,4,5,6,7,8,9,10,11,12,13,14-dodecahydro-2H-benzo[b][1]oxa[5,11]diazacyclohexadecine-12-carboxylic acid as the TFA salt. MS: (ES) m/z calculated for $C_{32}H_{38}ClN_2O_5$ $[M+H]^+$ 565.2, found 565.2. ¹H NMR (400 MHz, DMSO-d₆) δ 8.90 (br s, 2H), 7.81 (t, 1H, J=5.6 Hz), 7.52 (dd, 1H, J=1.2, 7.6 Hz), 7.48-7.41 (m, 3H), 7.39-7.34 (m, 1H), 7.32-7.26 (m, 3H), 7.21 (dd, 1H, J=1.2, 8.0 Hz), 5.31 (s, 2H), 4.20-4.10 (m, 2H), 4.04-3.94 (m, 2H), 3.90-3.84 (m, 1H), 3.23-3.12 (m, 1H), 3.09-2.98 (m, 1H), 2.22 (s, 3H), 2.18-2.07 (m, 2H), 2.04-1.93 (m, 1H), 1.92-1.82 (m, 1H), 1.79-1.66 (m, 4H), 1.53-1.40 (m, 3H), 1.34-1.20 (m, 1H).

Reverse phase HPLC conditions used for determination of retention times in Table 1:
Column: ZORBAX (SB-C18 2.1×50 mm, 5 µm)
Mobile phase A: 95% H₂O, 5% MeCN (with 0.1% Formic Acid)
Mobile phase B: 5% H₂O, 95% MeCN (with 0.1% Formic Acid)
Flow rate: 1.0 mL/min
Gradient: 20 to 100% B in 3.5 min Example 7: Enzyme-Linked Immunosorbent Assay—ELISA 96 Well plates were coated with 1 µg/mL of human PD-L1 (obtained from R&D) in PBS overnight at 4° C. The wells were then blocked with 2% BSA in PBS (W/V) with 0.05% TWEEN-20 for 1 hour at 37° C. The plates were washed 3 times with PBS/0.05% TWEEN-20 and the compounds were serial diluted (1:5) in dilution medium and added to the ELISA plates. Human PD-1 and biotin 0.3 µg/mL (ACRO Biosystems) were added and incubated for 1 hour at 37° C. then washed 3 times with PBS/0.05% TWEEN-20. A second block was performed with 2% BSA in PBS (W/V)/0.05% TWEEN-20 for 10 min at 37° C. and was washed 3 times with PBS/0.05% TWEEN-20. Streptavidin—HRP was added for 1 hour at 37° C. then washed 3 times with PBS/0.05% TWEEN-20. TMB substrate was added and reacted for 20 min at 37° C. A stop solution (2 N aqueous H₂SO₄) was added. The absorbance was read at 450 nm using a micro-plate spectrophotometer. The results are shown in Table 1.

Compounds in Table 1 were prepared by methods as described in the Examples and evaluated according to the assay above. The $IC_{50}$ of the compounds are presented in Table 1 as follows:
+, 20000 nM≥$IC_{50}$≥500 nM;
++, 500 nM>$IC_{50}$≥100 nM;
+++, 100 nM>$IC_{50}$.

TABLE 1

| Compound Id | Structure | ELISA $IC_{50}$ (nM) | MS $(M+H)^+$ | RP-HPLC $R_t$ (min) |
|---|---|---|---|---|
| 1.001 | 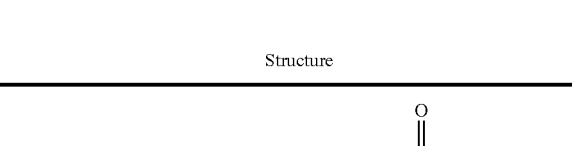 | +++ | 648.2 | 2.1 |

TABLE 1-continued

| Compound Id | Structure | ELISA IC$_{50}$ (nM) | MS (M + H)$^+$ | RP-HPLC R$_t$ (min) |
|---|---|---|---|---|
| 1.002 | 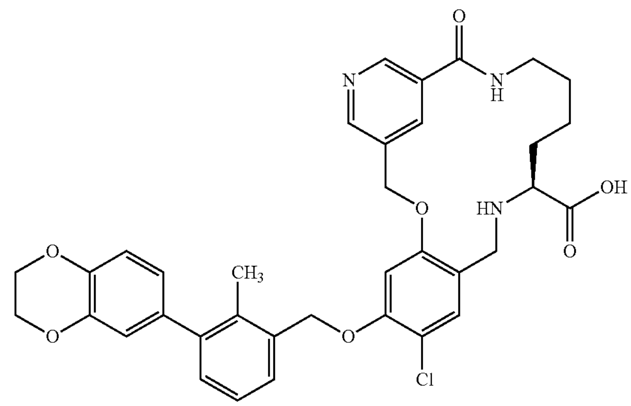 [SMILES: Cc1c(COc2cc3c(cc2Cl)CN[C@H](C(=O)O)CCCCNC(=O)c2cncc(c2)CO3)cccc1-c1ccc2c(c1)OCCO2] | +++ | 658.2 | 2.3 |
| 1.003 | 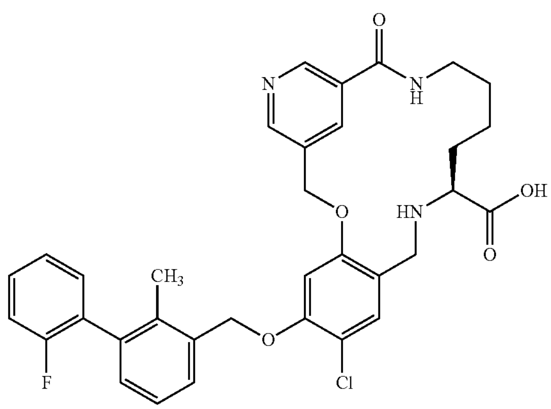 [SMILES: Cc1c(COc2cc3c(cc2Cl)CN[C@H](C(=O)O)CCCCNC(=O)c2cncc(c2)CO3)cccc1-c1ccccc1F] | +++ | 618.2 | 2.3 |
| 1.004 | 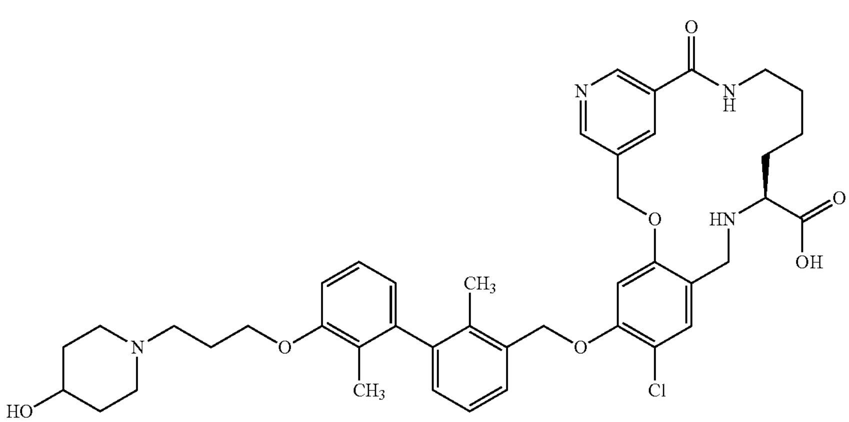 [SMILES: Cc1c(COc2cc3c(cc2Cl)CN[C@H](C(=O)O)CCCCNC(=O)c2cncc(c2)CO3)cccc1-c1cccc(OCCCN2CCC(O)CC2)c1C] | +++ | 771.6 | 1.6 |

TABLE 1-continued
| Compound Id | Structure | ELISA IC$_{50}$ (nM) | MS (M + H)$^+$ | RP-HPLC R$_t$ (min) |
|---|---|---|---|---|
| 1.005 | 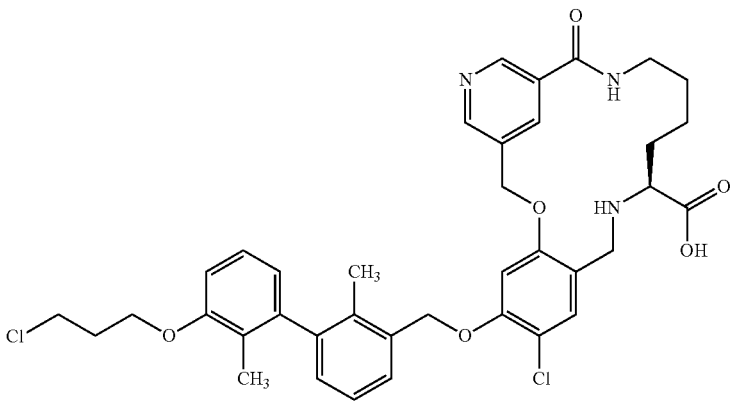 [SMILES: Cc1c(COc2cc3c(cc2Cl)CN[C@H](C(=O)O)CCCCNC(=O)c2cncc(c2)CO3)cccc1-c1cccc(OCCCCl)c1C] | + | 706.2 | 2.6 |
| 1.006 | 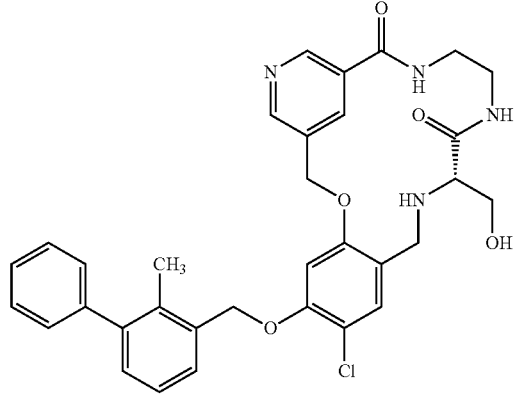 [SMILES: Cc1c(COc2cc3c(cc2Cl)CN[C@@H](CO)C(=O)NCCNC(=O)c2cncc(c2)CO3)cccc1-c1ccccc1] | ++ | 601.2 | 2.1 |
| 1.007 | 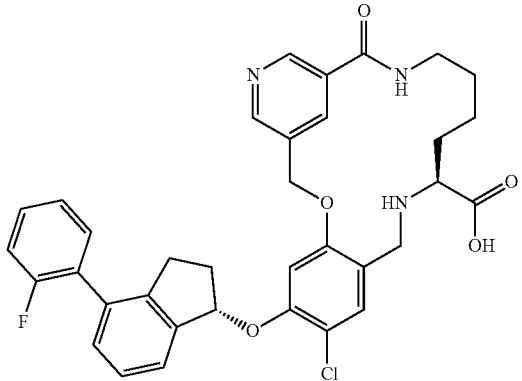 [SMILES: O=C1NCCCC[C@@H](C(=O)O)NCc2cc(Cl)c(O[C@H]3CCc4c(-c5ccccc5F)cccc43)cc2OCc2cncc1c2] | ++ | 630.2 | 2.3 |

TABLE 1-continued

| Compound Id | Structure | ELISA IC$_{50}$ (nM) | MS (M + H)$^+$ | RP-HPLC R$_t$ (min) |
|---|---|---|---|---|
| 1.008 | 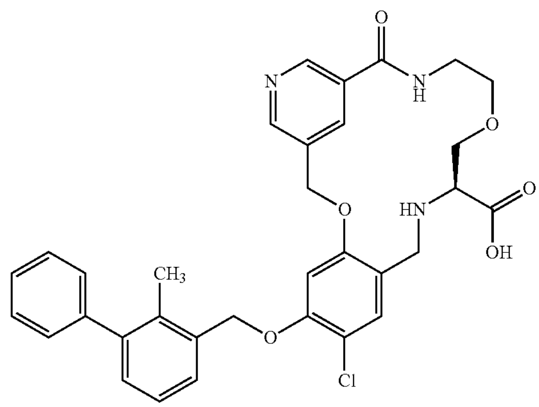 | ++ | 602.1 | 2.3 |
| 1.009 | 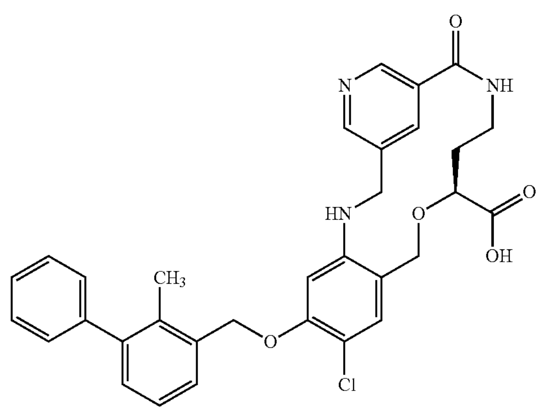 [SMILES: Cc1c(COc2cc3c(cc2Cl)CO[C@H](C(=O)O)CCNC(=O)c2cncc(c2)CN3)cccc1-c1ccccc1] | + | 572.1 | 2.3 |
| 1.010 | 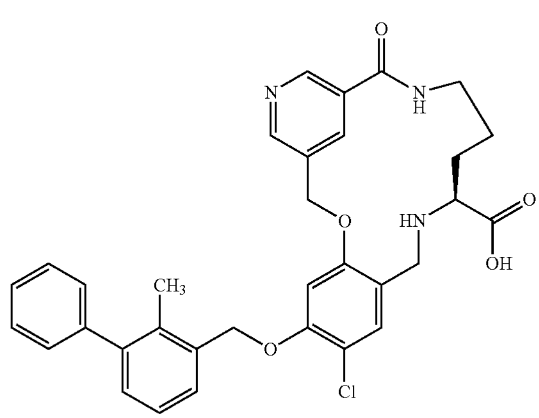 [SMILES: Cc1c(COc2cc3c(cc2Cl)CN[C@H](C(=O)O)CCCNC(=O)c2cncc(c2)CO3)cccc1-c1ccccc1] | ++ | 586.1 | 2.0 |

TABLE 1-continued

| Compound Id | Structure | ELISA IC$_{50}$ (nM) | MS (M + H)$^+$ | RP-HPLC R$_t$ (min) |
|---|---|---|---|---|
| 1.011 | 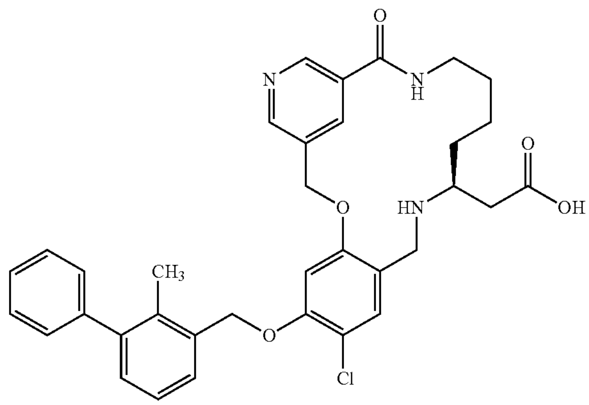 [SMILES: Cc1c(COc2cc3c(cc2Cl)CN[C@H](CC(=O)O)CCCCNC(=O)c2cncc(c2)CO3)cccc1-c1ccccc1] | ++ | 614.2 | 2.1 |
| 1.012 | 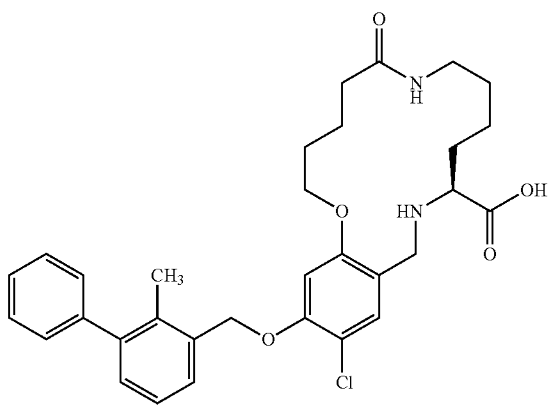 [SMILES: Cc1c(COc2cc3c(cc2Cl)CN[C@H](C(=O)O)CCCCNC(=O)CCCCO3)cccc1-c1ccccc1] | ++ | 565.2 | 2.2 |
| 1.013 | 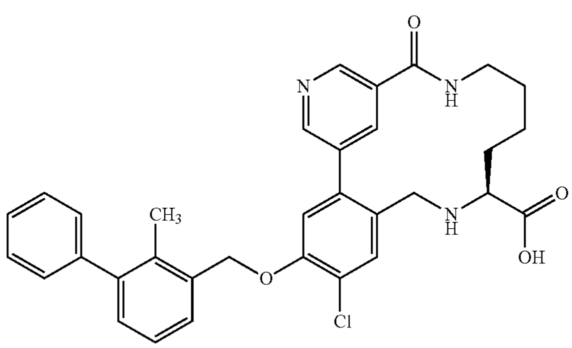 [SMILES: Cc1c(COc2cc3c(cc2Cl)CN[C@H](C(=O)O)CCCCNC(=O)c2cncc-3c2)cccc1-c1ccccc1] | + | 570.1 | 2.3 |
| 1.014 | 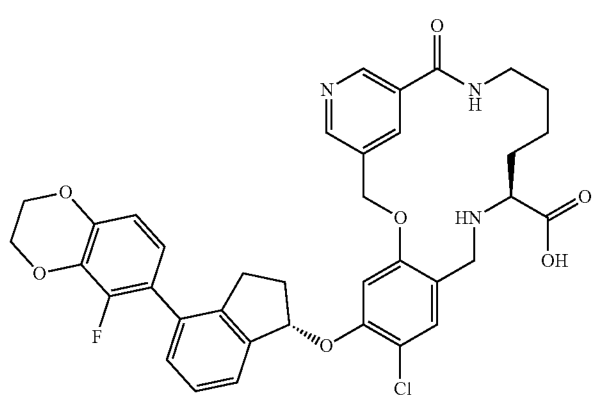 [SMILES: O=C1NCCCC[C@@H](C(=O)O)NCc2cc(Cl)c(O[C@H]3CCc4c(-c5ccc6c(c5F)OCCO6)cccc43)cc2OCc2cncc1c2] | +++ | 688.2 | 2.2 |

TABLE 1-continued

| Compound Id | Structure | ELISA IC$_{50}$ (nM) | MS (M + H)$^+$ | RP-HPLC R$_t$ (min) |
|---|---|---|---|---|
| 1.015 | 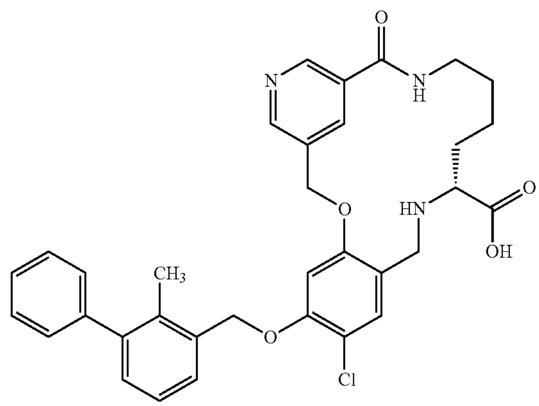 [SMILES: Cc1c(COc2cc3c(cc2Cl)CN[C@@H](C(=O)O)CCCCNC(=O)c2cncc(c2)CO3)cccc1-c1ccccc1] | +++ | 601.2 | 2.4 |
| 1.016 | 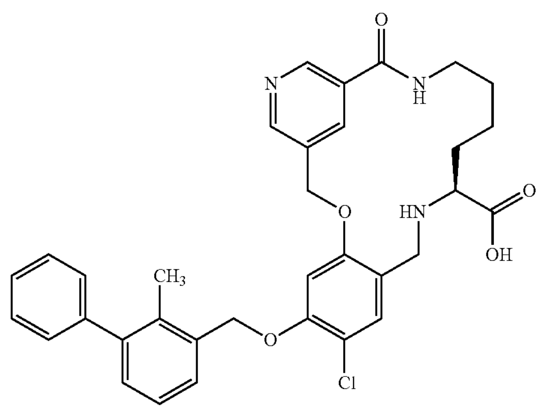 [SMILES: Cc1c(COc2cc3c(cc2Cl)CN[C@H](C(=O)O)CCCCNC(=O)c2cncc(c2)CO3)cccc1-c1ccccc1] | +++ | 600.1 | 2.3 |
| 1.017 | 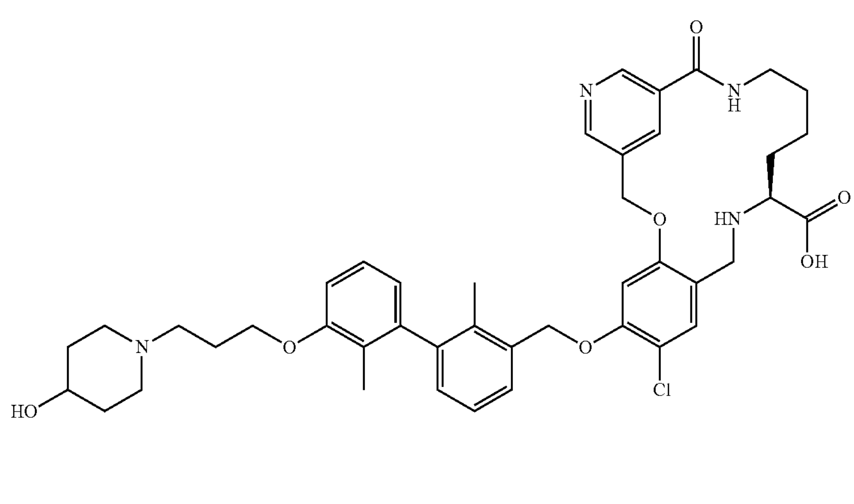 [SMILES: Cc1c(COc2cc3c(cc2Cl)CN[C@H](C(=O)O)CCCCNC(=O)c2cncc(c2)CO3)cccc1-c1cccc(OCCCN2CCC(O)CC2)c1C] | +++ | 758.7 | 1.8 |

TABLE 1-continued

| Compound Id | Structure | ELISA IC$_{50}$ (nM) | MS (M + H)$^+$ | RP-HPLC R$_t$ (min) |
|---|---|---|---|---|
| 1.018 | 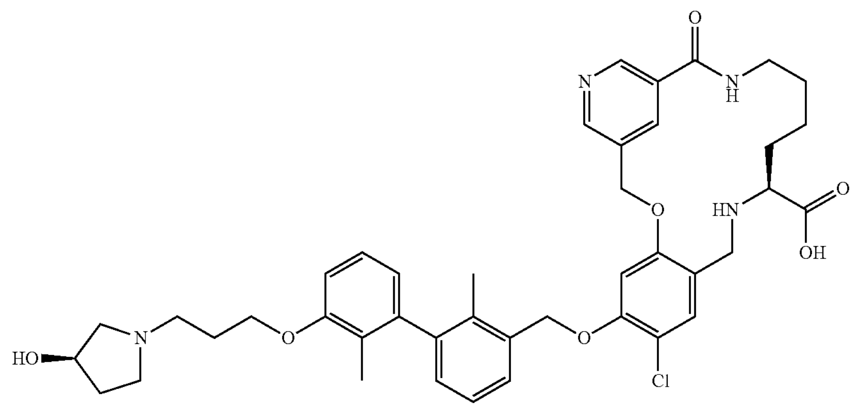 [SMILES: Cc1c(COc2cc3c(cc2Cl)CN[C@H](C(=O)O)CCCCNC(=O)c2cncc(c2)CO3)cccc1-c1cccc(OCCCN2CC[C@@H](O)C2)c1C] | +++ | 758.7 | 1.8 |
| 1.019 | 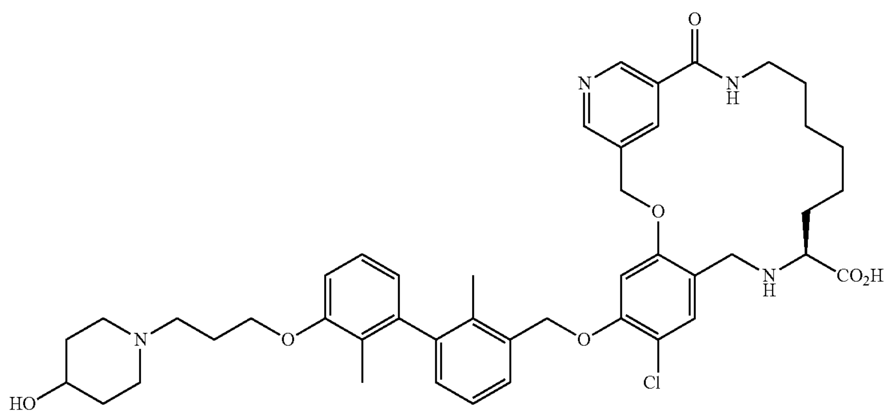 [SMILES: Cc1c(COc2cc3c(cc2Cl)CN[C@H](C(=O)O)CCCCCCNC(=O)c2cncc(c2)CO3)cccc1-c1cccc(OCCCN2CCC(O)CC2)c1C] | +++ | 800.7 | 1.9 |
| 1.020 | 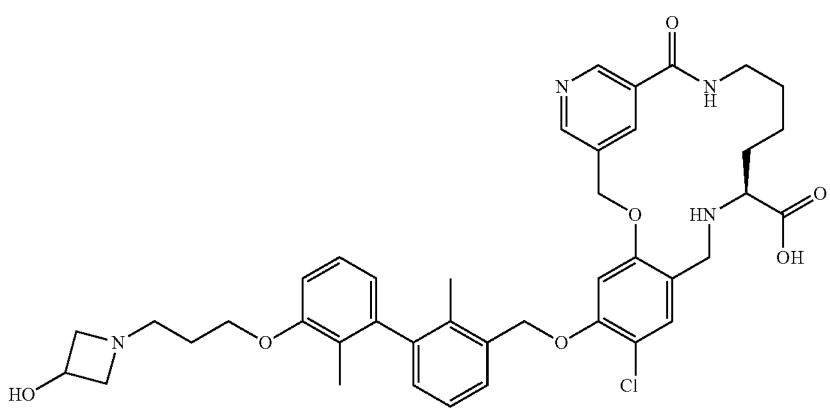 [SMILES: Cc1c(COc2cc3c(cc2Cl)CN[C@H](C(=O)O)CCCCNC(=O)c2cncc(c2)CO3)cccc1-c1cccc(OCCCN2CC(O)C2)c1C] | +++ | 743.5 | 1.7 |

TABLE 1-continued

| Compound Id | Structure | ELISA IC$_{50}$ (nM) | MS (M + H)$^+$ | RP-HPLC R$_t$ (min) |
|---|---|---|---|---|
| 1.021 | 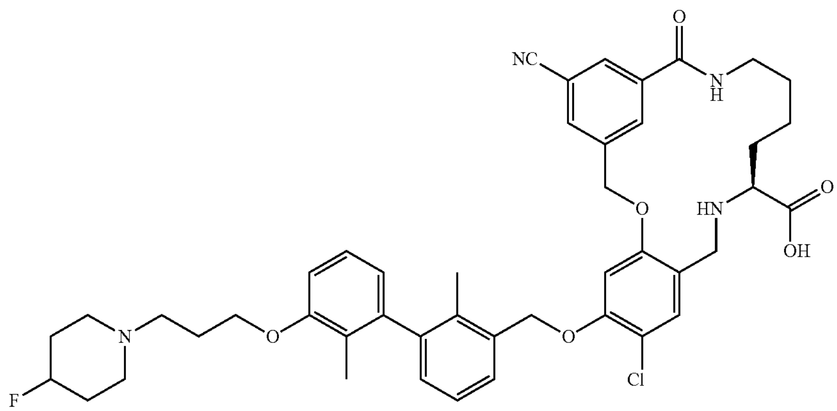 [SMILES: Cc1c(COc2cc3c(cc2Cl)CN[C@H](C(=O)O)CCCCNC(=O)c2cc(C#N)cc(c2)CO3)cccc1-c1cccc(OCCCN2CCC(F)CC2)c1C] | +++ | 797.5 | 2.0 |
| 1.022 | 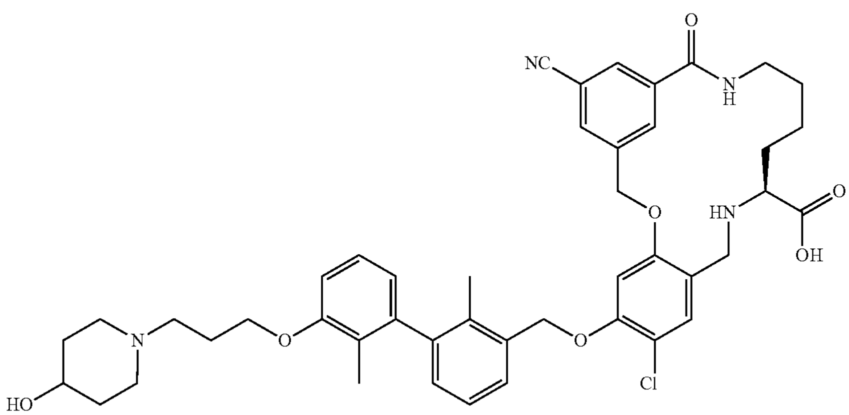 [SMILES: Cc1c(COc2cc3c(cc2Cl)CN[C@H](C(=O)O)CCCCNC(=O)c2cc(C#N)cc(c2)CO3)cccc1-c1cccc(OCCCN2CCC(O)CC2)c1C] | +++ | 796.8 | 2.4 |
| 1.023 | 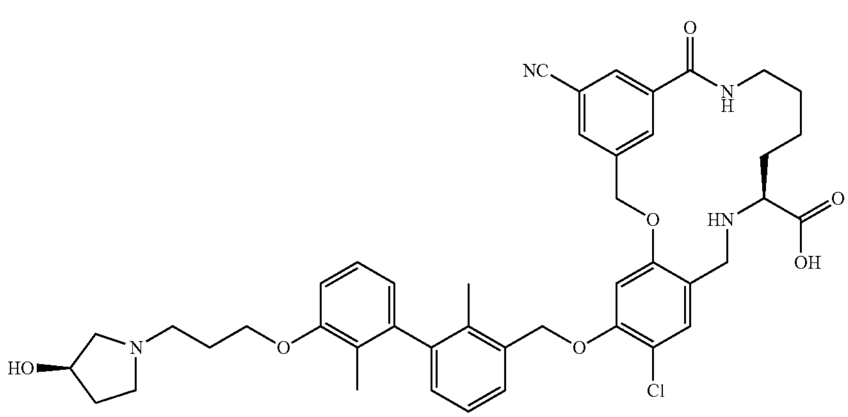 [SMILES: Cc1c(COc2cc3c(cc2Cl)CN[C@H](C(=O)O)CCCCNC(=O)c2cc(C#N)cc(c2)CO3)cccc1-c1cccc(OCCCN2CC[C@@H](O)C2)c1C] | +++ | 782.8 | 2.2 |

TABLE 1-continued

| Compound Id | Structure | ELISA IC$_{50}$ (nM) | MS (M+H)$^+$ | RP-HPLC R$_t$ (min) |
|---|---|---|---|---|
| 1.024 | 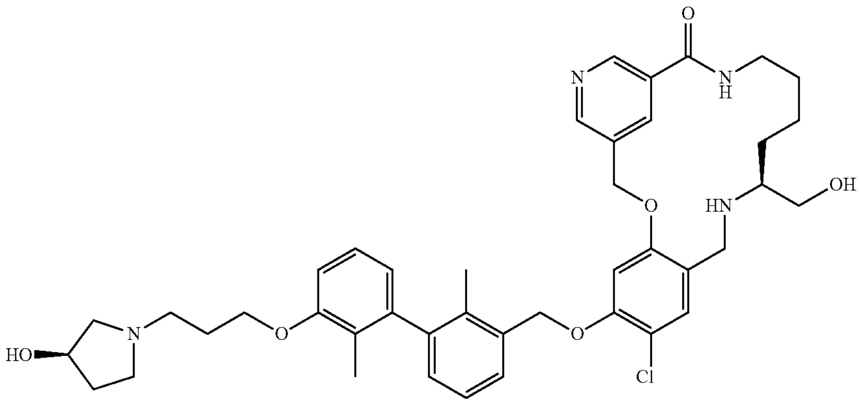 [SMILES: Cc1c(COc2cc3c(cc2Cl)CN[C@H](CO)CCCCNC(=O)c2cncc(c2)CO3)cccc1-c1cccc(OCCCN2CC[C@@H](O)C2)c1C] | +++ | 743.2 | 2.3 |
| 1.025 | 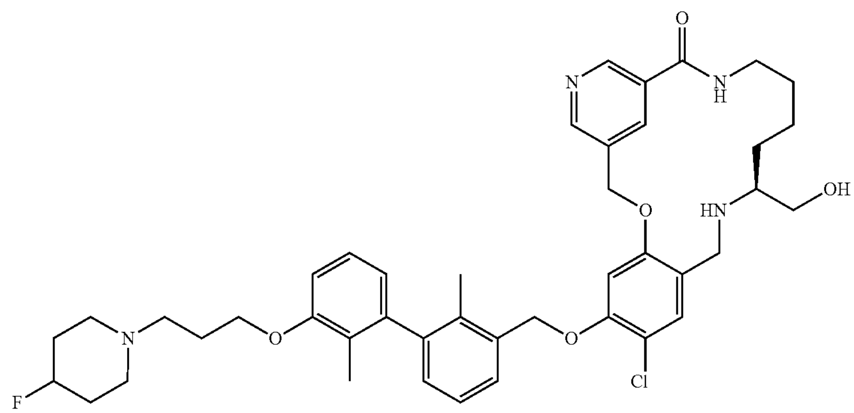 [SMILES: Cc1c(COc2cc3c(cc2Cl)CN[C@H](CO)CCCCNC(=O)c2cncc(c2)CO3)cccc1-c1cccc(OCCCN2CCC(F)CC2)c1C] | +++ | 759.3 | 1.9 |

What is claimed is:

1. A method of treating a cancer mediated by the PD-1 signaling pathway, comprising administering to the subject a therapeutically effective amount of a compound of Formula IIa1 or Formula IIb1:

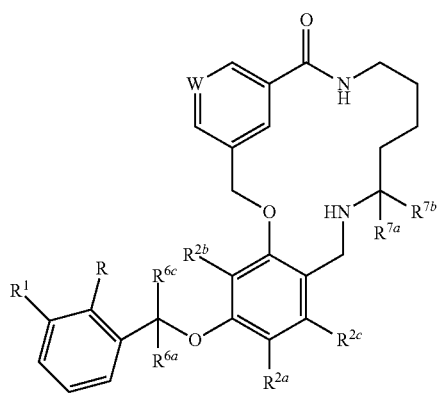

(IIa1)

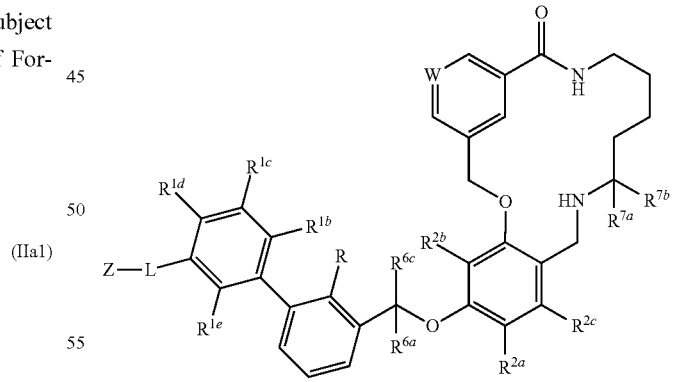

(IIb1)

or a pharmaceutically acceptable salt thereof; wherein:
W is N or C(R$^9$);
R is selected from the group consisting of H, halogen, CN, C$_{1-3}$ haloalkyl, C$_{1-3}$ alkyl and C$_{1-3}$ alkoxy;
R$^1$ is phenyl, optionally substituted with 1 to 3 R$^{1a}$ substituents;
each R$^{1a}$ is independently selected from halogen, C$_{1-8}$ alkyl, O—C$_{1-8}$ alkyl, O—C$_{1-8}$ haloalkyl, —NR$^a$R$^b$, and CN, and optionally when two R$^{1a}$ substituents are on adjacent atoms, they are combined to form a fused six-membered heterocyclic ring optionally substituted with from 1 to 3 substituents independently selected from oxo, $C_{1-8}$ haloalkyl and $C_{1-8}$ alkyl;

each $R^a$ and $R^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, wherein the five or six-membered ring is optionally substituted with oxo;

each of $R^{1b}$, $R^{1c}$, $R^{1d}$ and $R^{1e}$ is independently selected from the group consisting of H, halogen, $CF_3$, CN, $C_{1-4}$ alkyl and —O—$C_{1-4}$ alkyl, wherein the $C_{1-4}$ alkyl and —O—$C_{1-4}$ alkyl are optionally further substituted with halogen, hydroxyl, methoxy or ethoxy;

wherein Z—L— is a member selected from the group consisting of:

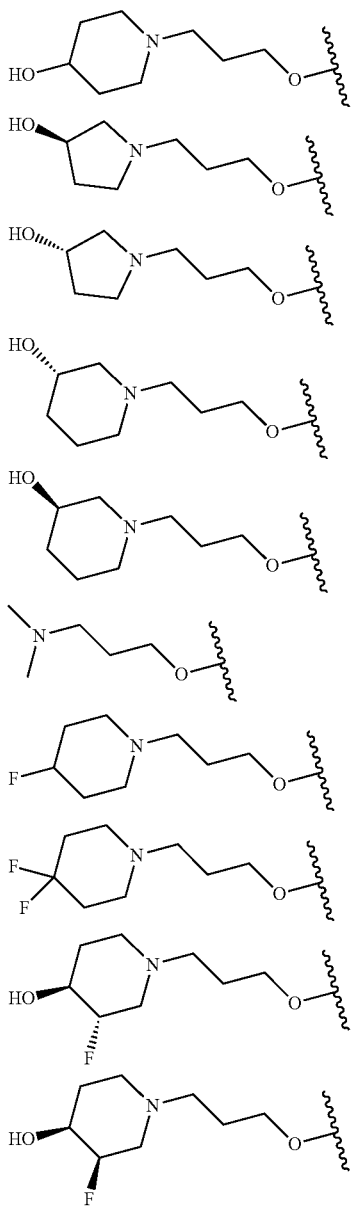

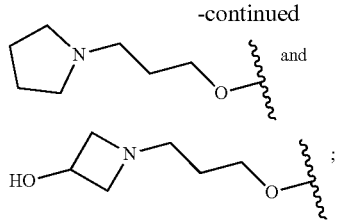

$R^{2b}$ and $R^{2c}$ are both H and $R^{2a}$ is selected from the group consisting of halogen, $C_{1-4}$ alkyl, $C_{2-4}$ alkenyl, $C_{1-3}$ haloalkyl, —CN, —OMe and OEt;

$R^{6a}$ is H;

$R^{6c}$ is selected from the group consisting of H, $C_{1-4}$ alkyl and $C_{1-4}$ haloalkyl;

each $R^{7a}$ and $R^{7b}$ is independently selected from the group consisting of H, $CO_2H$, and $CH_2OH$; and $R^9$ is CN.

2. The method of claim 1, comprising administering to the subject a therapeutically effective amount of a compound of Formula (IIa1).

3. The method of claim 1, comprising administering to the subject a therapeutically effective amount of a compound of Formula (IIb1).

4. The method of claim 1, wherein $R^1$ is selected from the group consisting of:

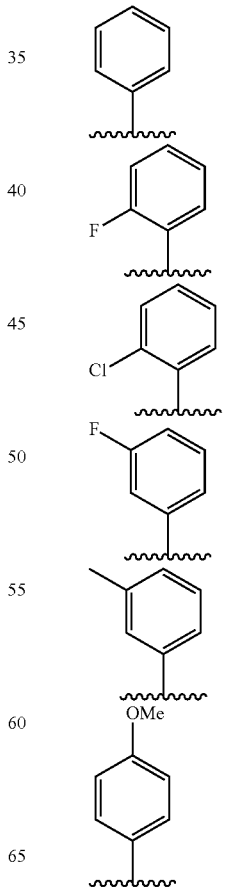

-continued
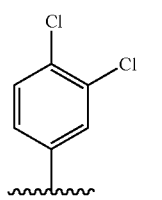
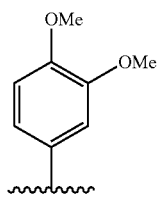
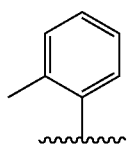
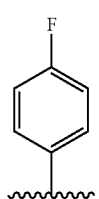
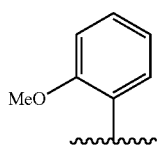
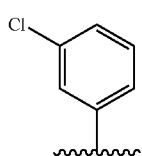
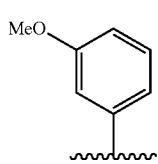
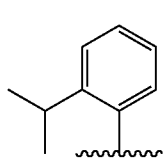
-continued
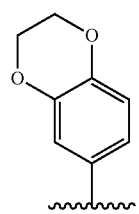
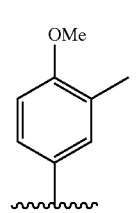
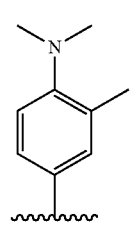
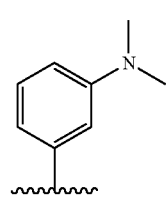
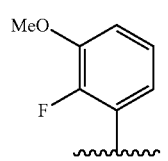
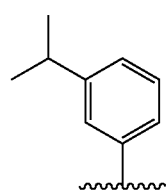
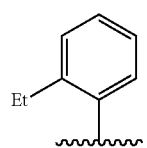
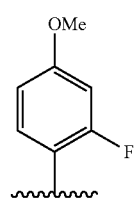

91
-continued
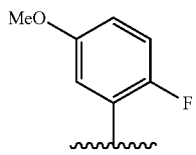
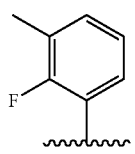
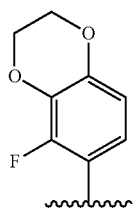
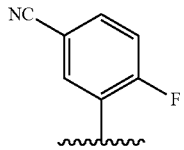
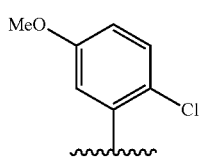
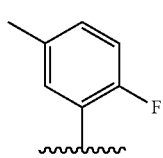
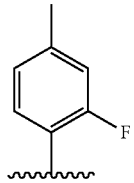
92
-continued
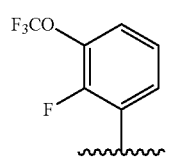
5. The method of claim 1, wherein Z-L- is a member selected from the group consisting of:
6. The method of claim 1, wherein $R^{2b}$ and $R^{2c}$ are both H and $R^{2a}$ is halogen.
7. The method of claim 1, wherein $R^{2b}$ and $R^{2c}$ are both H and $R^{2a}$ is Cl.
8. A compound or a pharmaceutically acceptable salt thereof, selected from the group consisting of
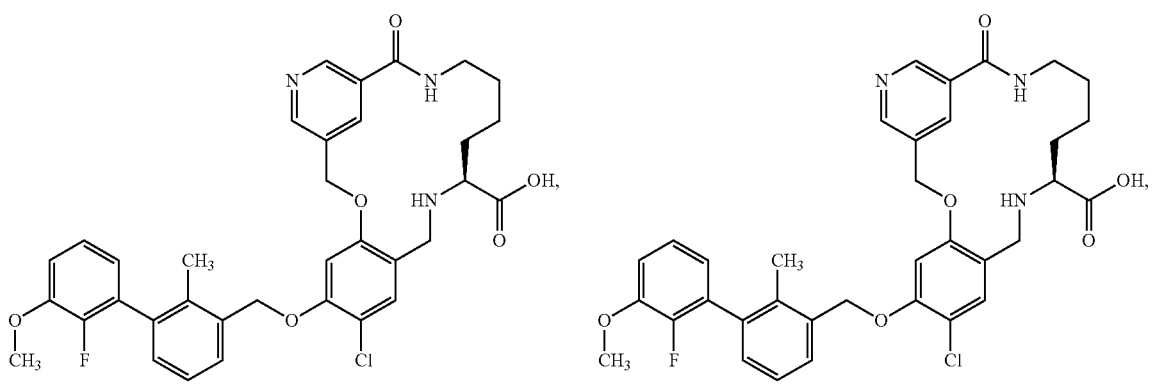

-continued
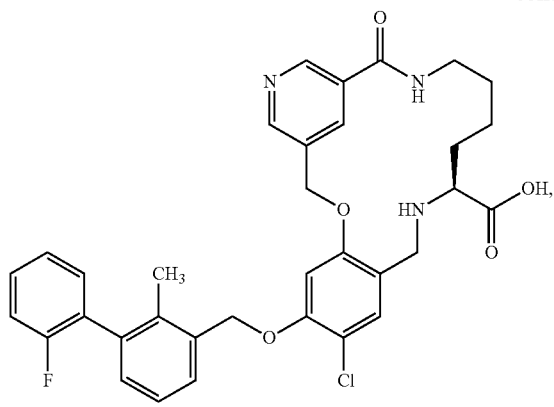
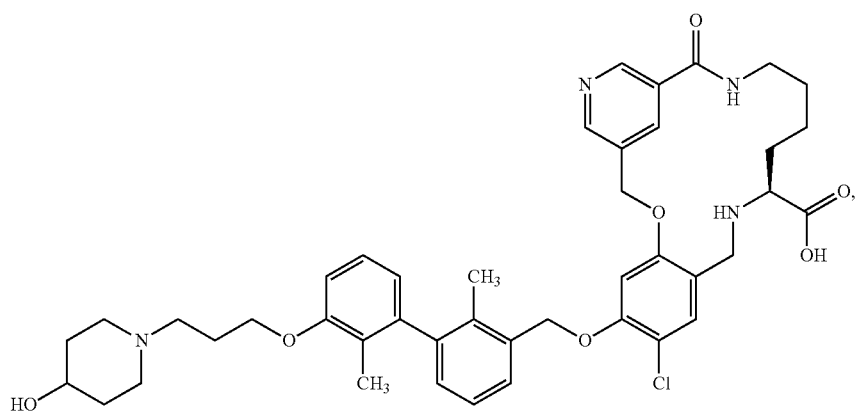
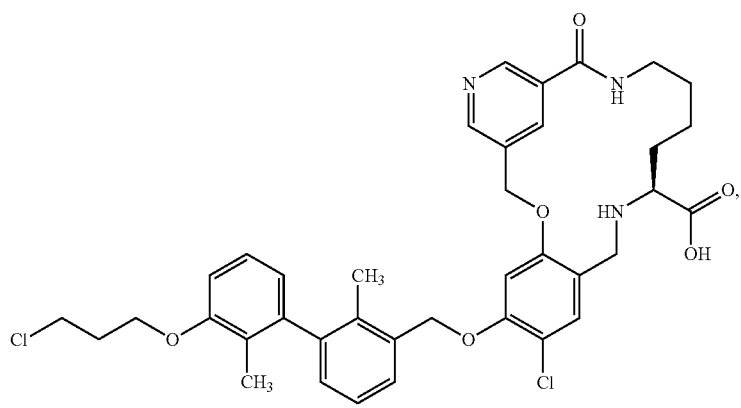
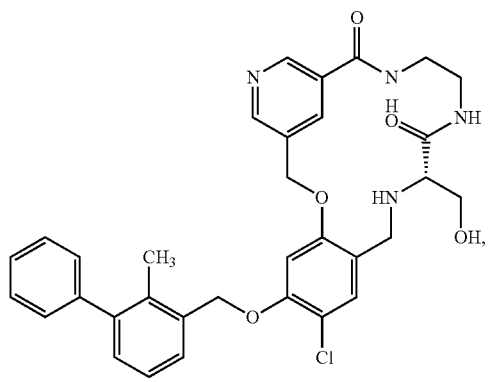
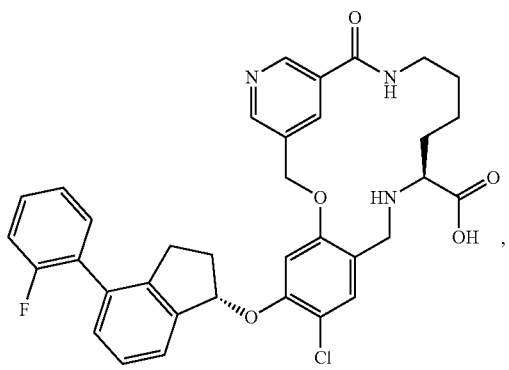

95
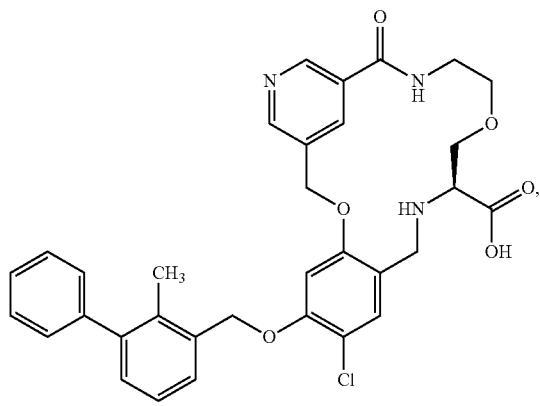
96
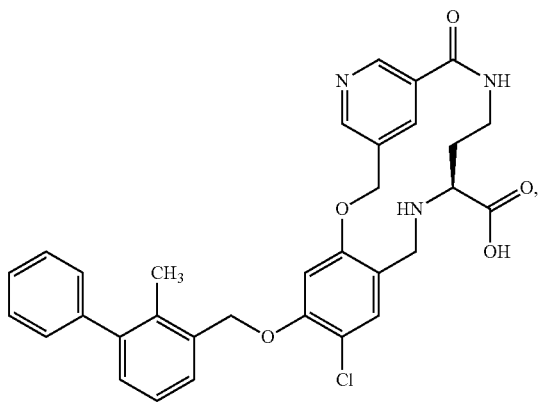
-continued
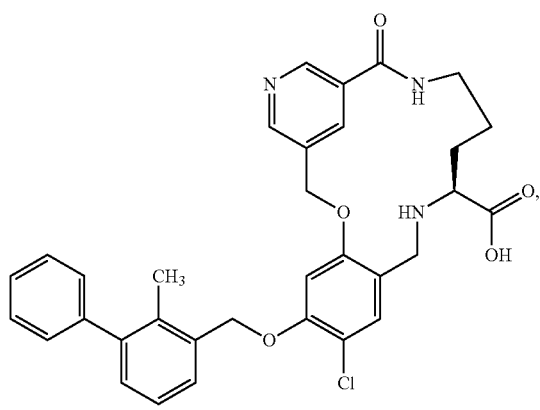
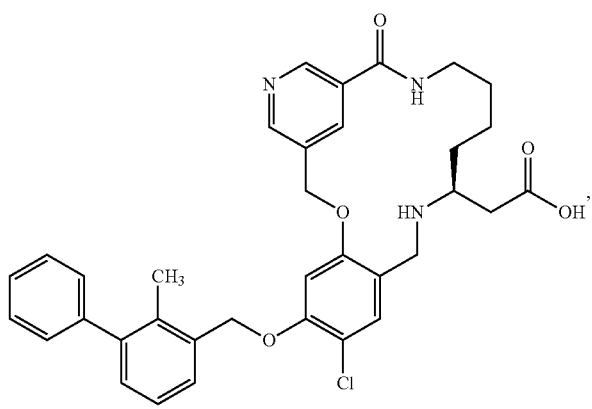
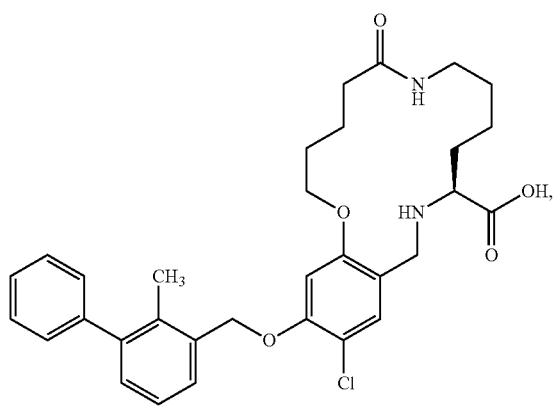
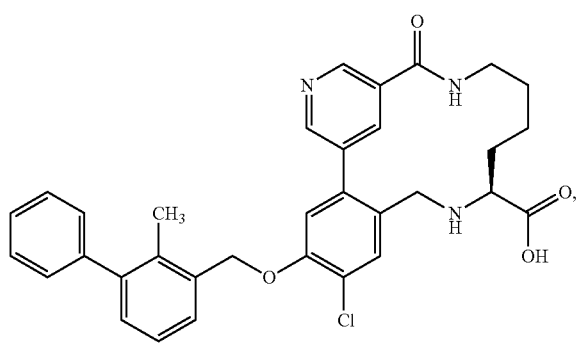

-continued
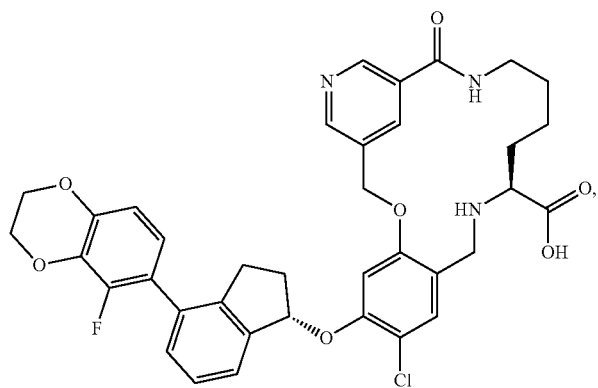
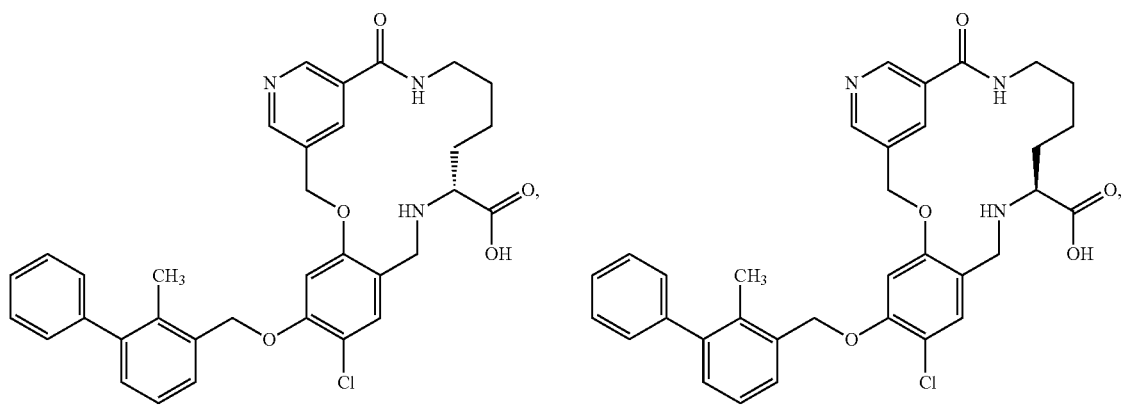
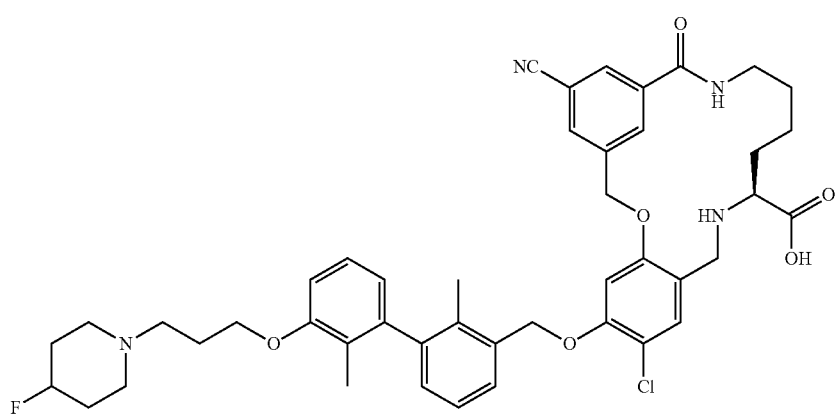
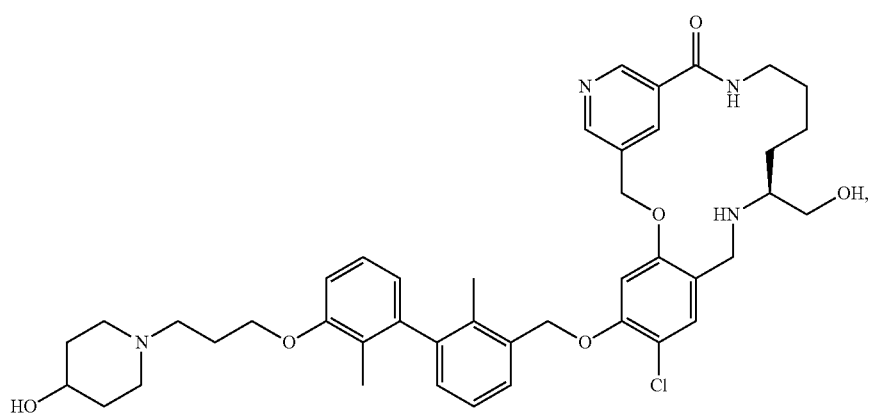

-continued
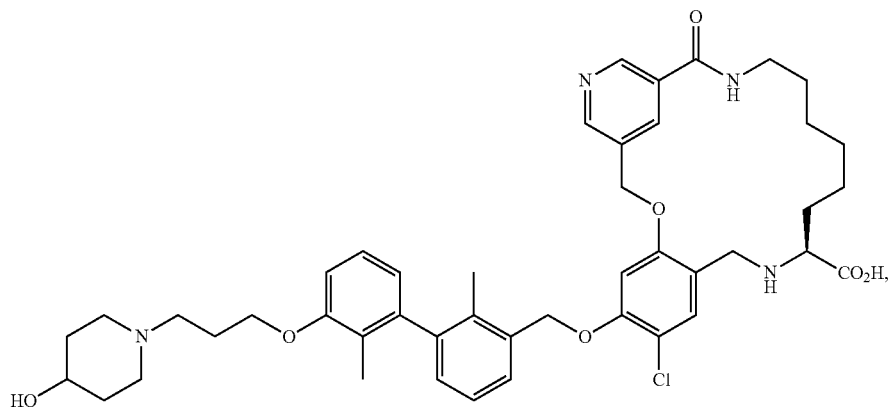
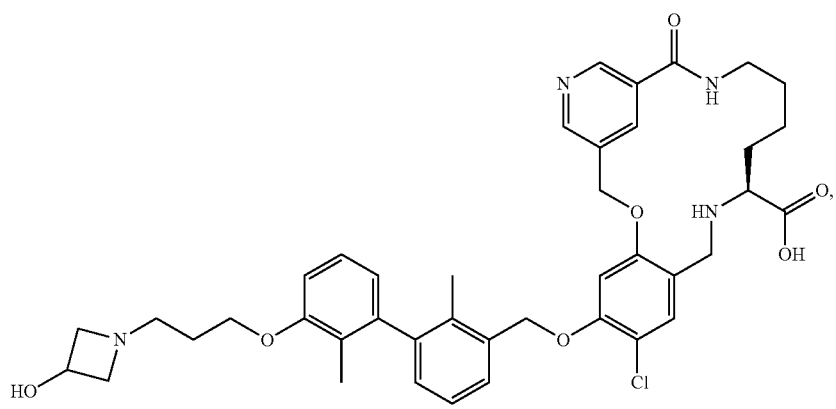
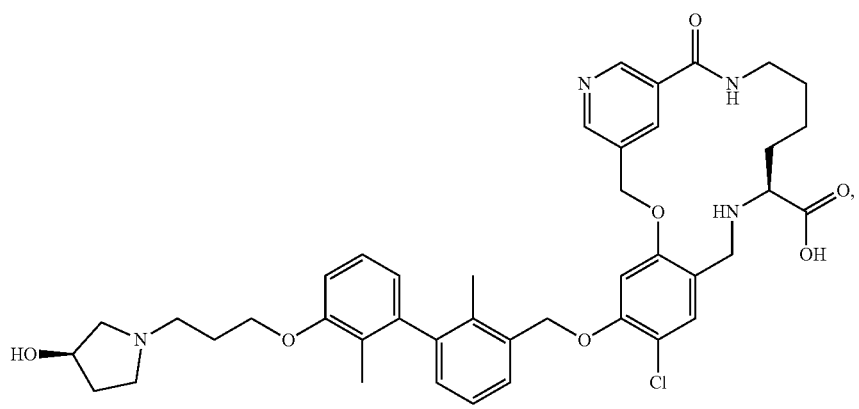
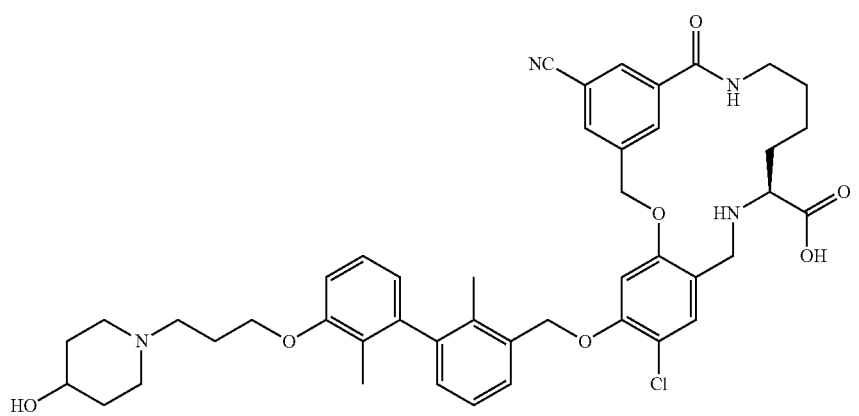

-continued
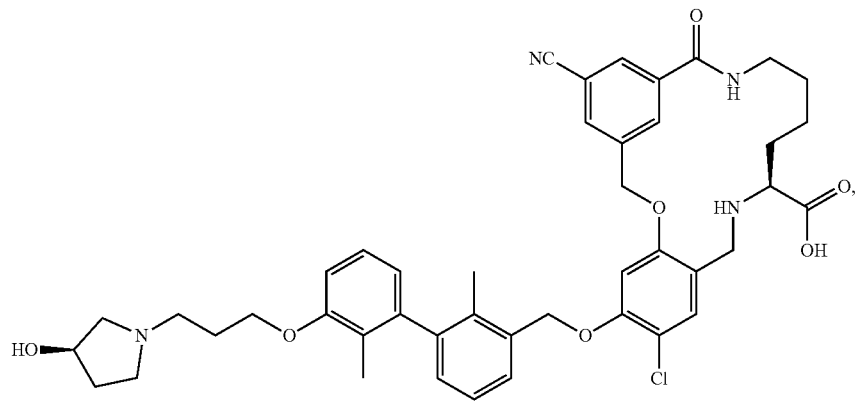
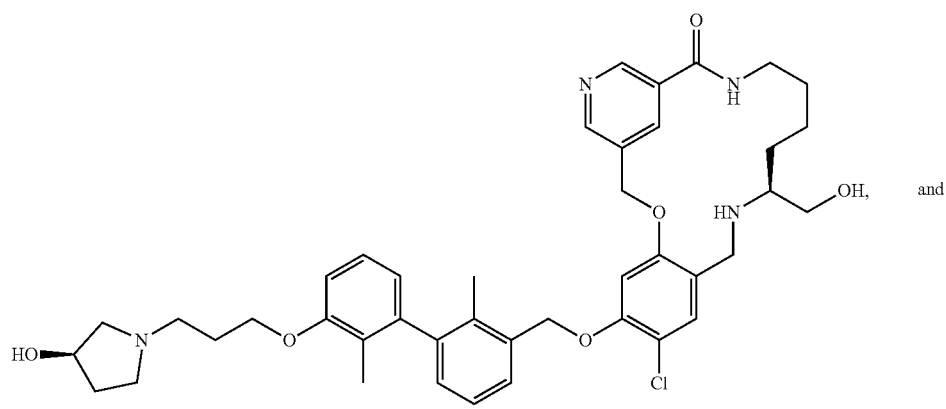 and
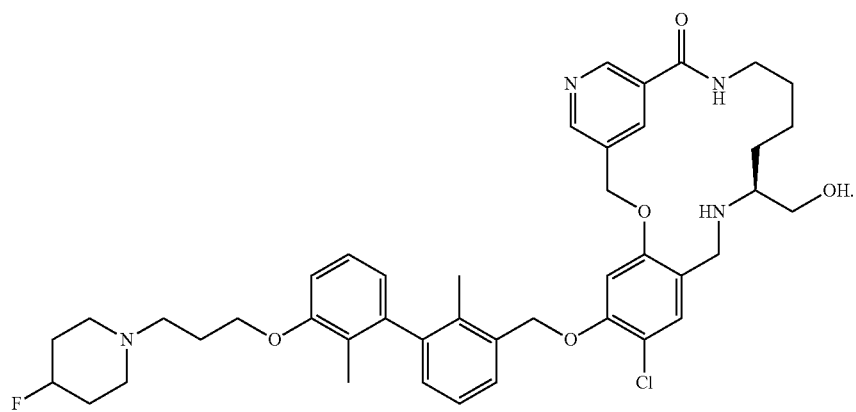 [SMILES: Cc1c(COc2cc3c(cc2Cl)CN[C@H](CO)CCCCNC(=O)c2cncc(c2)CO3)cccc1-c1cccc(OCCCN2CCC(F)CC2)c1C]

9. A pharmaceutical composition comprising a compound of claim 8, or a pharmaceutically acceptable salt thereof, and a pharmaceutically acceptable excipient.

10. The pharmaceutical composition of claim 9, further comprising one or more additional therapeutic agents.

11. The pharmaceutical composition of claim 10, wherein the one or more additional therapeutic agents is selected from the group consisting of an antimicrobial agent, an antiviral agent, a cytotoxic agent, a gene expression modulatory agent, a chemotherapeutic agent, an anti-cancer agent, an anti-angiogenic agent, an immunotherapeutic agent, an anti-hormonal agent, an anti-fibrotic agent, radiotherapy, a radiotherapeutic agent, an anti-neoplastic agent, and an anti-proliferation agent.

12. The method of claim 1, wherein the cancer mediated by the PD-1 signaling pathway is selected from the group consisting of melanoma, glioblastoma, esophagus tumor, nasopharyngeal carcinoma, uveal melanoma, lymphoma, lymphocytic lymphoma, primary CNS lymphoma, T-cell lymphoma, diffuse large B-cell lymphoma, primary mediastinal large B-cell lymphoma, prostate cancer, castration-resistant prostate cancer, chronic myelocytic leukemia, Kaposi's sarcoma, fibrosarcoma, liposarcoma, chondrosarcoma, osteogenic sarcoma, angiosarcoma, lymphangiosarcoma, synovioma, meningioma, leiomyosarcoma, rhabdomyosarcoma, sarcoma of soft tissue, sarcoma, biliary tumor, basal cell carcinoma, thymus neoplasm, cancer of the thyroid gland, cancer of the parathyroid gland, uterine cancer, cancer of the adrenal gland, Merkel cell carcinoma, nerve tumor, follicle center lymphoma, colon cancer, Hodgkin's disease, non-Hodgkin's lymphoma, leukemia, chronic or acute leukemias including acute myeloid leukemia, chronic myeloid leukemia, acute lymphoblastic leukemia, chronic lymphocytic leukemia, multiple myeloma, ovary tumor, myelodysplastic syndrome, cutaneous or intraocular malignant melanoma, renal cell carcinoma, small-cell lung cancer, lung cancer, mesothelioma, breast cancer, squamous non-small cell lung cancer (SCLC), non-squamous NSCLC, colorectal cancer, ovarian cancer, gastric cancer, hepatocellular carcinoma, pancreatic carcinoma, pancreatic cancer, Pancreatic ductal adenocarcinoma, squamous cell carcinoma of the head and neck, cancer of the head or neck, cancer of the gastrointestinal tract, stomach cancer, bone cancer, skin cancer, rectal cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the urethra, cancer of the penis, cancer of the bladder, cancer of the kidney, cancer of the ureter, carcinoma of the renal pelvis, neoplasm of the central nervous system (CNS), tumor angiogenesis, spinal axis tumor, brain stem glioma, pituitary adenoma, epidermoid cancer, carcinoma, adenocarcinoma, papillary carcinoma, cystadenocarcinoma, bronchogenic carcinoma, renal cell carcinoma, transitional cell carcinoma, choriocarcinoma, seminoma, embryonal carcinoma, wilm's tumor, pleomorphic adenoma, liver cell papilloma, renal tubular adenoma, cystadenoma, papilloma, adenoma, leiomyoma, rhabdomyoma, hemangioma, lymphangioma, osteoma, chondroma, lipoma and fibroma.

13. The method of claim 12, further comprising administering to the subject a therapeutically effective amount of one or more additional therapeutic agents.

14. The method of claim 13, wherein the one or more additional therapeutic agents is selected from the group consisting of a cytotoxic agent, a gene expression modulatory agent, a chemotherapeutic agent, an anti-cancer agent, an anti-angiogenic agent, an immunotherapeutic agent, an anti-hormonal agent, an anti-fibrotic agent, radiotherapy, a radiotherapeutic agent, an anti-neoplastic agent, and an anti-proliferation agent.

15. The compound of claim 8 or a pharmaceutically acceptable salt thereof, having the formula

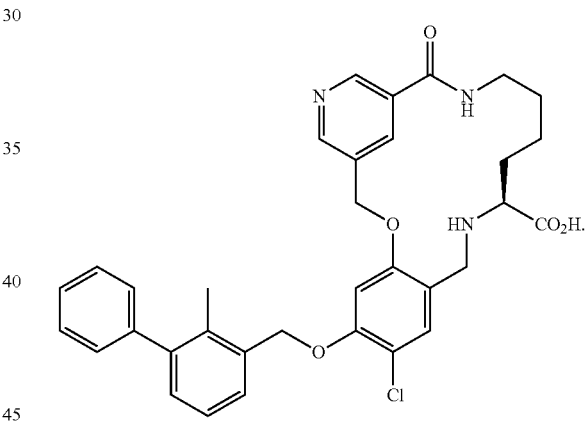

16. The compound of claim 8 or a pharmaceutically acceptable salt thereof, having the formula

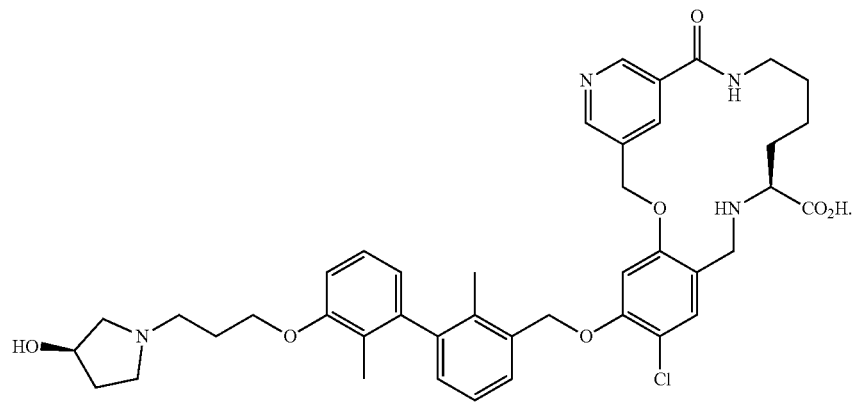 [SMILES: Cc1c(COc2cc3c(cc2Cl)CN[C@H](C(=O)O)CCCCNC(=O)c2cncc(c2)CO3)cccc1-c1cccc(OCCCN2CC[C@@H](O)C2)c1C]

17. The compound of claim 8 or a pharmaceutically acceptable salt thereof, having the formula
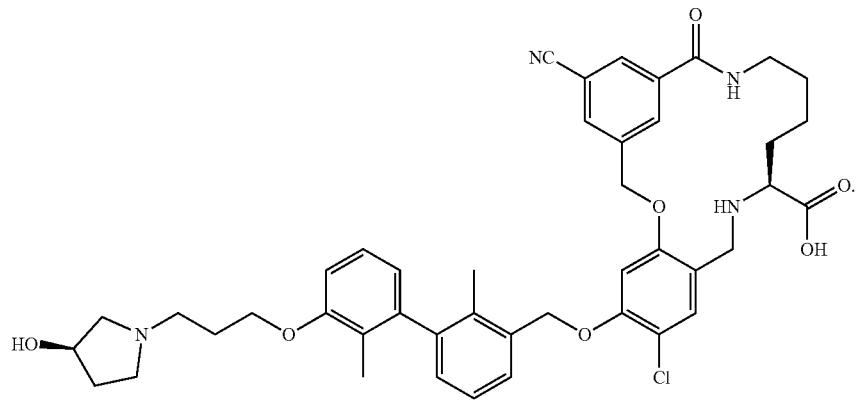 [SMILES: Cc1c(COc2cc3c(cc2Cl)CN[C@H](C(=O)O)CCCCNC(=O)c2cc(C#N)cc(c2)CO3)cccc1-c1cccc(OCCCN2CC[C@@H](O)C2)c1C]
18. The compound of claim 8 or a pharmaceutically acceptable salt thereof, having the formula
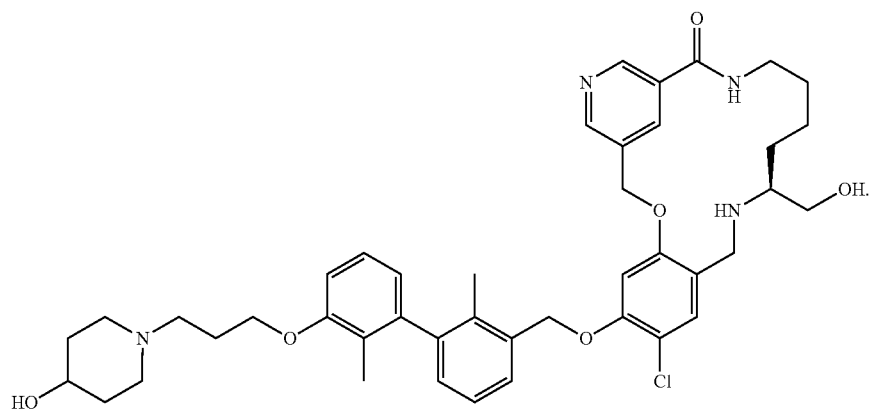 [SMILES: Cc1c(COc2cc3c(cc2Cl)CN[C@H](CO)CCCCNC(=O)c2cncc(c2)CO3)cccc1-c1cccc(OCCCN2CCC(O)CC2)c1C]
* * * * *